US009840680B2

(12) United States Patent
Holland et al.

(10) Patent No.: US 9,840,680 B2
(45) Date of Patent: Dec. 12, 2017

(54) FRAGRANCE COMPOSITIONS COMPRISING IONIC LIQUIDS

(71) Applicant: The Procter & Gamble Company, Cincinnati, OH (US)

(72) Inventors: Lynette Anne Makins Holland, Abbots Langley (GB); Oreste Todini, Brussels (BE); David Michael Eike, West Chester, OH (US); Jose Maria Velazquez Mendoza, Ascot (GB); Sarah Anne Tozer, London (GB); Pauline Mary McNamee, Camberley (GB); Jonathan Richard Stonehouse, Windlesham (GB); William Eoghan Staite, Egham (GB); Henry Charles Reginald Fovargue, London (GB); Judith Ann Gregory, Fleet (GB); Kenneth Richard Seddon, Belfast (GB); Harambage Quintus Nimal Gunaratne, Belfast (GB); Alberto Vaca Puga, Belfast (GB); Julien Estager, Belfast (GB); Feng-Ling Wu, Belfast (GB); Shane Declan Devine, Belfast (GB); Marijana Blesic, Belfast (GB); Federico Maria Ferrero Vallana, Belfast (GB)

(73) Assignee: The Procter & Gamble Company, Cincinnati, OH (US)

( * ) Notice: Subject to any disclaimer, the term of this patent is extended or adjusted under 35 U.S.C. 154(b) by 33 days.

(21) Appl. No.: 14/865,152

(22) Filed: Sep. 25, 2015

(65) Prior Publication Data

US 2016/0115424 A1    Apr. 28, 2016

Related U.S. Application Data

(60) Provisional application No. 62/054,990, filed on Sep. 25, 2014.

(51) Int. Cl.

| *A61K 8/37* | (2006.01) |
|---|---|
| *A61K 8/41* | (2006.01) |
| *A61K 8/45* | (2006.01) |
| *A61K 8/46* | (2006.01) |
| *A61K 8/49* | (2006.01) |
| *A61Q 15/00* | (2006.01) |
| *A61Q 13/00* | (2006.01) |
| *C11B 9/00* | (2006.01) |

(52) U.S. Cl.

CPC .............. *C11B 9/0061* (2013.01); *A61K 8/37* (2013.01); *A61K 8/41* (2013.01); *A61K 8/416* (2013.01); *A61K 8/45* (2013.01); *A61K 8/466* (2013.01); *A61K 8/49* (2013.01); *A61Q 13/00* (2013.01); *A61Q 15/00* (2013.01); *A61K 2800/20* (2013.01)

(58) Field of Classification Search
None
See application file for complete search history.

(56) References Cited

U.S. PATENT DOCUMENTS

| 4,264,478 | A | 4/1981 | Seldner |
|---|---|---|---|
| 4,324,703 | A | 4/1982 | Seldner |
| 7,411,092 | B2 * | 8/2008 | Honma ................. C07C 217/08 564/292 |
| 7,435,318 | B2 | 10/2008 | Arlt et al. |
| 7,790,668 | B2 * | 9/2010 | Mueller ................. C07C 45/58 512/25 |
| 8,822,404 | B2 | 9/2014 | Wong et al. |
| 2004/0077519 | A1 | 4/2004 | Price et al. |
| 2006/0094620 | A1 | 5/2006 | Jordan, IV et al. |
| 2006/0166856 | A1 * | 7/2006 | Petrat .................. A61K 8/4946 512/2 |
| 2012/0046244 | A1 | 2/2012 | Rogers et al. |
| 2013/0280527 | A1 | 10/2013 | Niimi et al. |
| 2014/0178315 | A1 | 6/2014 | Gruber et al. |
| 2014/0287982 | A1 | 9/2014 | Wong et al. |
| 2015/0031596 | A1 | 1/2015 | Wong et al. |
| 2015/0275136 | A1 | 10/2015 | Si et al. |

OTHER PUBLICATIONS

Fragrance Fact Sheet from Scented Products Education and Information Association of Canada, copyright 2007, downloaded Jan. 16, 2017 from http://www.cctfa.ca/scented/facts_composition.html.*
Whitney L. Hough-Troutman, Marcin Smiglak, Scott Griffin, W. Matthew Reichert, Ilona Mirska, Jadwiga Jodynis-Liebert, Teresa Adamska, Jan Nawrot, Monika Stasiewicz, Robin D. Rogers and Juliusz Pernak. Ionic liquids with dual biological function: sweet and anti-microbial, hydrophobic quaternary ammonium-based salts. New J. Chem., 2009, 33, 26-33.*
U.S. Appl. No. 15/010,034, filed Jan. 29, 2016, Lynette Anne Makins Holland et al.
U.S. Appl. No. 62/247,738, filed Oct. 28, 2015, Lynette Anne Makins Holland et al.
U.S. Appl. No. 14/964,631, filed Dec. 10, 2015, Giulia Ottavia Bianchetti et al.
U.S. Appl. No. 62/183,193, filed Jun. 23, 2015, Giulia Ottavia Bianchetti et al.
All Office Actions U.S. Appl. No. 15/010,034.
Arce et al., Separation of aromatic hydrocarbons from alkanes using the ionic liquid1-ethyl-3-methylimidazolium bis{(trifluoromethyl)sulfonyl}amide, Green Chemistry, 2007, vol. 9, pp. 70-74.
Blesic et al., Controlled fragrance delivery in functionalised ionic liquid-enzyme systems, RSC Advances, 2013, 3:329-333.
Choi et al., Dual functional ionid liquids as plasticisers and antimicrobial agents for medical polymers, Green Chemistry, 2011, vol. 13, pp. 1527-1535.

(Continued)

*Primary Examiner* — Isaac Shomer
*Assistant Examiner* — Michael P Cohen
(74) *Attorney, Agent, or Firm* — Betty J. Zea

(57) ABSTRACT

The present invention relates to a fragrance composition comprising ionic liquids for enhanced evaporation of the perfume raw materials. The invention also relates to methods of use of the fragrance compositions for perfuming suitable substrates, particularly skin and hair.

3 Claims, 9 Drawing Sheets

(56) References Cited

OTHER PUBLICATIONS

Crosthwaite et al., Phase transition and decomposition temperatures, heat capacities and viscosities of pyridinium ionic liquids, Journal of Chemical Thermodynamics, vol. 37 (2005), pp. 559-568.
Davey, Ionic Liquids in Consumer Products, Perfumer & Flavorist, 2008, vol. 33 (4), pp. 34-35.
Hough-Troutman et al., Ionic liquids with dual biological function: sweet and anti-microbial, hydrophobic quaternary ammonium-based salts, New Journal of Chemistry, 2009, vol. 33, pp. 26-33.
International Search Report and Written Opinion of the International Searching Authority, Application No. PCT/US2015/052085, dated Dec. 14, 2015, 12 pages.
Kuca et al., Preparation of Benzalkonium Salts Differing in the Length of a Side Alkyl Chain, Molecules 2007, vol. 12, pp. 2341-2347.
Li et al., Effect of Mono- and Di-ethanolammonium Formate Ionic Liquids on the Volatility of Water, Ethanol, and Methanol, Chinese Journal of Chemical Engineering, 21(10) 1162-1171 (2013).
Moshel et al., Demonstrating perfume fixation, Perfumer & Flavorist, 1982, vol. 7, pp. 41-47.
Sullivan, Solvents by Design, Innovations in Pharmaceutical Technology, 2006, pp. 75-77.
Forsyth et al., Utilisation of ionic liquid solvents for the synthesis of Lily-of-the-Valley fragrance {_-Lilial®; 3-(4-t-butylphenyl)-2-methylpropanal}, Journal of Molecular Catalysis A: Chemical 231, 2005, pp. 61-66.

* cited by examiner

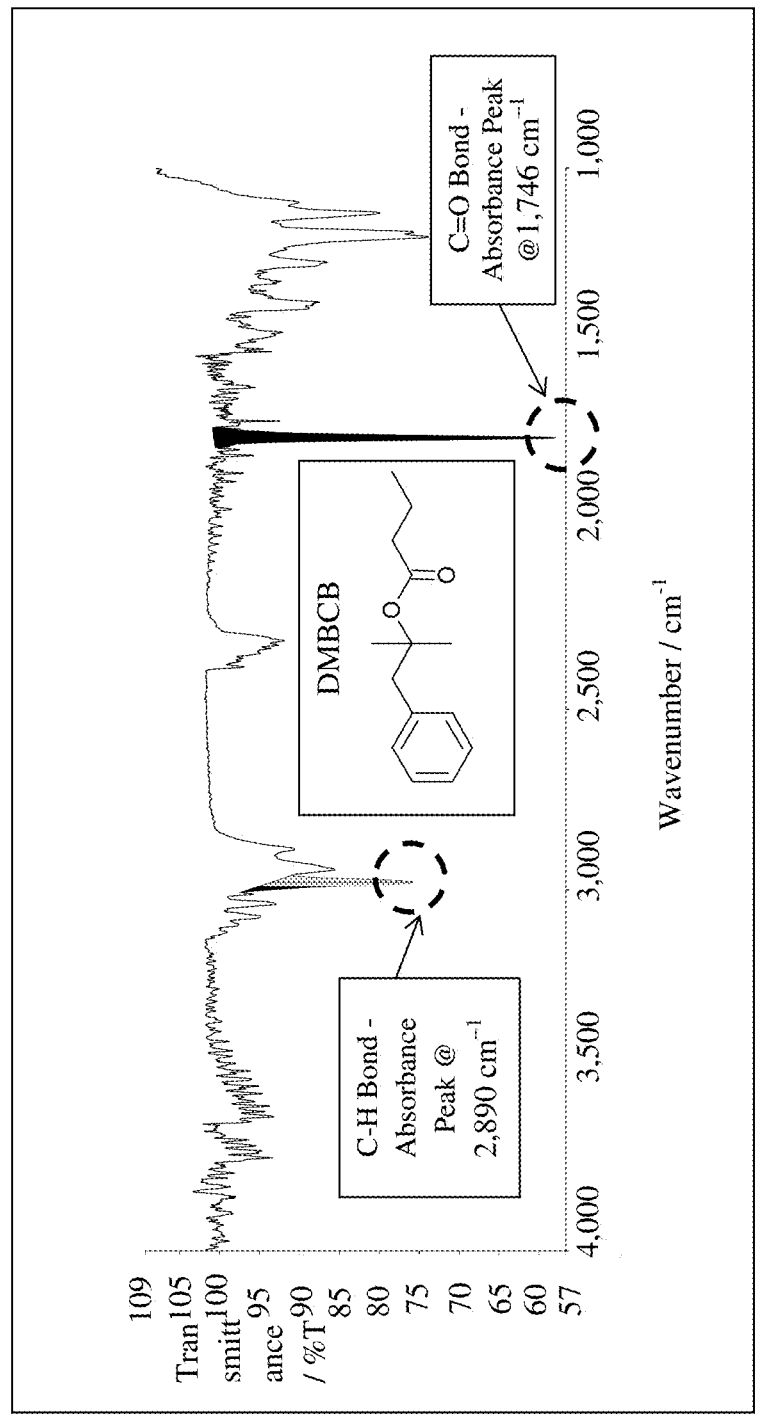
Figure 1 – Gas-Phase Infrared (IR) Spectrum of DMBCB at 45°C (8 metres)

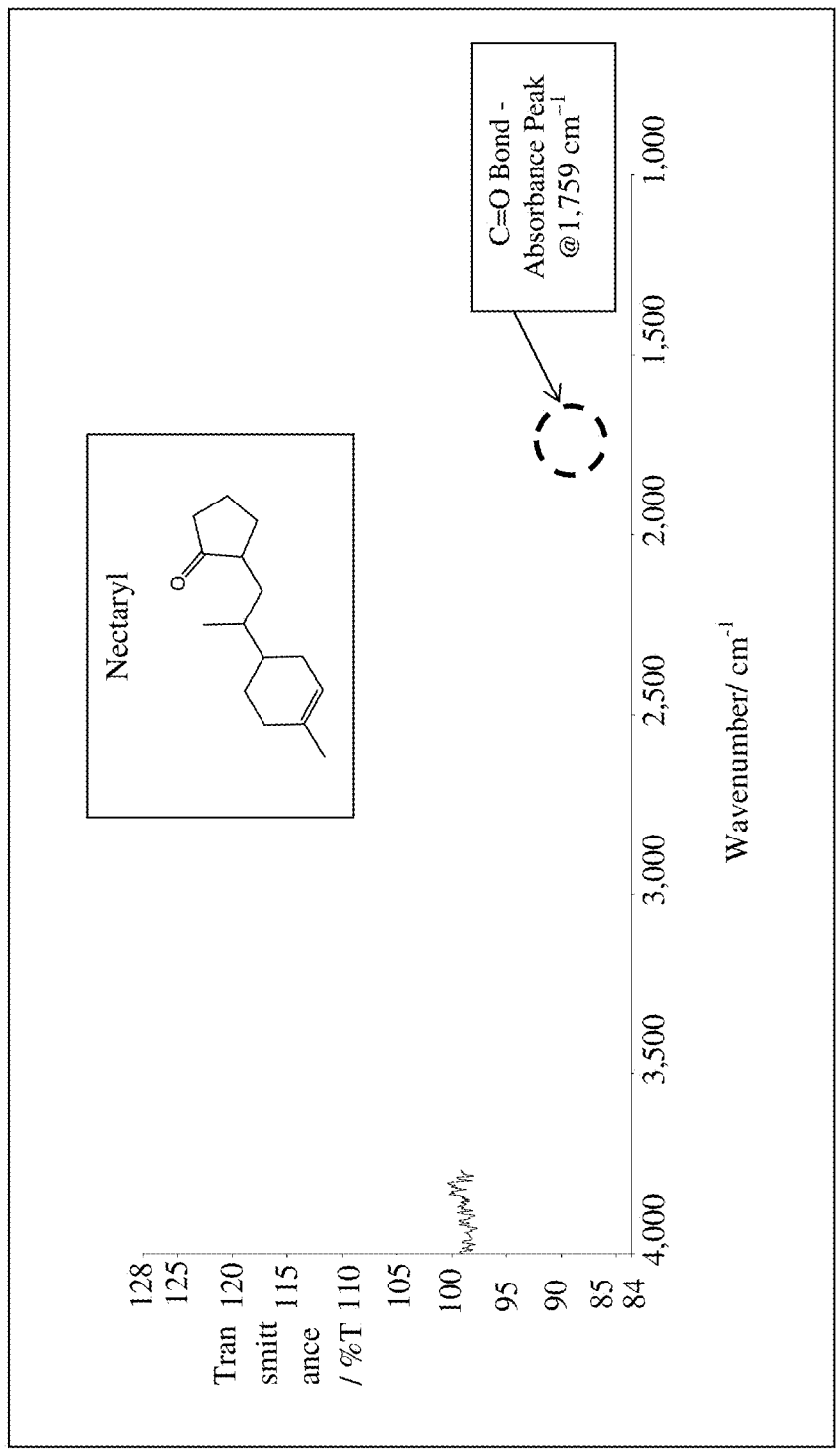
Figure 2 – Gas-Phase Infrared (IR) Spectrum of Nectaryl at 100°C (8 metres)

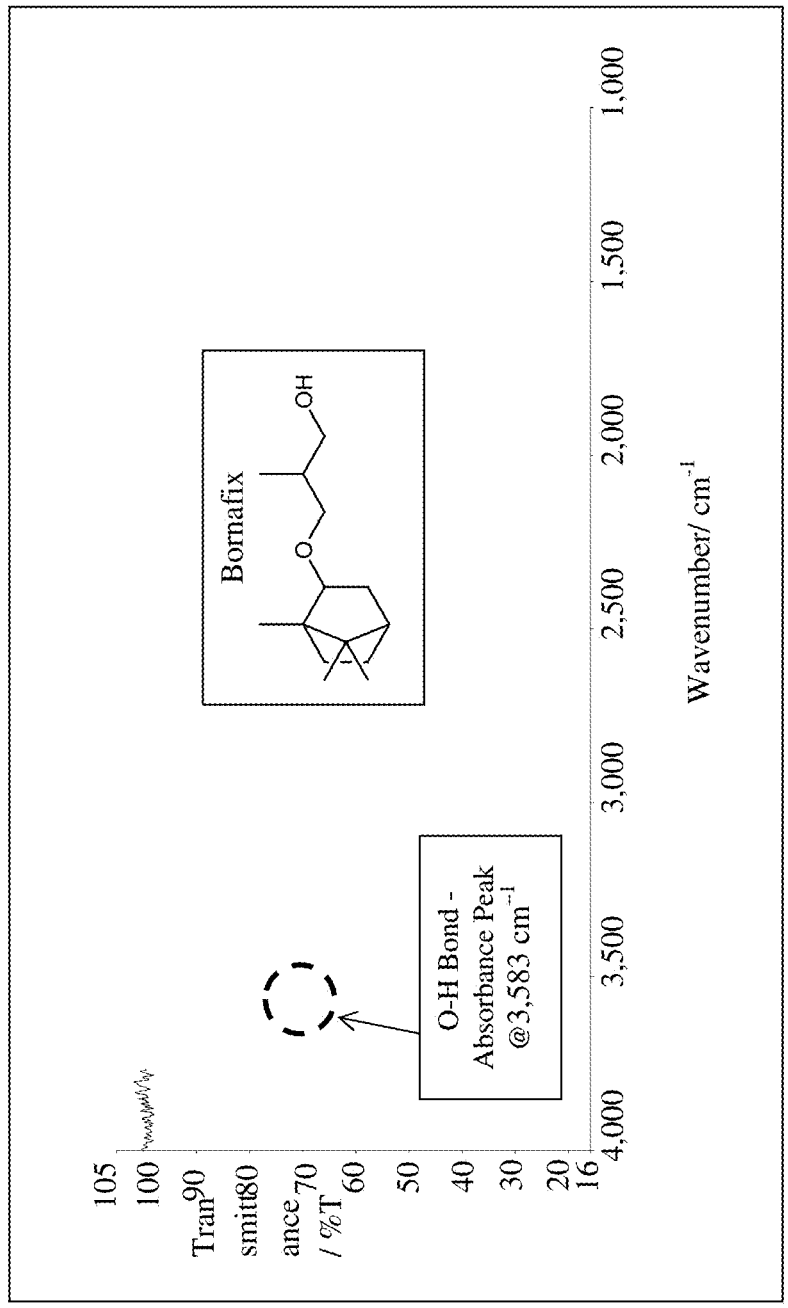
Figure 3 – Gas-Phase Infrared (IR) Spectrum of Bornafix at 100°C (8 metres)

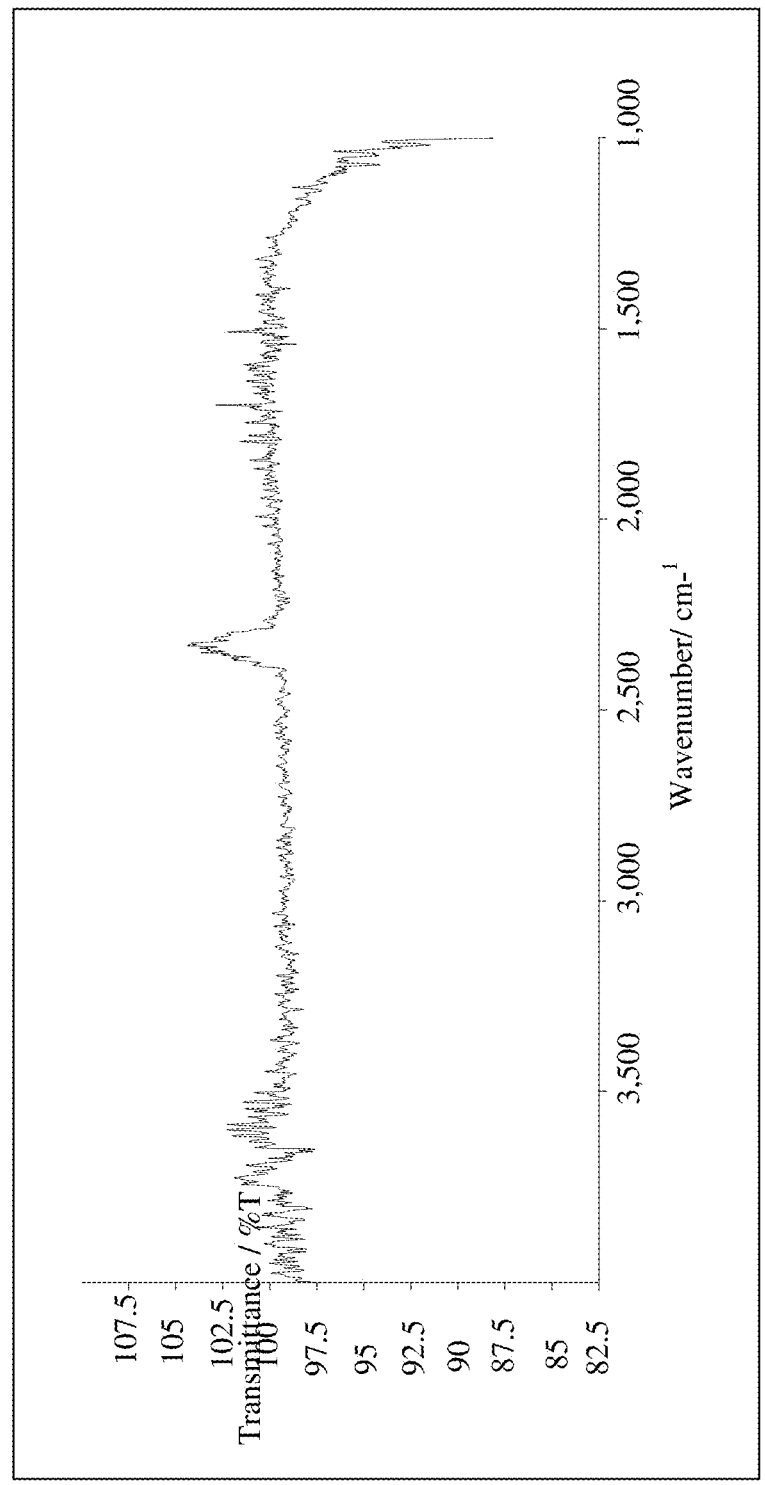
Figure 4 – Gas-Phase Infrared (IR) Spectrum of an Evacuated Cell

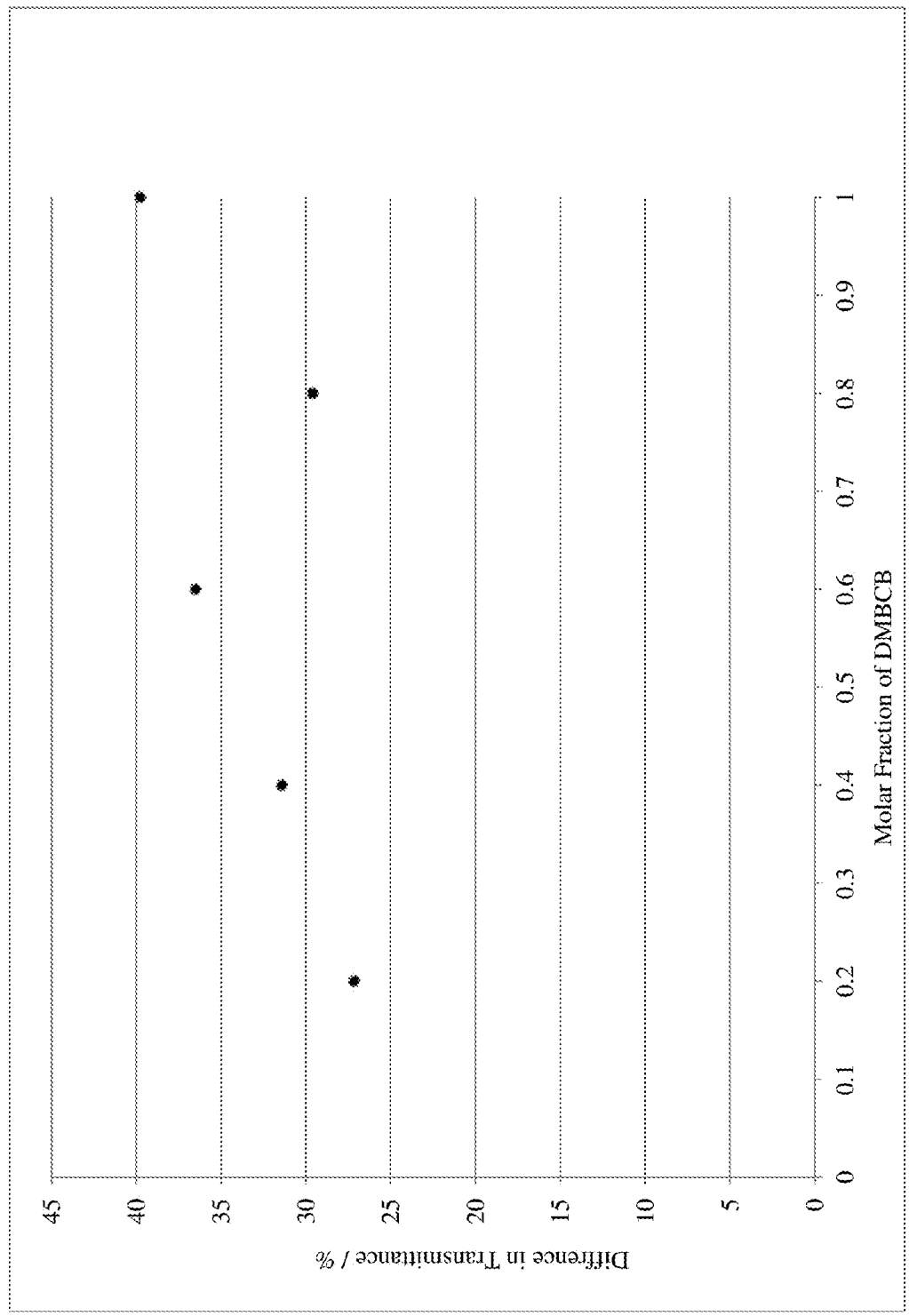

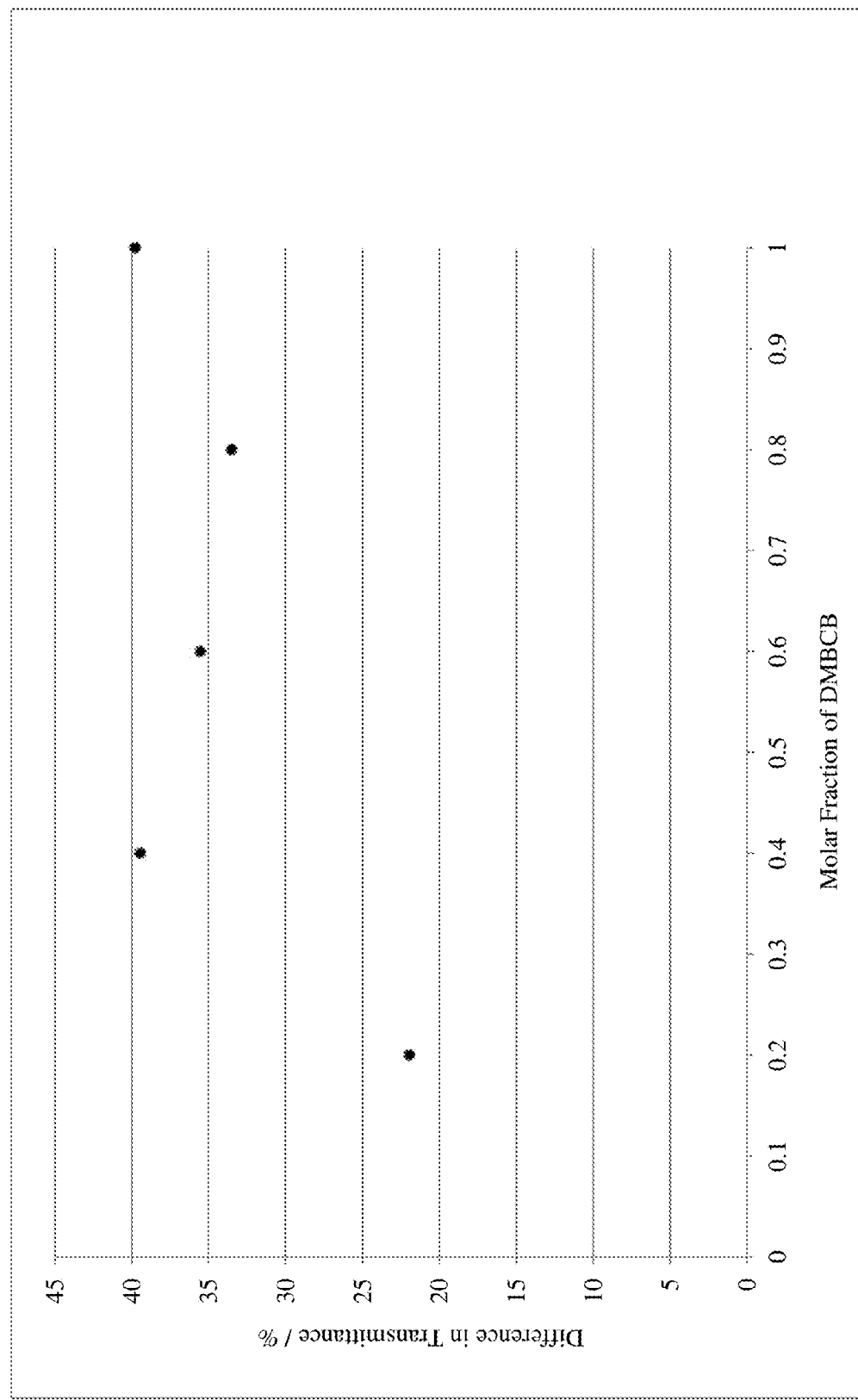

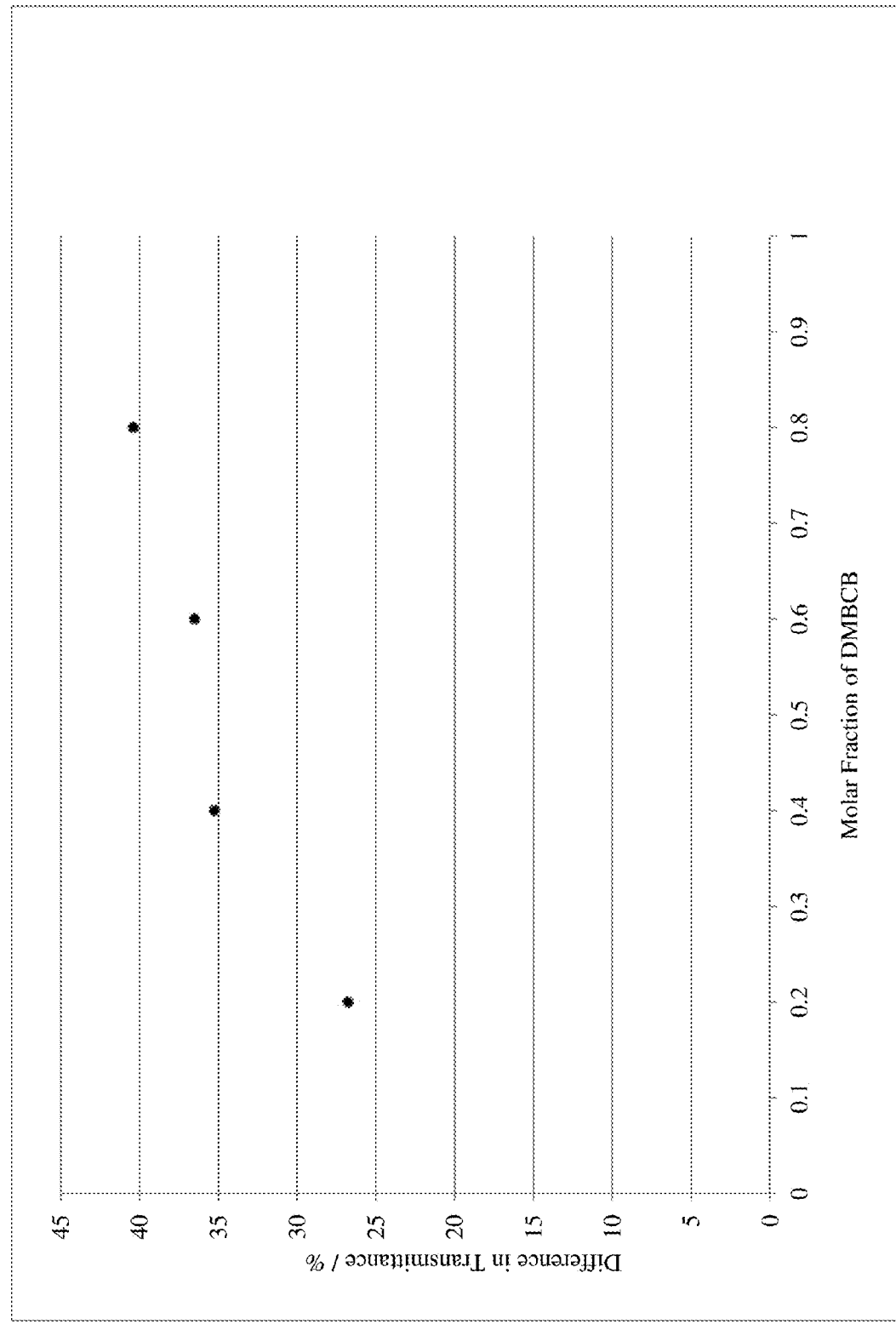

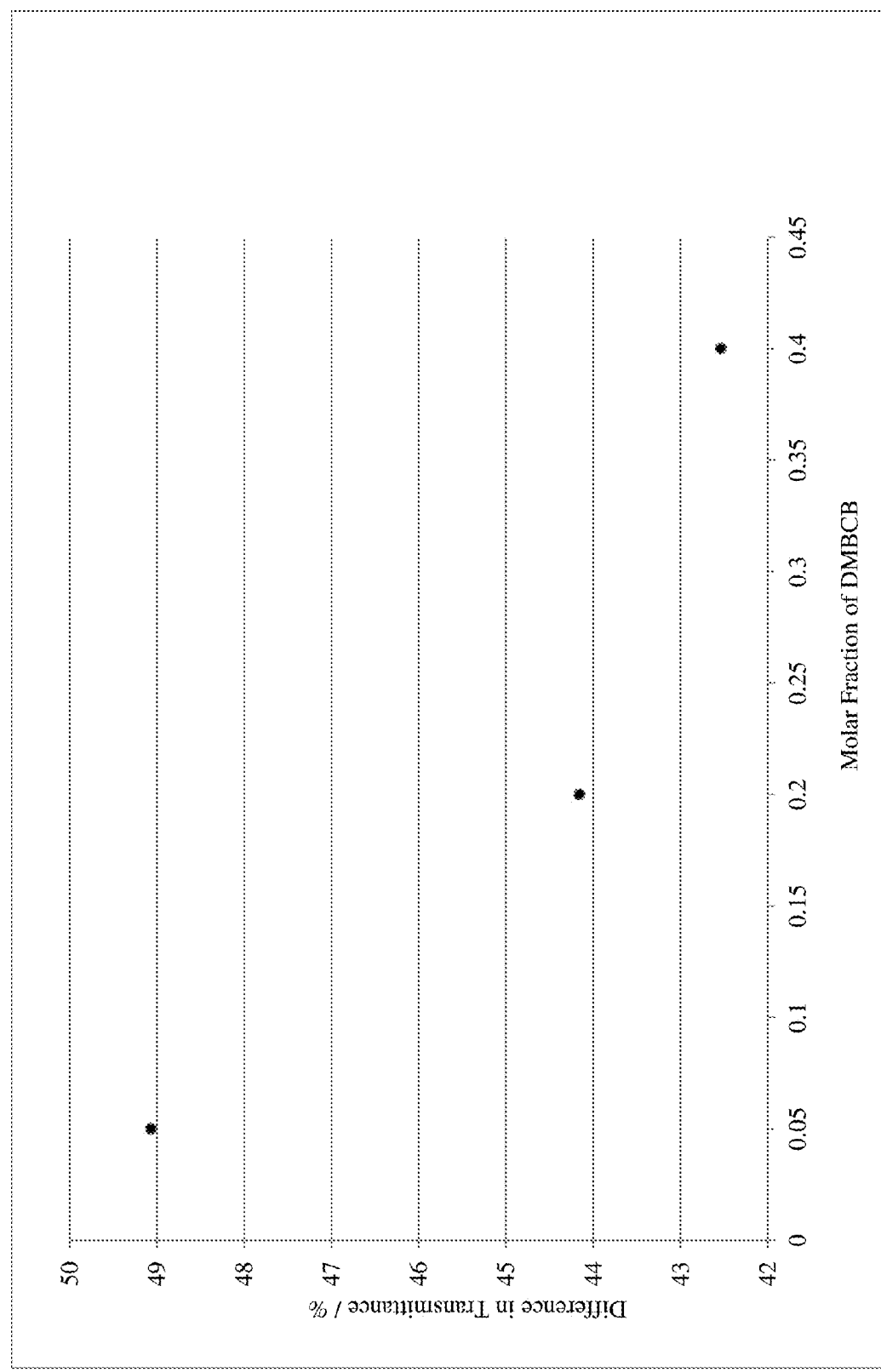
Figure 8 – Gas-Phase Infrared (IR) Peak Height of DMBCB at 45°C, 1,746 cm$^{-1}$ (8 metres)

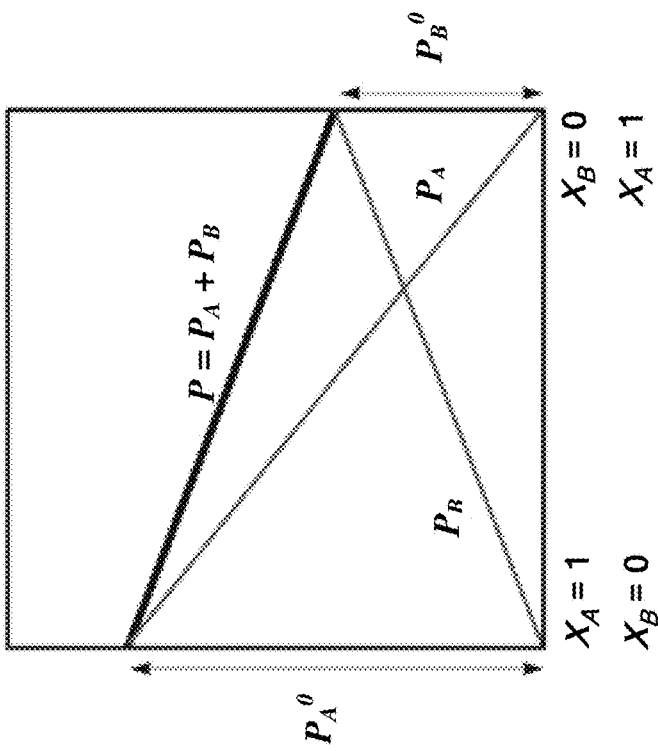
Figure 9 – Total vapour pressure and partial vapour pressures proportional to the mole fractions of the components

FRAGRANCE COMPOSITIONS COMPRISING IONIC LIQUIDS

FIELD OF THE INVENTION

The present invention relates to fragrance compositions comprising ionic liquids. In particular, the fragrance compositions of the present invention have enhanced evaporation of the fragrance component.

BACKGROUND OF THE INVENTION

Perfume raw materials (PRMs) have their own inherent volatility as determined in part by their molecular weight (i.e., size) and in part by the interaction with their surroundings (i.e., ability to hydrogen bond with other PRMs or solvents). The volatility of the PRMs can span a wide range and impact the evaporation rate and/or release of the fragrance components from a composition into headspace (and thus becoming olfactorily noticeable). For example, highly volatile PRMs (i.e., greater than about 0.1 Torr (>0.013 kPa) at 25° C.), which tend to smell citrusy, green, light and fresh, may be noticeable for only a few minutes after being applied to a substrate. Less volatile PRMs (i.e., between about 0.1 to about 0.003 Torr (0.013 to 0.00040 kPa) at 25° C.), characterised by floral or fruity notes, may be detectable for several hours. The least volatile PRMS (i.e., less than about 0.003 Torr (<0.00040 kPa) at 25° C.) are typically heavy florals, sweet, musky and woody, and can last for several days. Although it may be acceptable in some situations to have fragrances remain on the applied substrate for long periods (e.g., fabrics to be stored in cupboard for days or weeks before use), generally, this is not suitable for many fragrance compositions.

Typically, consumers will use a fragrance composition (e.g., fine fragrance, deodorant, body lotion, etc.) and then remove it from their skin after a period of 8 to 24 hours. Indeed, consumers may actually wish to use another, differently scented product, in a shorter time frame than in between showering/bathing. Currently, consumers are either forced to mix a new scent with an old scent, if the old one has not completely evaporated, or alternatively remove the old scent by washing it off their skin. This provides an unpredictable or undesirable scent experience for users. Moreover, even though the old scent can be removed by washing, it represents a significant waste of product as "unused" product (and its accompanying scent) is washed down the drain. In fact, some consumers view the premature removal of the old scented product as being both costly and environmentally unfriendly.

Further, the possible types of fragrance profiles or characters to date have been somewhat limited due to the volatility of the PRMs. If perfumers wanted to design a fragrance with PRMs that evaporate in a given time frame applicable for personal care applications (i.e., 1 to 12 hours after application), then they would be restricted to the highly volatile PRMs characters (e.g., citrusy, green, light and fresh). They would be unable to create fragrance profiles derived from the less or least volatile PRM characters (e.g., heavy florals, spicy, sweet and musky notes). Thus, it is advantageous to be able to create fragrance compositions that span a wider range of fragrance characters while still having all or substantially all of the PRMs evaporated within a given time frame (i.e., 1 to 12 hours after application).

Recently, ionic liquids have been used in the fragrance industry for dealing with solvent applications of the synthesis of fragrance materials or with the extractions of naturally derived PRMs (Sullivan, N., *Innovations in Pharma. Tech.* 2006, 20:75-77). For example, Forsyth et al. investigated the utilisation of ionic liquid solvents for the synthesis of lily-of-the-valley fragrance and fragrance intermediate Lilial (Forsyth et al., *J. Mol. Cat. A.* 2005, 231:61-66). Additionally, the utilisation of ionic liquids to suppress evaporation of fragrances in consumer products has also been gaining attention (Davey P., *Perfumer Flavorist* 2008, 33(4):34-35). For instance, ionic liquids have been used as "fixatives" with fragrance compositions to delay the rate of evaporation of the perfume component to impart increased stability/longevity of the fragrance (Petrat et al., US2006/0166856). Ionic liquids have also been used as pro-fragrances where PRM is appended covalently to either the cation or the anion (Rogers et al., US2012/046244; Blesic et al., RSC Advances, 2013, 3:329-333).

Accordingly, as discussed above, the prior art efforts have focussed only on delaying the evaporation of PRMs through the use of ionic liquids. As such, the prior art still has limitations, and does not adequately teach how to use ionic liquids in fragrance compositions for enhancing evaporation of PRMs. Therefore, there remains a need for a fragrance composition that comprises ionic liquids to control in a targeted manner, increases in the evaporation and/or release of PRMs from the fragrance composition. There is also a need for a fragrance composition that has a substantial proportion of the PRMs evaporated within a given time frame (i.e., 1 to 24 hours after application).

SUMMARY OF THE INVENTION

In a first aspect, the present invention is directed to a fragrance composition comprising (a) from 0.001% to 99.9% by weight of the total fragrance composition of a perfume raw material, wherein the perfume raw material displays a positive deviation from Raoult's Law; and (b) from 0.01% to 99% by weight of the total fragrance composition of at least one ionic liquid comprising: (i) an anion; and (ii) a cation; wherein the ionic liquid is a liquid at temperatures lower than 100° C., preferably at ambient temperature. Preferably, the perfume raw material displays a positive deviation from Raoult's Law as determined by the D2879:2010 Standard Test Method ("ASTM D2879 Isoteniscope Method") or by the Infrared Gas-Phase Spectroscopy Method described herein.

In another aspect of the present invention, a fragrance composition comprising an ionic liquid as provided herein and at least one low volatility perfume raw material having a vapour pressure less than 0.003 Torr (<0.00040 kPa) at 25° C. and the low volatility perfume raw material is present in an amount from 0.001 wt % to 99.9 wt %, preferably from 0.01 wt % to 99 wt %, relative to the total weight of the perfume raw materials. Preferably, the fragrance composition comprises at least 2, 3, 4, 5, 6 or more low volatility PRMs.

In still another aspect of the present invention, use of fragrance compositions according to the present invention in various products, preferably for personal care applications, and to the preparation thereof. In yet still another aspect of the present invention, a method for treating a targeted substrate using the fragrance composition is provided. These, and other features of the present invention, will become apparent to one skilled in the art upon review of the following detailed description when taken in conjunction with the appended claims.

BRIEF DESCRIPTION OF THE DRAWINGS

While the specification concludes with claims particularly pointing out and distinctly claiming the invention, it is believed that the invention will be better understood from the following description of the accompanying figures wherein:

FIG. 1 provides a Gas-Phase Infrared ("IR") spectrum for dimethyl benzyl carbinyl butyrate ("DMBCB") at 45° C., with a path length of 8 meters and an analytical region between 4,000 and 1,000 cm$^{-1}$ according to the Gas-Phase Infrared Spectroscopy Method.

FIG. 2 provides a Gas-Phase IR spectrum for Nectaryl at 45° C., with a path length of 8 meters and an analytical region between 4,000 and 1,000 cm$^{-1}$ according to the Gas-Phase Infrared Spectroscopy Method.

FIG. 3 provides a Gas-Phase IR spectrum for Bornafix at 45° C., with a path length of 8 meters and an analytical region between 4,000 and 1,000 cm$^{-1}$ according to the Gas-Phase Infrared Spectroscopy Method.

FIG. 4 provides a Gas-Phase IR spectrum for an evacuated cell according to the Gas-Phase Infrared Spectroscopy Method.

FIG. 5 provides a Gas-Phase IR peak height of Example 3a PRM DMBCB at 1,746 cm$^{-1}$ at 45° C. (8 meters).

FIG. 6 provides a Gas-Phase IR peak height of Example 3b PRM DMBCB at 1,746 cm$^{-1}$ at 45° C. (8 meters).

FIG. 7 provides a Gas-Phase IR peak height of Example 3c PRM DMBCB at 1,746 cm$^{-1}$ at 45° C. (8 meters).

FIG. 8 provides a Gas-Phase IR peak height of Example 3d PRM DMBCB at 1,746 cm$^{-1}$ at 45° C. (8 meters).

FIG. 9 shows the total vapour pressure and the partial vapour pressures are proportional to the mole fractions of the components.

DETAILED DESCRIPTION OF THE INVENTION

Definitions

As used herein, articles such as "a" and "an" when used in a claim, are understood to mean one or more of what is claimed or described.

As used herein, the terms "include", "includes" and "including" are meant to be non-limiting.

As used herein, the term "Bornafix" refers to the PRM having the chemical name 1-propanol, 2-methyl-3-[(1,7,7-trimethylbicyclo[2.2.1]hept-2-yl)oxy]- and structure:

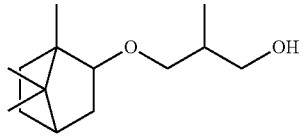 [SMILES: CC(CO)COC1CC2CCC1(C)C2(C)C]

As used herein, the term "dimethyl benzyl carbinyl butyrate" ("DMBCB") refers to the PRM having the chemical name 2-methyl-1-phenylpropan-2-ylbutanoate and structure:

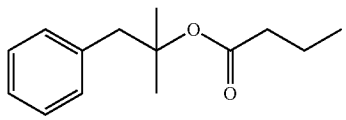 [SMILES: CCCC(=O)OC(C)(C)Cc1ccccc1]

As used herein, the term "Nectaryl" refers to the PRM having the chemical name cyclopentanone, 2-[2-(4-methyl-3-cyclohexen-1-yl)propyl]- and structure:

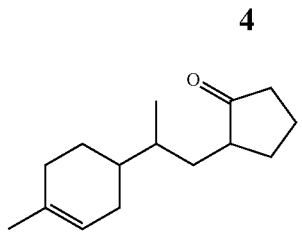

As used herein, the term "consumer" means both the user of the fragrance composition and the observer nearby or around the user.

As used herein, the term "fragrance composition" includes a stand alone product such as, for example, a fine fragrance composition intended for application to a body surface, such as for example, skin or hair, i.e., to impart a pleasant odour thereto, or cover a malodour thereof. The fine fragrance compositions are generally in the form of perfume concentrates, perfumes, eau de parfums, eau de toilettes, aftershaves, colognes, body splashes, or body sprays. The fine fragrance compositions may be ethanol based compositions. The term "fragrance composition" may also include a composition that can be incorporated as part of another product such as, for example, a cosmetic composition which comprises a fragrance material for the purposes of delivering a pleasant smell to drive consumer acceptance of the cosmetic composition. Additional non-limiting examples of "fragrance composition" may also include facial or body powder, foundation, body/facial oil, mousse, creams (e.g., cold creams), waxes, sunscreens and blocks, deodorants, bath and shower gels, lip balms, self-tanning compositions, masks and patches.

As used herein, the term "fragrance profile" means the description of how the fragrance is perceived by the human nose at any moment in time. The fragrance profile may change over time. It is a result of the combination of the PRMs, if present, of a fragrance composition. A fragrance profile is composed of 2 characteristics: 'intensity' and 'character'. The 'intensity' relates to the perceived strength whilst 'character' refers to the odour impression or quality of the perfume, i.e., fruity, floral, woody, etc.

As used herein, the terms "perfume" refers to the component in the fragrance composition that is formed of perfume raw materials, i.e., ingredients capable of imparting or modifying the odour of skin or hair or other substrate.

As used herein, the term "perfume raw material" ("PRM") and "perfume raw materials" ("PRMs") relates to a perfume raw material, or a mixture of perfume raw materials, that are used to impart an overall pleasant odour or fragrance profile to a fragrance composition. "Perfume raw materials" can encompass any suitable perfume raw materials for fragrance uses, including materials such as, for example, alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also know for use as "perfume raw materials". The individual perfume raw materials which comprise a known natural oil can be found by reference to Journals commonly used by those skilled in the art such as "Perfume and Flavourist" or "Journal of Essential Oil Research", or listed in reference texts such as the book by S. Arctander, *Perfume and Flavor Chemicals*, 1969, Montclair, N.J., USA and more recently re-published by Allured Publishing Corporation Illinois (1994). Additionally, some perfume raw materials are supplied by the fragrance houses (Firmenich, International Flavors & Fragrances, Givaudan, Symrise) as mixtures in the form of proprietary speciality accords. Non-limiting examples of the perfume raw materials useful herein include pro-fragrances such as acetal pro-fragrances, ketal pro-fragrances, ester pro-fragrances, hydrolisable inorganic-organic pro-fragrances, and mixtures thereof. The perfume raw materials may be released from the pro-fragrances in a number of ways. For example, the fragrance may be released as a result of simple hydrolysis, or by a shift in an equilibrium reaction, or by a pH-change, or by enzymatic release or by thermal change or by photo-chemical release.

As used herein, the term "Raoult's Law" refers to the behaviour of the vapour pressure of the components of an ideal solution (Atkins, P. W. and Paula, J. D., *Atkins' Physical Chemistry*, $9^{th}$ Edit. (Oxford University Press Oxford, 2010). In an "ideal solution" the interaction between the different chemical species of the solution are the same as the self-interaction within the chemical species such that when the solution is formed the enthalpy of mixing is zero. An ideal solution will follow "Raoult's Law" such that the total vapour pressure and the partial vapour pressures are proportional to the mole fractions of the components, as shown in the graph in FIG. 9 for a 2-component system wherein $$P = \sum_i P_i = \sum_i P_i^o X_i$$

where: $P_i^o$=Vapour pressure of the pure component i
$X_i$=Mole fraction the component i in the mixture
$X_A$=Mole fraction of material A
$X_B$=Mole fraction of material B
$P_A$=Partial pressure of A
$P_B$=Partial pressure of B The partial pressure of each component, $P_i$, is equal to the pressure of the pure component, $P_i^o$, multiplied by its mole fraction, $X_i$. Ideal mixtures, that therefore by definition obey Raoult's Law, are usually mixtures of materials with nearly identical structures and properties.

When mixtures do not follow Raoult's Law, they are termed non-ideal solutions. The activity coefficient, $\gamma$, describes the degree of deviation from ideality. The activity coefficient for component i at a mole fraction on X is described as:

$\gamma_{iX} = P_{iX}/(P_{iX})_{ideal}$ $\gamma_{iX} = P_{iX}/(X_i P_i^o)$ where $P_{iX}$ is the measured partial vapour pressure over a solution of PRM i at mole fraction X and $(P_{iX})_{ideal}$ is the calculated ideal partial vapour pressure based on the mole fraction $X_i$ and the measured vapour pressure of the pure component $P_i^o$.

Alternatively the activity coefficient, $\gamma$, can also be determined by the concentrations in the gas-phase wherein, $\gamma_{iX} = c_{iX}/(c_{iX})_{ideal}$ $\gamma_{iX} = c_{iX}/(X_i c_i^o)$ where $c_{iX}$ is the measured concentration over a solution of PRM i at mole fraction X and $C_{iXideal}$ is the calculated ideal concentration based on the mole fraction $X_i$ and the measured concentration of the pure component $c_i^o$.

In addition, when relative concentrations (rc) rather than absolute gas-phase concentrations are measured, as with Infrared Gas-Phase Spectroscopy, the absolute concentrations can be substituted for relative concentration into the equation above, so that $\gamma_{iX} = rc_{iX}/(X_i rc_i^o)$ For ideal solutions, $\gamma=1$. Non-ideality can result in two alternative vapour pressure behaviours: (i) negative deviation from Raoult's Law (i.e., $\gamma<1$), wherein the vapour pressure is lower than that predicted for ideal behaviour or (ii) positive deviation from Raoult's Law (i.e., $\gamma>1$) wherein the vapour pressure is higher than predicted for ideal behaviour.

The present invention is directed at ionic liquids that when formulated into a fragrance composition will give rise to a positive deviation from Raoult's Law for one or more of the PRMs for which the activity coefficient, $\gamma$, is greater than 1 at one of the mole fractions between 0.05 and 0.8 of the PRM.

Without wishing to be bound by theory, a positive deviation from Raoult's Law may indicate dissimilarities of polarity and/or structure between the PRMs and the ionic liquid leading the PRMs to escape the liquid phase more easily and go into the headspace. When this happens, the vapour pressure of the resultant mixture will be greater than expected from Raoult's Law and thus show a positive deviation from the ideal solution behaviour, wherein the activity coefficient, $\gamma$, is greater than 1.

The positive deviation can be determined as follows:
1. Determine the pure PRM vapour pressure $P_i^o$ or the pure PRM relative gas-phase concentration, $rc_i^o$.
2. Calculate Raoult's Law ideal PRM vapour pressure $(P_{iX})_{ideal}$ or the ideal PRM relative gas-phase concentration $(c_{iX})_{ideal}$ at different PRM mole fractions (e.g., $X_i=0.05, 0.2, 0.4, 0.6,$ or $0.8$).
3. Measure the PRM vapour pressure $P_{iX}$ or relative gas-phase concentration $rc_{iX}$ at different mole fractions (e.g., $X_i=0.05, 0.2, 0.4, 0.6,$ or $0.8$).
4. Determine the activity coefficient $(\gamma_i)$ at different mole fractions (e.g., $X_i=0.05, 0.2, 0.4, 0.6,$ or $0.8$) according to the equation above.
5. A PRM is deemed to have a positive deviation if any of the activity coefficients are greater than 1 for any of the mole fractions (e.g., $X_i=0.05, 0.2, 0.4, 0.6$ or $0.8$) of the PRM.

Whereby, the vapour pressures of a PRM can be measured by the ASTM D2879:2010 Standard Test Method ("ASTM D2879 Isoteniscope Method") for Vapour Pressure-Temperature Relationship and Initial Decomposition Temperature of Liquids by Isoteniscope with the variations as described herein the Method section. Alternatively, the vapour pressure can also be measured using the vapour pressure apparatus described in Husson et al., *Fluid Phase Equilibria* 294 (2010) pp. 98-104. Without wishing to be bound by theory, since ionic liquids exhibit effectively zero vapour pressure at room temperature, the measured vapour pressure is the vapour pressure of the volatile components (i.e., PRMs) and therefore for systems with only one volatile component these approaches measure the vapour pressure of the PRM.

However, water may be present in either the ionic liquid or the PRM, and hence can also contribute to the vapour pressure measured by the methods above. This issue can be mitigated by throughly drying both the ionic liquid and PRM using standard techniques known in the art as described in the methods section herein. In addition, a correction factor may be applied to the measured vapour pressure to remove the portion of the vapour pressure that is attributable to water present in the ionic liquid. This measurement is then taken as the vapour pressure of the pure ionic liquid, since this is the vapour pressure due to the presence of water in the ionic liquid, proportional to the molar fraction of ionic liquid in the sample under consideration, as explained in the methods section.

Preferably, an alternative method that can determine the relative gas-phase concentrations of particular components involves the use of infrared ("IR") spectroscopy. In particular, the infrared spectroscopy of the gas-phase is such a method that will distinguish between the chemicals in a simple multi-component system, in this case water and PRM. Molecules absorb specific frequencies of the electromagnetic spectrum that are characteristic of their structures. This technique is typically used to study organic compounds using radiation in the mid-IR range of 4,000-400 cm$^{-1}$. This provides a well defined fingerprint for a given molecule where IR light absorbance (or transmittance) is plotted on the vertical axis vs. frequency on the horizontal axis, in units of reciprocal centimeters (cm$^{-1}$), or wavenumbers. Additionally to the materials contained in the enclosed headspace of the cell, atmospheric carbon dioxide is detected by the IR beam externally to the cell.

A gas-phase IR cell with heating jacket enables us to create a closed headspace at equilibrium at a specific temperature. The IR spectrometer scans the headspace and provides the fingerprint of the gaseous mixture. Specific peaks at particular wavenumbers in the spectra can be identified as typical of the components, as described in the method. The absorbance at a particular wavenumber is proportional to the gas-phase concentration, and hence vapour pressure, of the specific component identified at that wavenumber. The relative concentration is obtained by normalising the absorbance at a particular wavenumber for a given sample versus the absorbance at that same wavenumber for the pure PRM.

If quantification is desirable, then it can be achieved by adding a known very small quantity of the volatile material (e.g., PRM), to the gas cell and taking the spectra at a temperature where all the volatile material is in the gas phase. This will then enable conversion between relative and absolute gas-phase concentrations. However, for the purposes of calculating the activity coefficient, as described above, this is not necessary as the activity coefficient is itself a ratio of concentrations.

As used herein, and unless defined otherwise, the term "vapour pressure" or "VP" means the pressure in a vacuum of the vapour in equilibrium with its condensed phase at a defined temperature for a given chemical species. It defines a chemical species' propensity to be in the gas phase rather than the liquid or solid state. The higher the vapour pressure, the greater the proportion of the material that will, at equilibrium, be found in the gas-phase in a closed headspace. It is also related to the rate of evaporation of a perfume raw material in an open environment where material is leaving the system. Unless defined otherwise, the pure vapour pressure of a single material is calculated according to the reference program Advanced Chemistry Development (ACD/Labs) Software Version Version 14.02 (or preferably the latest version update).

As used herein, and unless defined otherwise, the term "relative gas-phase concentration" means the relative concentration in a vacuum of the vapour in equilibrium with its condensed phase at a defined temperature for a given chemical species. It defines a chemical species' propensity to be in the gas phase rather than the liquid or solid state. The higher the relative gas-phase concentration, the greater the proportion of the material that will, at equilibrium, be found in the gas-phase in a closed headspace. It is also related to the rate of evaporation of a perfume raw material in an open environment where material is leaving the system.

Certain chemical functional groups named here are preceded by a shorthand notation indicating the total number of carbon atoms that are to be found in the indicated chemical group. For example: $C_1$-$C_{20}$ alkyl describes an alkyl group having a total of 1 to 20 carbon atoms (e.g. $C_{10}$ implies $C_{10}H_{21}$). The total number of carbons in the shorthand notation does not include carbons that may exist in substituents of the group described. Unless specified to the contrary, the following terms have the following meaning:

"Amino" refers to the —$NH_2$ functional group.

"Azido" refers to the —$N_3$ functional group.

"Cyano" refers to the —CN functional group.

"Halo" refers to fluoro, chloro, bromo, or iodo.

"Halide" refers to a halide atom bearing a negative charge such as for example, fluoride (F$^-$), chloride (Cl$^-$), bromide (Br$^-$), or iodide (I$^-$).

"Hydroxyl" refers to the —OH functional group.

"Nitro" refers to the —$NO_2$ functional group.

"Oxo" refers to the =O substituent.

"Alkyl" refers to a group containing a straight or branched hydrocarbon chain consisting solely of carbon and hydrogen atoms, containing no unsaturation, having from 1 to 20 carbon atoms, preferably 1 to 12 carbon atoms, preferably 1 to 8, or preferably 1 to 6 carbon atoms, and which is attached to the rest of the molecule by a single bond, e.g., methyl, ethyl, propyl, 1-methylethyl (iso-propyl), butyl, pentyl, and the like. An alkyl may be optionally substituted.

"Alkenyl" refers to a group containing straight or branched hydrocarbon chain consisting solely of carbon and hydrogen atoms, containing at least one carbon-carbon double bond, having from 2 to 20 carbon atoms, preferably 2 to 12 carbon atoms, or preferably 1 to 8 carbon atoms, e.g., ethenyl, prop-2-enyl, but-1-enyl, pent-1-enyl, penta-1,4-dienyl, and the like. An alkenyl may be optionally substituted.

"Alkynyl" refers to a group containing straight or branched hydrocarbon chain consisting solely of carbon and hydrogen atoms, containing at least one carbon-carbon triple bond, having from 2 to 20 carbon atoms, preferably 2 to 12 carbon atoms, or preferably 1 to 8 carbon atoms, e.g., ethynyl, propynyl, butynyl, pentynyl, hexynyl, and the like. An alkynyl may be optionally substituted.

"Alkylene" or "alkylene chain" refers to a group containing straight or branched hydrocarbon chain linking the rest of the molecule to a group, consisting solely of carbon and hydrogen, containing no unsaturation and having from 1 to 12 carbon atoms, e.g., methylene, ethylene, propylene, butylene, and the like. An alkylene may be optionally substituted.

"Alkenylene" or "alkenylene chain" refers to a straight or branched hydrocarbon chain linking the rest of the molecule to a group, consisting solely of carbon and hydrogen, containing at least one carbon-carbon double bond and having from 2 to 20 carbon atoms, preferably 2 to 12 carbon atoms, e.g., ethenylene, propenylene, butenylene, and the like. An alkenylene may be optionally substituted.

"Alkynylene" or "alkynylene chain" refers to a straight or branched hydrocarbon chain linking the rest of the molecule to a group, consisting solely of carbon and hydrogen, containing at least one carbon-carbon triple bond and having from 2 to 20 carbon atoms, e.g., propynylene, butynylene, and the like. An alkynylene may be optionally substituted.

"Alkoxy" refers to a functional group of the formula —$OR_a$ where $R_a$ is an alkyl chain as defined above containing 1 to 20 carbon atoms, preferably 1 to 12 carbon atoms. An alkoxy may be optionally substituted.

"Alkoxyalkyl" refers to a functional group of the formula —$R_{a1}$—O—$R_{a2}$ where $R_{a1}$ is an alkylene as defined above and $R_{a2}$ is an alkyl chain as defined above containing 1 to 20 carbon atoms, preferably 1 to 12 carbon atoms. An alkoxyalkyl may be optionally substituted.

"Oligo-alkoxyalkyl" refers to a functional group containing more than two oxygen atoms that are separated by a straight or branched alkyl chain as defined above containing at least 2 or more carbon atoms, e.g., etherated alkyl chains. An oligo-alkoxyalkyl may be optionally substituted.

"Aryl" refers to aromatic monocyclic or multicyclic hydrocarbon ring system consisting only of hydrogen and carbon, and preferably containing from 6 to 18 carbon atoms, preferably 6 to 10 carbon atoms, where the ring system is aromatic (by the Hückel definition). Aryl groups include but are not limited to groups such as phenyl, naphthyl, anthracenyl. The term "aryl" or the prefix "ar" (such as in "aralkyl") is meant to include aryls that may be optionally substituted.

"Arylene" refers to a linking aryl group, and where the aryl is as defined above.

"Cycloalkyl" refers to a stable saturated mono-cyclic or polycyclic hydrocarbon group consisting solely of carbon and hydrogen atoms, which may include fused or bridged ring systems, having from 3 to 15 carbon atoms, preferably having from 3 to 10 carbon atoms or preferably from 3 to 7 carbon atoms. A cycloalkyl may be optionally substituted.

"Cycloalkylalkyl" refers to a functional group of the formula —$R_aR_d$, where $R_a$ is an alkylene as defined above and $R_d$ is a cycloalkyl as defined above.

"Haloalkyl" refers to an alkyl as defined above that is substituted by one or more halogen groups, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. A haloalkyl may be optionally substituted.

"Heterocyclyl" refers to a stable 3- to 24-membered saturated ring which consists of 2 to 20 carbon atoms and from 1 to 6 heteroatoms selected from atoms consisting of nitrogen, oxygen, or sulfur. Unless stated otherwise specifically in the specification, the heterocyclyl may be a monocyclic, bicyclic, tricyclic or tetracyclic ring system, which may include fused or bridged ring systems; and the nitrogen, carbon or sulfur atoms in the heterocyclyl may be optionally oxidised; the nitrogen atom may be optionally quaternised. A heterocyclyl may be optionally substituted.

"Heterocyclylalkyl" refers to a functional group of the formula —$R_aR_e$ where $R_a$ is an alkylene as defined above and $R_e$ is a heterocyclyl as defined above, and if the heterocyclyl is a nitrogen-containing heterocyclyl, the heterocyclyl may be attached to the alkylene at the nitrogen atom. A heterocyclylalkyl may be optionally substituted.

"Heteroaryl" refers to a 5- to 20-membered aromatic ring which consists of 1 to 17 carbon atoms and from 1 to 3 heteroatoms selected from atoms consisting of nitrogen, oxygen and sulfur. The heteroaryl may be a monocyclic, bicyclic, tricyclic or tetracyclic ring system, which may include fused or bridged ring systems. A heteroaryl may be optionally substituted.

"Heteroarylalkyl" refers to a functional group of the formula —$R_aR_f$ where $R_a$ is an alkylene as defined above and $R_f$ is a heteroaryl as defined above. A heteroarylalkyl may be optionally substituted.

"Heteroarylene" refers to a linking heteroaryl group and where the heteroaryl is as defined above. A heteroarylene may be optionally substituted.

"Optionally substituted" means that the subsequently described event of circumstances may or may not occur and that the description includes instances where the event or circumstance occurs and instances in which it does not. For example, unless specified otherwise, "optionally substituted" means that the chemical moiety may or may not be substituted by one or more of the following groups: alkyl, alkenyl, halo, haloalkenyl, cyano, nitro, aryl, cycloalkyl, heterocyclyl, heteroaryl, oxo, —$OR^{10}$, —OC(O)—$R^{10}$, —N($R^{10}$)$_2$, —C(O)$R^{10}$, —C(O)O$R^{10}$, —C(O)N($R^{10}$)$_2$, —N($R^{10}$)C(O)O$R^{12}$, —N($R^{10}$)C(O)$R^{12}$, —N($R^{10}$)S(O)$_t R^{12}$ (where t is 1 to 2), —S(O)$_t$O$R^{12}$ (where t is 1 to 2), —S(O)$_x R^{12}$ (where x is 0 to 2) and —S(O)$_t$N($R^{10}$)$_2$ (where t is 1 to 2) where each $R^{10}$ is independently hydrogen, alkyl, haloalkyl, cycloalkyl, cycloalkylalkyl, aryl (optionally substituted with one or more halogen groups), aralkyl, heterocyclyl, heterocyclylalkyl, heteroaryl or heteroarylalkyl; and each $R^{12}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

It is understood that the test methods that are disclosed in the Test Methods section of the present application must be used to determine the respective values of the parameters of the present invention as described and claimed herein.

In all embodiments of the present invention, all percentages are by weight of the total fragrance composition, as evident by the context, unless specifically stated otherwise. All ratios are weight ratios, unless specifically stated otherwise, and all measurements are made at 25° C., unless otherwise designated.

Ionic Liquids

Surprisingly, it has been found that ionic liquids can be used to alter the display of PRMs from a fragrance composition. In particular, the applicants have discovered that fragrance compositions comprising ionic liquids will have increased evaporation of some of the PRMs from a surface in an open system. As a result, more of the PRMs are present in the air directly above the application site shortly after application to a substrate. This may be observed olfactively as some PRMs being perceived as stronger at initial time points (e g., immediately after application, or 1, 2, 3, 4, 5 or 6 hours later). A consequence of this increased evaporation is that PRMs applied to a substrate will become very weak after a shorter period of time (i.e., 6, 8, 10 to 12 hours), as compared to the same fragrance composition absent of the ionic liquids (i.e., 12 to 24 hours and longer). This may be observed as some PRMs being perceived as less long-lasting. In particular, ionic liquids, according to the present invention, appear to aid in targeted increases in the evaporation, preferably the fragrance components derived from the less or least volatile perfume raw materials (i.e., low volatility PRMs), from the fragrance composition.

Preferably, the ionic liquids useful in the present invention exhibit no measurable vapour pressure between 25° C. and 100° C. Thus, it is understood that the ionic liquids themselves make no measurable contribution to the vapour pressure of any mixture in which they are incorporated.

By incorporating the ionic liquids, it is desired that the partial vapour pressure of the individual PRMs of the fragrance composition is increased, as measured by the ASTM D2879 Isoteniscope Method or the vapour pressure apparatus in Husson et al., *Fluid Phase Equilibria*, 294 (2010) pp. 98-104 in a closed system or preferably by the Gas-Phase Infrared Spectroscopy Method. The partial vapour pressure in a closed system is an approximation for the partial vapour pressure close to the application site.

While not wishing to be bound by theory, it is believed that the enhanced partial vapour pressure of the PRMs by the ionic liquids is caused by the repulsion between the heteroatoms of the PRMs and the ionic liquids. Since PRMs are neutral molecules, the dominant mechanism for association between PRMs and ionic liquids will be via hydrogen bond formation. In order to induce a positive deviation from Raoult's Law, the hydrogen bonding between the PRM and the ionic liquid should be minimised. If repulsion between a PRM and ionic liquid is desired, and the PRM contains an alcohol or phenol functional group (i.e., the PRM contains both hydrogen donor and acceptor), then the structure of the ionic liquid should be designed to have certain properties. For example, the ionic liquid should contain no hydrogen bond acceptor sites, or more preferably contain neither hydrogen bond acceptor sites, nor hydrogen bond donor sites. If the PRM contains ether, ketone, aldehyde or ester functional groups (i.e., the PRM contains only donor atom(s), but no hydrogen-bond donor sites), then the ionic liquid should be designed to contain neither hydrogen bond acceptor sites, nor preferably hydrogen bond donor sites. There must be a net repulsive interaction between the ionic liquid and the PRM; hence weak attractive interactions can be tolerated as long as the sum of all the repulsive interactions is greater than the sum of all the attractive interactions.

Thus, the ionic liquids can be designed to repel PRMs, and hence induce changes in the PRMs' vapour pressures as compared to the vapour pressures of an ideal mixture. It is desirable that ionic liquids when incorporated into fragrance compositions of the present invention will result in positive deviations from Raoult's Law, so that the ionic liquids repel the PRMs to enhance their release into the surrounding headspace.

In an embodiment, the PRMs in the fragrance composition comprising the ionic liquids according to the present invention display a positive deviation from Raoult's Law wherein the activity coefficient ("$\gamma$") is greater than 1. In other embodiments, the fragrance composition of the present invention will give rise to a positive deviation from Raoult's Law for one or more of the PRMs for which the activity coefficient $\gamma$>1.05 or 1.10 or 1.15 or 1.20 or 1.25 or 1.30 or 1.35 or 1.40 or 1.45 or 1.50 or 1.55 or 1.60 or 1.65 or 1.70 or 1.75 or 1.80 or 1.85 or 1.90 or 1.95 or 2.00 or 2.10 or 2.20 or 2.30 or 2.40 or 2.50 or 2.60 or 2.70 or 2.80 or 2.90 or 3.00 at a mole fraction between 0.05 and 0.8 of the PRM.

Preferably, the perfume raw material displays the positive deviation from Raoult's Law having an activity coefficient $\gamma$ greater than 1 at a mole fraction between 0.05 and 0.8 of the perfume raw material, preferably at the mole fraction between 0.05 and 0.2, or preferably at the mole fraction between 0.2 and 0.4, or preferably at the mole fraction between 0.4 and 0.6, or preferably at the mole fraction between 0.6 and 0.8 of the perfume raw material.

Preferably, the perfume raw material displays the positive deviation from Raoult's Law having an activity coefficient $\gamma$ greater than 1 is determined by the D2879:2010 Standard Test Method ("ASTM D2879 Isoteniscope Method") and the perfume raw material is present at mole fraction between 0.2 and 0.8 of the perfume raw material.

Preferably, the perfume raw material displays the positive deviation from Raoult's Law having an activity coefficient $\gamma$ greater than 1 is determined by the Gas-Phase Infrared Spectroscopy Method, and the perfume raw material is present at mole fraction between 0.05 and 0.8 of the perfume raw material.

As used herein, the term "ionic liquid" refers to a liquid which consists exclusively of ions and is present in a liquid form at temperatures lower than 100° C., preferably at ambient or room temperature (i.e., from 15° C. to 30° C.). Particularly preferred ionic liquids are suitable for use in fragranced consumer products and have to be chosen so as to exclude an adverse effect in terms of health or ecology on people, nature and the environment. For example, fragrance compositions, such as for example, perfumes, which may come into direct contact with humans preferably have minimal toxic effect. For other selected applications such as deodorants, however, it may be useful if in the fragrance composition, in particular the ionic liquids, there are microbiocidal properties for killing the microorganisms for suppressing malodours.

Ionic liquids have no effective vapour pressure (essentially zero) and may be easy to handle. Their polarity can be readily adjusted so as to be suitable to a wide range of PRMs. Furthermore, ionic liquids are preferably odourless and will not impart an odour of their own when added into the fragrance compositions of the present invention. Particularly preferable ionic liquids are ones where the PRMs are fully miscible to form a single phase liquid. However, if the PRMs are not entirely miscible, or are immiscible, then co-solvents (e.g., triethyl citrate, or others as listed herein below) can be added to aid in the solubility of the PRMs.

Typically, ionic liquids may have high viscosities (i.e., greater than about 1,000 mPa·s) at room temperature. High viscosities can be problematic in formulating the fragrance compositions of the present invention. Therefore, in an embodiment, the present invention is preferably directed to ionic liquids (undiluted with adjuncts, co-solvents or free water) which have viscosities of less than about 1000 mPa·s, preferably less than about 750 mPa·s, preferably less than about 500 mPa·s, as measured at 20° C. In some embodiments, the viscosity of the undiluted ionic liquids are in the range from about 1 mPa·s to about 400 mPa·s, preferably from 1 mPa·s to about 300 mPa·s, and more preferably from about 1 mPa·s to about 250 mPa·s.

The viscosities of the ionic liquids and fragrance compositions containing therein can be measured on a Brookfield viscometer model number LVDVII+ at 20° C., with Spindle S31 at the appropriate speed to measure materials of differing viscosities. Typically, the measurement is performed at speed from 12 rpm to 60 rpm. The undiluted state is prepared by storing the ionic liquids in a desiccator containing a desiccant (e.g. anhydrous calcium chloride) at room temperature for at least 48 hours prior to the viscosity measurement. This equilibration period unifies the amount of innate water in the undiluted samples.

It should be understood that the terms "ionic liquid", "ionic liquids" and "ILs" refer to ionic liquids, ionic liquid composites and mixtures (or cocktails) of ionic liquids. For example, an ionic liquid may be formed from a homogeneous combination comprising one species of anion and one species of cation, or it can be composed of more than one species of cation and/or anion. Thus, an ionic liquid may be composed of more than one species of cation and one species of anion. An ionic liquid may further be composed of one species of cation and more than one species of anion. Finally, an ionic liquid may further be composed of more than one species of cation and more than one species of anion.

In another embodiment of the present invention, the ionic liquids, may be selectively made to be hydrophobic by careful selection of the anions.

In yet another embodiment of the present invention, the ionic liquids (i.e., cation and anion) are essentially free of any of the following chemical elements: antimony, barium, beryllium, bromine, cobalt, chromium, fluorine, iodine, lead, nickel, selenium, or thallium. By "essentially free" it is meant that no cation or anion containing any of the foregoing chemical elements are intentionally added to form the ionic liquids of the present invention.

Preferably, the ionic liquids are essentially free of chemical materials that are prohibited for use in cosmetic products in various countries, such as for example, the European Commission, Health and Consumers, Cosmetics Regulation Annex II—"List of Substances Prohibited in Cosmetics Products" (http://ec.europa.eu/consumers/cosmetics/cosing/index.cfm?fuseaction=search.results&annex_v2=II&search), and the United States Food and Drug Administration List of "Prohibited & Restricted Ingredients" for cosmetic applications (http://www.fda.gov/cosmetics/guidanceregulation/lawsregulations/ucm127406.htm). The fragrance composition preferably has at least one ionic liquid with an anion according to the following structures.

In an embodiment of the invention is the anion of formula (I):

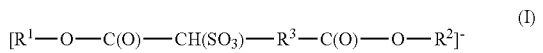

wherein:
R$^1$ and R$^2$ are independently selected from the group consisting of alkyl, mono or oligo-alkoxyalkyl or alkenyl; and
R$^3$ is alkylene, heteroarylene, arylene, or cycloalkylene.

Of this embodiment of the invention are the anion of formula (I) as set forth above wherein:
R$^1$ and R$^2$ are independently selected from alkyl; and
R$^3$ is —(CH$_2$)$_n$— wherein n is an integer of from 1 to 12.

Of this embodiment of the invention, wherein the anion of formula (I) is 1,4-bis(2-ethylhexoxy)-1,4-dioxobutane-2-sulfonate (i.e., AOT, docusate or dioctylsulfosuccinate).

In yet another embodiment of the invention is the anion of formula (II):

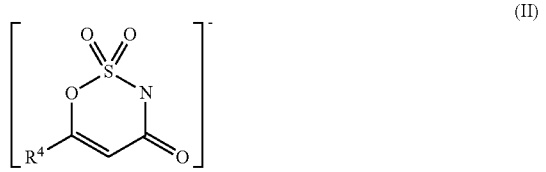

wherein:
R$^4$ is selected from the group consisting of hydrogen, cyano, alkyl, alkoxy and alkoxyalkyl.

Of this embodiment of the invention, wherein the anion of formula (II) is 6-methyl-3,4-dihydro-1,2,3-oxathiazin-4-one 2,2-dioxide (i.e., acesulfame).

In yet another embodiment of the invention is the anion of formula (III):

wherein:
R$^5$ is selected from the group consisting of hydrogen, alkyl, alkenyl, alkynyl, alkoxyalkyl, cycloalkyl, cycloalkylalkyl, aryl, aralkyl, heterocyclyl, heterocyclyalkyl, heteroaryl and heteroarylalkyl.

Of this embodiment of the invention, wherein the anion of formula (III) is methyl sulfonate.

In yet another embodiment of the invention is the anion of formula (IV):

wherein:
R$^9$ is selected from the group consisting of haloalkyl, alkyl and alkenyl.

Of this embodiment of the invention, wherein the anion of formula (IV) is bis {(trifluoromethyl)sulfonyl}amide (i.e. [NTf$_2$]$^-$).

In yet another embodiment of this invention, wherein the anion is independently selected from the group consisting of formulae (I), (II), (III), and (IV) as described above, and combinations thereof. Of this embodiment of the invention, further comprising the anion independently selected from the group consisting of:

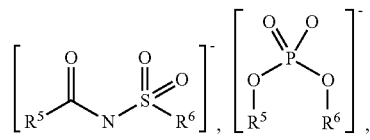

and combinations thereof;
wherein:
each R$^5$ and R$^6$ are independently selected from the group consisting of hydrogen, alkyl, alkenyl, alkynyl, alkoxyalkyl, cycloalkyl, cycloalkylalkyl, aryl, aralkyl, heterocyclyl, heterocyclyalkyl, heteroaryl and heteroarylalkyl.

The preparation of the anions is generally known and can take place, for example, as described in (P. Wasserscheid and T. Welton (Eds.), *Ionic Liquids in Synthesis*, 2$^{nd}$ Edit., Wiley-VCH, 2008). In addition, the alkali metal salts of many anions are also available commercially. Thus, for example, sodium docusate and potassium acesulfame are available from Sigma Aldrich and lithium bistriflamide (LiNTf$_2$) is available from TCI.

The fragrance composition preferably has at least one ionic liquid with a cation according to the following structures.

In an embodiment of the invention, wherein the cation is independently selected from the group consisting of:

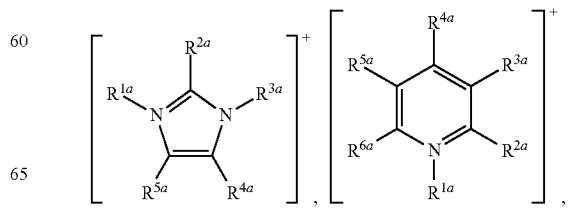

-continued

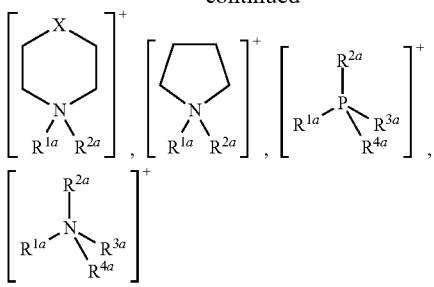

and combinations thereof;
wherein:
X is $CH_2$ or O;
each $R^{1a}$, $R^{3a}$, and $R^{4a}$ are independently selected from hydrogen, $C_1$-$C_{20}$ alkyl, $C_1$-$C_{20}$ alkenyl, $C_1$-$C_{20}$ alkynyl, $C_1$-$C_{20}$ alkoxy, $C_1$-$C_{20}$ alkoxy$C_1$-$C_{20}$alkyl, $C_3$-$C_7$cycloalkyl, $C_3$-$C_7$cycloalkyl$C_1$-$C_4$alkyl, $C_2$-$C_{20}$heterocyclyl, $C_6$-$C_{10}$aryl, $C_6$-$C_{10}$aryl$C_1$-$C_{10}$alkyl, $C_1$-$C_{10}$heteroaryl, halo, halo$C_1$-$C_{20}$alkyl, hydroxyl, hydroxy$C_1$-$C_{20}$alkyl, or —$N(R^{6a})_2$;
each $R^{2a}$ is independently selected from hydrogen, $C_1$-$C_{20}$ alkyl, $C_1$-$C_{20}$ alkenyl, or $C_1$-$C_{20}$ alkynyl;
each $R^{5a}$ is independently selected from hydrogen, $C_1$-$C_{20}$ alkyl, $C_1$-$C_{20}$ alkenyl, $C_1$-$C_{20}$ alkynyl, —$R^{7a}$—$OR^{8a}$, or —$R^{7a}$—$OR^{7a}$—$OR^{8a}$;
each $R^{6a}$ is independently selected from hydrogen, alkyl, alkenyl, alkynyl, halo alkyl, alkoxyalkyl, cyclo alkyl, cycloalkylalkyl, aryl, aralkyl, heterocyclyl, heterocyclyalkyl, heteroaryl, or heteroarylalkyl;
each $R^{7a}$ is independently selected from a direct bond, alkylene chain, alkenylene chain, or alkynylene chain; and
each $R^{8a}$ is independently selected from a hydrogen, alkyl, alkenyl or alkynyl.

Of this embodiment of the invention, wherein the cation is independently selected from the group consisting of 1-butyl-3-methylimidazolium; (N-ethyl-2-(2-methoxyethoxy)-N,N-dimethylethanaminium); 2-(2-ethoxyethoxy)-N-ethyl-N,N-dimethylethanaminium; N-benzyl-N,N-dimethyloctan-1-aminium; N-benzyl-N,N-dimethylnonan-1-aminium and combinations thereof.

The methods for preparing the cations of the present invention are provided in the Examples section. The preparations are not intended to limit the scope of the present invention.

It may be advantageous if the fragrance composition has an ionic liquid which has one or more of the abovementioned salts. It is understood that the ionic liquids can comprise either a single anionic species and a single cationic species or a plurality of different anionic and cationic species. By using different anionic species and/or different cationic species, the properties of the ionic liquids can be matched in an optimal way to the PRMs and/or other components of the fragrance composition. In an embodiment of the invention, the ionic liquids consist of more than one anionic species.

Ionic liquids are formed by combining simple salts of a cation and an anion (e.g. sodium salt of the anion and chloride salt of the cation). Different ionic liquids can be synthesised such that the interactions between the ionic liquids and the solute (i.e., perfume raw materials) are optimised, preferably to provide for a positive deviation from Raoult's Law. Ionic liquids lend themselves to preparation via combinatorial or high-throughput chemistry. Some methods for preparing the ionic liquids of the present invention are provided in the Examples section. The preparations are not intended to limit the scope of the present invention.

Fragrance Compositions

Applicants have surprisingly found that ionic liquids can be added to fragrance compositions to enhance the evaporation of the PRMs from solution. Such enhancement is desirable, for example, to increase the partial pressure and concentration of the PRMs in the headspace. This will result in stronger perfume materials when they are applied to the surface and for initial time points after that. It will also shorten the time frame in which PRMs continue to be detectable in the headspace after application of the fragrance compositions.

Specifically, in one aspect, the present invention provides for a fragrance composition comprising a perfume raw material present with a positive deviation from Raoult's Law in an amount of from about 0.001 wt % to about 99.9 wt %, preferably from about 0.01 wt % to about 90 wt %, preferably from about 0.1 wt % to about 80 wt %, preferably from about 0.2 wt % to about 70 wt %, preferably from about 0.3 wt % to about 60 wt %, preferably from about 0.4 wt % to about 50 wt %, preferably from about 0.5 wt % to about 40 wt %, preferably from about 1 wt % to about 30 wt %, relative to the total weight of the fragrance composition. Further, the perfume raw material comprises at least one low volatility perfume raw material having a vapour pressure <0.003 Torr (<0.00040 kPa) at 25° C.

In another aspect, applicants have surprisingly discovered that by adding ionic liquids in a fragrance composition, the fragrance profile can be improved. For example, by "improved" it is meant that a higher fraction of the PRMs are in the headspace than could be achieved in the absence of ionic liquids. The PRMs would then be olfactively more noticeable (i.e., stronger, and/or more dominant) leading to noteable differences such as, for example, a different concentration profile and new characters, as compared to controls (i.e., compositions containing the PRMs and no ionic liquids).

Typically, it has been very difficult to formulate fragrance profile with an accord made from PRMs having a wide range of volatility, whereby the fragrance profile can be detected sooner after its application versus a control. The present invention will allow perfumers to formulate fragrance composition using PRMs having a wide range of volatility. They can now create new fragrance characters and address a re-occurring consumer issue that particular fragrance profiles, particularly fragrance compositions containing heavy floral, spicy, musky and woody notes, are too slow to develop and also tend to last too long.

Such a solution as presented herein provides suppressed longevity of the fragrance profile. This provides the perfumer options to formulate accords having new fragrance profiles.

Volatile Solvents

In yet another aspect, additional suitable solvents may be present in the fragrance composition of the present invention. For example, for perfume applications in particular, ethanol may be present in any of the fragrance compositions of the present invention, and more specifically, it will form from about 10 wt % to about 80 wt %, or even from about 25 wt % to about 75 wt % of the fragrance composition, or combinations thereof, relative to the total weight of the fragrance composition. Any acceptable quality of ethanol (preferably high-quality), compatible and safe for the specific intended use of the fragrance composition such as, for example, topical applications of fine fragrance or cosmetic compositions, and is convenient for use in the fragrance compositions according to the present invention.

Low Volatile Co-Solvents

The fragrance composition may comprise a low volatility co-solvent or a mixture of low volatility co-solvents. As used herein, the term "low volatility co-solvents" include solvents that have a vapour pressure of less than 0.3 Torr (<0.040 kPa) at 25° C. Preferably, the low volatility co-solvents do not contribute significantly to the odour profile of the fragrance compositions. For example, for perfume applications, a low volatility co-solvent or a mixture of low volatility co-solvents may be present in any of the fragrance compositions of the present invention, and more specifically, it may form from about 0.1 wt % to about 50 wt %, or even from about 1 wt % to about 40 wt % of the fragrance composition, or combinations thereof, relative to the total weight of the fragrance composition. Non-limiting examples of suitable low volatility co-solvents include benzyl benzoate, diethyl phthalate, isopropyl myristate, propylene glycol, triethyl citrate, and mixtures thereof.

Water

In yet another aspect, water may be present in any of the fragrance compositions of the present invention, and more specifically, it shall not exceed about 50 wt %, preferably about 40 wt % or less, relative to the total weight of the composition. Alternatively, water may be present in an amount of less than 50 wt %, less than 40 wt %, less than 30 wt %, less than 20 wt % or less than 10 wt %, wherein the wt % is relative to the total weight of the fragrance composition. When the fragrance composition is a cosmetic composition, the level of water should not be so high that the product becomes cloudy or phase separates thus negatively impacting the product aesthetics. It is understood that the amount of water present in the fragrance composition may be from the water present in the ethanol used in the fragrance composition, as the case may be.

Propellants

The fragrance compositions described herein may include a propellant. Some examples of propellants include compressed air, nitrogen, inert gases, carbon dioxide, and mixtures thereof. Propellants may also include gaseous hydrocarbons like propane, butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (butane), A-108 (propane), AP70 (a mixture of propane, isobutane and n-butane), AP40 (a mixture of propane, isobutene and butane), AP30 (a mixture of propane, isobutene and butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42% by weight of the total fill of materials stored within the container.

Antiperspirant Active

The fragrance compositions described herein may be free of, substantially free of, or may include an antiperspirant active (i.e., any substance, mixture, or other material having antiperspirant activity). Examples of antiperspirant actives include astringent metallic salts, like the inorganic and organic salts of aluminum, zirconium and zinc, as well as mixtures thereof. Such antiperspirant actives include, for example, the aluminium and zirconium salts, such as aluminium halides, aluminium hydroxohalides, zirconyl oxohalides, zirconyl hydroxohalides, and mixtures thereof.

Other Ingredients

In yet another aspect, the fragrance composition consists essentially of the recited ingredients but may contain small amounts (not more than about 10 wt %, preferably no more than 5 wt %, or preferably no more than 2 wt % thereof, relative to the total weight of the composition) of other ingredients that do not impact on the fragrance profile, particularly the evaporation rate and release of the fragrance materials. For example, a fragrance composition may comprise stabilising or anti-oxidant agents, UV filters or quenchers, or colouring agents, commonly used in perfumery. There are a number of other examples of additional ingredients that are suitable for inclusion in the present compositions, particularly in compositions for cosmetic use. These include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, and propyl paraben; dyes; pH adjusting agents such as lactic acid, citric acid, sodium citrate, succinic acid, phosphoric acid, sodium hydroxide, and sodium carbonate; deodorants and anti-microbials such as farnesol and zinc phenolsulphonate; humectants such as glycerine; oils; skin conditioning agents such as allantoin; cooling agents such as trimethyl isopropyl butanamide and menthol; hair conditioning ingredients such as panthenol, panthetine, pantothoine, panthenyl ethyl ether, and combinations thereof; silicones; solvents such as hexylene glycol; hair-hold polymers such as those described in PCT Publication WO94/08557 (Procter & Gamble); salts in general, such as potassium acetate and sodium chloride and mixtures thereof.

In yet another aspect, the fragrance compositions for use in the present invention may take any form suitable for use, more preferably for perfumery or cosmetic use. These include, but are not limited to, vapour sprays, aerosols, emulsions, lotions, liquids, creams, gels, sticks, ointments, pastes, mousses, powders, granular products, substrates, cosmetics (e.g. semi-solid or liquid makeup, including foundations) and the like. Preferably the fragrance compositions for use in the present invention take the form of a vapour spray. Fragrance compositions of the present invention can be further added as an ingredient to other compositions, preferably fine fragrance or cosmetic compositions, in which they are compatible. As such they can be used within solid composition or applied substrates etc.

Therefore, it goes without saying that the fragrance compositions of the present invention encompasses any composition comprising any of the ingredients cited herein, in any embodiment wherein each such ingredient is independently present in any appropriate amount as defined herein. Many such fragrance compositions, than what is specifically set out herein, can be encompassed.

Article of Manufacture

The fragrance composition may be included in an article of manufacture comprising a spray dispenser. The spray dispenser may comprise a vessel for containing the fragrance composition to be dispensed. The spray dispenser may comprise an aerosolised fragrance composition (i.e. a fragrance composition comprising a propellant) within the vessel as well. Other non-limiting examples of spray dispensers include non-aerosol dispensers (e.g. vapour sprays), manually activated dispensers, pump-spray dispensers, or any other suitable spray dispenser available in the art.

Methods of Using the Fragrance Compositions

The fragrance composition of the present invention according to any embodiments described herein is a useful perfuming composition, which can be advantageously used as consumer products for personal care application intended to perfume any suitable substrate. As used herein, the term "substrate" means any surface to which the fragrance composition of the present invention may be applied to without causing any undue adverse effect. For example, this can include a wide range of surfaces including human or animal skin or hair. Preferred substrates include body surfaces such as, for example, hair and skin, most preferably skin.

The fragrance composition of the present invention may be used in a conventional manner for fragrancing a substrate. An effective amount of the fragrance composition, typically from about 1 µL to about 10,000 µL, preferably from about 10 µL to about 1,000 µL, more preferably from about 25 µL to about 500 µL, or most preferably from about 50 µL to about 100 µL, or combinations thereof, is applied to the suitable substrate. Alternatively, an effective amount of the fragrance composition of the present invention is from about 1 µL, 10 µL, 25 µL or 50 µL to about 100 µL, 500 µL, 1,000 µL or 10,000 µL. The fragrance composition may be applied by hand or applied utilising a delivery apparatus such as, for example, vaporiser or atomiser. Preferably, the fragrance composition is allowed to dry after its application to the substrate. The scope of the present invention should be considered to cover one or more distinct applications of the fragrance composition In one embodiment, present invention preferably relates to fragrance compositions in the form of product selected from the group consisting of a perfume, an eau de toilette, an eau de parfum, a cologne, an after shave lotion, a body splash, or a body spray. Therefore, according to this embodiment, the present invention provides a method of modifying or enhancing the odour properties of a body surface, preferably hair or skin, comprising contacting or treating the body surface with a fragrance composition of the present invention.

In another aspect, the present invention is directed to a method of enhancing evaporation rate of the fragrance profile of a fragrance composition, preferably by increasing the volatility of the PRMs, preferably the components derived from the less or least volatile PRMs, present in the fragrance composition. The method comprises bringing into contact or mixing at least one ionic liquid as described hereinabove with at least one low volatility fragrance material according to the fragrance composition of the present invention.

In one embodiment, the fragrance profile of the fragrance composition is detectable by a consumer only up to certain time points, such as for example, 1 hour, 2 hours, 4 hours, 6 hours, 8 hours, 10 hours, and possibly all the way up to 24 hours after application of the fragrance composition to a substrate as compared to controls.

Fragrance Materials

In order that the fragrance compositions can be developed with the appropriate fragrance profile for the present invention, the PRMs have been classified by their vapour pressure. For the purpose of clarity, when the PRMs refer to a single individual compound, its vapour pressure should be determined according to the reference program cited above. In the case that the PRMs are a natural oil, extract or absolute, which comprises a mixture of several compounds, the vapour pressure of the complete oil should be treated as a mixture of the individual perfume raw material components using the reference program cited above. The individual components and their level, in any given natural oil or extract, can be determined by direct injection of the oil into a GC-MS column for analysis as known by one skilled in the art. In the scenario that the PRMs are a proprietary speciality accord, so called bases', the vapour pressure, using the reference program cited above, should preferably be obtained from the supplier. However, it is understood by one skilled in the art that they can physically analyse the composition of a full fragrance oil available commercially to identify the PRMs and their levels using standard GC-MS techniques. This would be irrespective of whether they had been added to the fragrance oil as individual chemicals, as components of naturals or from proprietary bases. Although proprietary bases and and naturals are included in our examples, when analysing a commercially available fragrance composition via GC-MS one could simply identify the components of the base or natural oil as part of the overall fragrance mixture and their levels, without being able to identify which proprietary base or natural oil the PRM had come from.

The nature and type of PRMs in the fragrance compositions according to the present invention can be selected by the skilled person, on the basis of its general knowledge together with the teachings contained herein, with reference to the intended use or application of the fragrance composition and the desired fragrance profile effect. Non-limiting examples of suitable PRMs are disclosed in U.S. Pat. No. 4,145,184, U.S. Pat. No. 4,209,417, U.S. Pat. No. 4,515,705 and U.S. Pat. No. 4,152,272. Preferably, the fragrance composition comprises low volatility perfume raw material having a vapour pressure less than 0.003 Torr (<0.00040 kPa) at 25° C. and the low volatility perfume raw material is present in an amount from about 0.001 wt % to about 99.9 wt %, preferably from about 0.01 wt % to about 99 wt %, relative to the total weight of the fragrance composition. In a preferred embodiment, the fragrance composition comprises at least 2, 3, 4, 5, 6 or more low volatility perfume raw materials having a vapour pressure less than 0.003 Torr (<0.00040 kPa) at 25° C.

Preferable non-limiting examples of low volatility perfume raw materials are listed in Table 1.

TABLE 1

Low Volatility Perfume Raw Materials for Use in the Fragrance Compositions

| CAS Number | Chemical Name | Common Name** | Vapour Pressure/ Torr*§ |
|---|---|---|---|
| 313973-37-4 | 1,6-Heptadien-3-one, 2-cyclohexyl- | Pharaone | 0.00298 |
| 7779-30-8 | 1-Penten-3-one, 1-(2,6,6-trimethyl-2-cyclohexen-1-yl)- | Methyl Ionone | 0.00286 |

TABLE 1-continued

Low Volatility Perfume Raw Materials for Use in the Fragrance Compositions

| CAS Number | Chemical Name | Common Name** | Vapour Pressure/ Torr*§ |
|---|---|---|---|
| 104-67-6 | 2(3H)-Furanone, 5-heptyldihydro- | gamma-Undecalactone (racemic) | 0.00271 |
| 33704-61-9 | 4H-Inden-4-one, 1,2,3,5,6,7-hexahydro-1,1,2,3,3-pentamethyl- | Cashmeran | 0.00269 |
| 36306-87-3 | Cyclohexanone, 4-(1-ethoxyethenyl)-3,3,5,5-tetramethyl- | Kephalis | 0.00269 |
| 141-13-9 | 9-Undecenal, 2,6,10-trimethyl- | Adoxal | 0.00257 |
| 2110-18-1 | Pyridine, 2-(3-phenylpropyl)- | Corps Racine VS | 0.00257 |
| 27606-09-3 | Indeno[1,2-d]-1,3-dioxin, 4,4a,5,9b-tetrahydro-2,4-dimethyl- | Magnolan | 0.00251 |
| 67634-20-2 | Propanoic acid, 2-methyl-, 3a,4,5,6,7,7a-hexahydro-4,7-methano-1H-inden-5-yl ester | Cyclabute | 0.00244 |
| 65405-72-3 | 1-Naphthalenol, 1,2,3,4,4a,7,8,8a-octahydro-2,4a,5,8a-tetramethyl-, 1-formate | Oxyoctaline Formate | 0.00236 |
| 25152-85-6 | 3-Hexen-1-ol, 1-benzoate, (3Z)- | Cis-3-Hexenyl Benzoate | 0.00203 |
| 77-54-3 | 1H-3a,7-Methanoazulen-6-ol, octahydro-3,6,8,8-tetramethyl-, 6-acetate, (3R,3aS,6R,7R,8aS)- | Cedac | 0.00192 |
| 76842-49-4 | 4,7-Methano-1H-inden-6-ol, 3a,4,5,6,7,7a-hexahydro-8,8-dimethyl-, 6-propanoate | Frutene | 0.00184 |
| 211299-54-6 | 4H-4a,9-Methanoazuleno[5,6-d]-1,3-dioxole, octahydro-2,2,5,8,8,9a-hexamethyl-, (4aR,5R,7aS,9R)- | Ambrocenide | 0.00182 |
| 10094-34-5 | 2-methyl-1-phenylpropan-2-ylbutanoate | Dimethyl benzyl carbinyl butyrate | 0.00168 |
| 40785-62-4 | Cyclododeca[c]furan, 1,3,3a,4,5,6,7,8,9,10,11,13a-dodecahydro- | Muscogene | 0.00163 |
| 75490-39-0 | Benzenebutanenitrile, α,α,γ-trimethyl- | Khusinil | 0.00162 |
| 55418-52-5 | 2-Butanone, 4-(1,3-benzodioxol-5-yl)- | Dulcinyl | 0.00161 |
| 72089-08-8 | 3-Cyclopentene-1-butanol, β,2,2,3-tetramethyl- 2-Methyl-4-(2,2,3-trimethyl-3-cyclopenten-1-yl)butanol | Brahmanol | 0.00154 |
| 3155-71-3 | 2-Butenal, 2-methyl-4-(2,6,6-trimethyl 1-cyclohexen-1-yl)- | Boronal | 0.00147 |
| 41199-20-6 | 2-Naphthalenol, decahydro-2,5,5-trimethyl- | Ambrinol | 0.00140 |
| 91-64-5 | 2H-1-Benzopyran-2-one | Coumarin | 0.00130 |
| 68901-32-6 | 1,3-Dioxolane, 2-[6-methyl-8-(1-methylethyl)bicyclo[2.2.2]oct-5-en-2-yl]- | Glycolierral | 0.00121 |
| 68039-44-1 | Propanoic acid, 2,2-dimethyl-, 3a,4,5,6,7,7a-hexahydro-4,7-methano-1H-inden-6-yl ester | Pivacyclene | 0.00119 |
| 106-29-6 | Butanoic acid, (2E)-3,7-dimethyl-2,6 octadien-1-yl ester | Geranyl Butyrate | 0.00116 |
| 109-42-2 | 10-Undecenoic acid, butyl ester | Butyl Undecylenate | 0.00104 |
| 198404-98-7 | Cyclopropanemethanol, 1-methyl-2-[(1,2,2-trimethylbicyclo[3.1.0]hex-3-yl)methyl]- | Javanol ® | 0.000902 |
| 139504-68-0 | 2-Butanol, 1-[[2-(1,1-dimethylethyl)cyclohexyl]oxy]- | Amber core | 0.000803 |
| 502847-01-0 | Spiro[5.5]undec-8-en-1-one, 2,2,7,9-tetramethyl- | Spiro[5.5]undec-8-en-1-one, 2,2,7,9-tetramethyl- | 0.000731 |
| 101-86-0 | Octanal, 2-(phenylmethylene)- | Hexyl cinnamic aldehyde | 0.000697 |
| 37172-53-5 | Cyclopentanecarboxylic acid, 2-hexyl-3-oxo-, methyl ester | Dihydro Iso Jasmonate | 0.000675 |
| 65113-99-7 | 3-Cyclopentene-1-butanol, α,β,2,2,3-pentamethyl- | Sandalore ® | 0.000625 |
| 68133-79-9 | Cyclopentanone, 2-(3,7-dimethyl-2,6 octadien-1-yl)- | Apritone | 0.00062 |
| 7212-44-4 | 1,6,10-Dodecatrien-3-ol, 3,7,11-trimethyl- | Nerolidol | 0.000616 |
| 134123-93-6 | Benzenepropanenitrile, 4-ethyl-α,α-dimethyl- | Fleuranil | 0.000576 |
| 77-53-2 | 1H-3a,7-Methanoazulen-6-ol, octahydro-3,6,8,8-tetramethyl-, (3R,3aS,6R,7R,8aS)- | Cedrol Crude | 0.000569 |

TABLE 1-continued

Low Volatility Perfume Raw Materials for Use in the Fragrance Compositions

| CAS Number | Chemical Name | Common Name** | Vapour Pressure/ Torr*§ |
|---|---|---|---|
| 54464-57-2 | Ethanone, 1-(1,2,3,4,5,6,7,8-octahydro-2,3,8,8-tetramethyl-2-naphthalenyl)- | Iso-E Super ® | 0.000538 |
| 79-78-7 | 1,6-Heptadien-3-one, 1-(2,6,6-trimethyl-2-cyclohexen-1-yl)- | Hexalon | 0.000498 |
| 153859-23-5 | Cyclohexanepropanol, 2,2,6-trimethyl-α-propyl-, (1R,6S)- | Norlimbanol | 0.000469 |
| 70788-30-6 | Cyclohexanepropanol, 2,2,6-trimethyl-α-propyl- | Timberol | 0.000469 |
| 68555-58-8 | Benzoic acid, 2-hydroxy-, 3-methyl-2-buten-1-yl ester | Prenyl Salicylate | 0.000457 |
| 30168-23-1 | Butanal, 4-(octahydro-4,7-methano-5H-inden-5-ylidene)- | Dupical | 0.000441 |
| 1222-05-5 | Cyclopenta[g]-2-benzopyran, 1,3,4,6,7,8-hexahydro-4,6,6,7,8,8-hexamethyl- | Galaxolide | 0.000414 |
| 95962-14-4 | Cyclopentanone, 2-[2-(4-methyl-3-cyclohexen-1-yl)propyl]- | Nectaryl | 0.000367 |
| 4674-50-4 | 2(3H)-Naphthalenone, 4,4a,5,6,7,8-hexahydro-4,4a-dimethyl-6-(1-methylethenyl)-, (4R,4aS,6R)- | Nootkatone | 0.000358 |
| 3487-99-8 | 2-Propenoic acid, 3-phenyl-, pentyl ester | Amyl Cinnamate | 0.000352 |
| 128119-70-0 | 1-Propanol, 2-methyl-3-[(1,7,7-trimethylbicyclo[2.2.1]hept-2-yl)oxy]- | Bornafix | 0.000334 |
| 103614-86-4 | 1-Naphthalenol, 1,2,3,4,4a,5,8,8a-octahydro-2,2,6,8-tetramethyl- | Octalynol | 0.000332 |
| 7785-33-3 | 2-Butenoic acid, 2-methyl-, (2E)-3,7-dimethyl-2,6-octadien-1-yl ester, (2E)- | Geranyl Tiglate | 0.000332 |
| 117933-89-8 | 1,3-Dioxane, 2-(2,4-dimethyl-3-cyclohexen-1-yl)-5-methyl-5-(1-methylpropyl)- | Karanal | 0.000331 |
| 67801-20-1 | 4-Penten-2-ol, 3-methyl-5-(2,2,3-trimethyl-3-cyclopenten-1-yl)- | Ebanol | 0.000281 |
| 28219-61-6 | 2-Buten-1-ol, 2-ethyl-4-(2,2,3-trimethyl-3-cyclopenten-1-yl)- | Laevo Trisandol | 0.00028 |
| 5986-55-0 | 1,6-Methanonaphthalen-1(2H)-ol, octahydro-4,8a,9,9-tetramethyl-, (1R,4S,4aS,6R,8aS)- | Healingwood | 0.000278 |
| 120-51-4 | Benzoic acid, phenylmethyl ester | Benzyl Benzoate | 0.000254 |
| 3100-36-5 | 8-Cyclohexadecen-1-one | Cyclohexadecenone | 0.000253 |
| 541-91-3 | Cyclopentadecanone, 3-methyl- | Muskone | 0.000176 |
| 118-58-1 | Benzoic acid, 2-hydroxy-, phenylmethyl ester | Benzyl salicylate | 0.000175 |
| 81783-01-9 | 6,8-Nonadien-3-one, 2,4,4,7-tetramethyl-, oxime | Labienoxime | 0.000173 |
| 25485-88-5 | Benzoic acid, 2-hydroxy-, cyclohexyl ester | Cyclohexyl Salicylate | 0.000173 |
| 91-87-2 | Benzene, [2-(dimethoxymethyl)-1-hepten-1-yl]- | Amyl Cinnamic Aldehyde Dimethyl Acetal | 0.000163 |
| 104864-90-6 | 3-Cyclopentene-1-butanol, β,2,2,3-tetramethyl-δ-methylene- | Firsantol | 0.00016 |
| 224031-70-3 | 4-Penten-1-one, 1-spiro[4.5]dec-7-en-7-yl- | Spirogalbanone | 0.000153 |
| 236391-76-7 | Acetic acid, 2-(1-oxopropoxy)-, 1-(3,3-dimethylcyclohexyl)ethyl ester | Romandolide ® | 0.000124 |
| 107898-54-4 | 4-Penten-2-ol, 3,3-dimethyl-5-(2,2,3 trimethyl-3-cyclopenten-1-yl)- | Polysantol ® | 0.000117 |
| 107898-54-4 | 5,8-Methano-2H-1-benzopyran-2-one, 6-ethylideneoctahydro- | Florex | 0.00011 |
| 69486-14-2 | 4-Cyclopentadecen-1-one, (4Z)- | Exaltenone | 0.0000964 |
| 32388-55-9 | Ethanone, 1-[(3R,3aR,7R,8aS)-2,3,4,7,8,8a-hexahydro-3,6,8,8-tetramethyl-1H-3a,7-methanoazulen-5-yl]- | Vertofix ® | 0.0000849 |
| 131812-67-4 | 1,3-Dioxolane, 2,4-dimethyl-2-(5,6,7,8-tetrahydro-5,5,8,8-tetramethyl-2-naphthalenyl)- | Okoumal ® | 0.000076 |
| 106-02-5 | Oxacyclohexadecan-2-one | Exaltolide ® | 0.0000643 |
| 141773-73-1 | 1-Propanol, 2-[1-(3,3-dimethylcyclohexyl)ethoxy]-2-methyl-, 1-propanoate | Helvetolide ® | 0.0000579 |
| 63314-79-4 | 5-Cyclopentadecen-1-one, 3-methyl- | Delta Muscenone | 0.0000565 |
| 28371-99-5 | Ethanone, 1-(2,6,10-trimethyl-2,5,9-cyclododecatrien-1-yl)- | Trimofix O | 0.0000458 |

TABLE 1-continued

Low Volatility Perfume Raw Materials for Use in the Fragrance Compositions

| CAS Number | Chemical Name | Common Name** | Vapour Pressure/ Torr*§ |
|---|---|---|---|
| 16223-63-5 | 1H-3a,6-Methanoazulene-3-methanol, octahydro-7,7-dimethyl-8-methylene-, (3S,3aR,6R,8aS)- | Khusimol | 0.000044 |
| 10461-98-0 | Benzeneacetonitrile, α-cyclohexylidene- | Peonile | 0.0000429 |
| 50607-64-2 | Benzoic acid, 2-[(2-methylpentylidene) amino]-, methyl ester | Mevantraal | 0.0000407 |
| 94-47-3 | Benzoic acid, 2-phenylethyl ester | Phenyl Ethyl Benzoate | 0.0000348 |
| 66072-32-0 | Cyclohexanol, 4-(1,7,7-trimethylbicyclo[2.2.1]hept-2-yl)- | Iso Bornyl Cyclohexanol | 0.0000301 |
| 21145-77-7 | Ethanone, 1-(5,6,7,8-tetrahydro-3,5,5,6,8,8-hexamethyl-2-naphthalenyl)- | Fixolide | 0.0000286 |
| 22442-01-9 | 2-Cyclopentadecen-1-one, 3-methyl- | Muscenone | 0.0000277 |
| 109-29-5 | Oxacycloheptadecan-2-one | Silvanone Ci | 0.000026 |
| 102-20-5 | Benzeneacetic acid, 2-phenylethyl ester | Phenyl Ethyl Phenyl Acetate | 0.000023 |
| 118562-73-5 | Cyclododecaneethanol, β-methyl- | Hydroxyambran | 0.000018 |
| 103-41-3 | 2-Propenoic acid, 3-phenyl-, phenylmethyl ester | Benzyl Cinnamate | 0.0000105 |
| 183551-83-9 | Naphtho[2,1-b]furan-6(7H)-one, 8,9-dihydro-1,5,8-trimethyl-, (8R)- | Myrrhone | 0.00000977 |
| 120-11-6 | Benzene, 2-methoxy-1-(phenylmethoxy)-4-(1-propen-1-yl)- | Benzyl Iso Eugenol | 0.00000676 |
| 102-22-7 | Benzeneacetic acid, (2E)-3,7-dimethyl-2,6-octadien-1-yl ester | Geranyl Phenylacetate | 0.00000645 |
| 87-22-9 | Benzoic acid, 2-hydroxy-, 2-phenylethyl ester | Phenyl Ethyl Salicylate | 0.00000299 |
| 78-37-5 | 2-Propenoic acid, 3-phenyl-, 1-ethenyl-1,5-dimethyl-4-hexen-1-yl ester | Linalyl Cinnamate | 0.00000174 |
| 28645-51-4 | Oxacycloheptadec-10-en-2-one | Ambrettolide | 0.00000139 |
| 123-69-3 | Oxacycloheptadec-8-en-2-one, (8Z)- | Ambrettolide | 0.00000136 |
| 3391-83-1 | 1,7-Dioxacycloheptadecan-8-one | Musk RI | 0.00000057 |

*Vapour Pressures were acquired from Scifinder, which utilises the ACD Software V.14.02, as described in the Test Methods Section.
**Origin: The low volatility PRMs may be obtained from one or more of the following companies: Firmenich (Geneva, Switzerland), Symrise AG (Holzminden, Germany), Givaudan (Argenteuil, France), IFF (Hazlet, New Jersey), Bedoukian (Danbury, Connecticut), Sigma Aldrich (St. Louis, Missouri), Millennium Speciality Chemicals (Olympia Fields, Illinois), Polarone International (Jersey City, New Jersey), and Aroma & Flavor Specialities (Danbury, Connecticut).
§Torr is converted into kPa units by multiplying the Torr value by a factor of 0.133.

Exemplary low volatility PRMs selected from the group consisting of the ingredients mentioned in Table 1 are preferred. However, it is understood by one skilled in the art that other low volatility perfume raw materials, not recited in Table 1, would also fall within the scope of the present invention, so long as they have a vapour pressure less than 0.003 Torr (<0.00040 kPa) at 25° C. Preferably, the low volatility perfume raw material is selected from the group consisting of: 2-methyl-1-phenylpropan-2-yl butanoate; 4-penten-2-ol, 3-methyl-5-(2,2,3-trimethyl-3-cyclopenten-1-yl)-; 1-propanol, 2-[1-(3,3-dimethylcyclohexyl)ethoxy]-2-methyl-, 1-propanoate; and benzeneacetonitrile, α-cyclohexylidene-.

Preferably, the fragrance composition comprises a perfume raw material, wherein the perfume raw material further comprises at least one, two, three, four or more highly volatile perfume raw materials having a vapour pressure greater than 0.003 Torr (>0.00040 kPa) at 25° C., and the highly volatile perfume raw material is present in an amount from 0.001 wt % to 99.9 wt %, wherein the wt % is relative to the total weight of the perfume raw material. Preferable non-limiting examples of highly volatile perfume raw materials having a vapour pressure greater than 0.003 Torr (>0.00040 kPa) at 25° C. are listed in Table 2.

TABLE 2

Highly Volatile Perfume Raw Materials for Use in the Fragrance Compositions

| CAS Number | Chemical Name | Common Name** | Vapour Pressure/ Torr*§ |
|---|---|---|---|
| 107-31-3 | Formic acid, methyl ester | Methyl Formate | 732.00000000 |
| 75-18-3 | Methane, 1,1'-thiobis- | Dimethyl Sulfide 1.0% In DEP | 647.00000000 |
| 141-78-6 | Acetic acid ethyl ester | Ethyl Acetate | 112.00000000 |
| 105-37-3 | Propanoic acid, ethyl ester | Ethyl Propionate | 44.50000000 |
| 110-19-0 | Acetic acid, 2-methylpropyl ester | Isobutyl Acetate | 18.00000000 |
| 105-54-4 | Butanoic acid, ethyl ester | Ethyl Butyrate | 13.90000000 |
| 14765-30-1 | 1-Butanol | Butyl Alcohol | 8.52000000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 7452-79-1 | Butanoic acid, 2-methyl-, ethyl ester | Ethyl-2-Methyl Butyrate | 7.85000000 |
| 123-92-2 | 1-Butanol, 3-methyl-, 1-acetate | Iso Amyl Acetate | 5.68000000 |
| 66576-71-4 | Butanoic acid, 2-methyl-, 1-methylethyl ester | Iso Propyl 2-Methylbutyrate | 5.10000000 |
| 110-43-0 | 2-Heptanone | Methyl Amyl Ketone | 4.73000000 |
| 6728-26-3 | 2-Hexenal, (2E)- | Trans-2 Hexenal | 4.62000000 |
| 123-51-3 | 1-Butanol, 3-methyl- | Isoamyl Alcohol | 4.16000000 |
| 1191-16-8 | 2-Buten-1-ol, 3-methyl-, 1-acetate | Prenyl acetate | 3.99000000 |
| 57366-77-5 | 1,3-Dioxolane-2-methanamine, N-methyl- | Methyl Dioxolan | 3.88000000 |
| 7785-70-8 | Bicyclo[3.1.1]hept-2-ene, 2,6,6-trimethyl-, (1R,5R)- | Alpha Pinene | 3.49000000 |
| 79-92-5 | Bicyclo[2.2.1]heptane, 2,2-dimethyl-3-methylene- | Camphene | 3.38000000 |
| 94087-83-9 | 2-Butanethiol, 4-methoxy-2-methyl- | 4-Methoxy-2-Methyl-2-Butanenthiol | 3.31000000 |
| 39255-32-8 | Pentanoic acid, 2-methyl-, ethyl ester | Manzanate | 2.91000000 |
| 3387-41-5 | Bicyclo[3.1.0]hexane, 4-methylene-1-(1-methylethyl)- | Sabinene | 2.63000000 |
| 127-91-3 | Bicyclo[3.1.1]heptane, 6,6-dimethyl-2-methylene- | Beta Pinene | 2.40000000 |
| 105-68-0 | 1-Butanol, 3-methyl-, 1-propanoate | Amyl Propionate | 2.36000000 |
| 123-35-3 | 1,6-Octadiene, 7-methyl-3-methylene- | Myrcene | 2.29000000 |
| 124-13-0 | Octanal | Octyl Aldehyde | 2.07000000 |
| 7392-19-0 | 2H-Pyran, 2-ethenyltetrahydro-2,6,6-trimethyl- | Limetol | 1.90000000 |
| 111-13-7 | 2-Octanone | Methyl Hexyl Ketone | 1.72000000 |
| 123-66-0 | Hexanoic acid, ethyl ester | Ethyl Caproate | 1.66000000 |
| 470-82-6 | 2-Oxabicyclo[2.2.2]octane, 1,3,3-trimethyl- | Eucalyptol | 1.65000000 |
| 99-87-6 | Benzene, 1-methyl-4-(1-methylethyl)- | Para Cymene | 1.65000000 |
| 104-93-8 | Benzene, 1-methoxy-4-methyl- | Para Cresyl Methyl Ether | 1.65000000 |
| 13877-91-3 | 1,3,6-Octatriene, 3,7-dimethyl- | Ocimene | 1.56000000 |
| 138-86-3 | Cyclohexene, 1-methyl-4-(1-methylethenyl)- | dl-Limonene | 1.54000000 |
| 5989-27-5 | Cyclohexene, 1-methyl-4-(1-methylethenyl)-, (4R)- | d-limonene | 1.54000000 |
| 106-68-3 | 3-Octanone | Ethyl Amyl Ketone | 1.50000000 |
| 110-41-8 | Undecanal, 2-methyl- | Methyl Nonyl Acetaldehyde | 1.43000000 |
| 142-92-7 | Acetic acid, hexyl ester | Hexyl acetate | 1.39000000 |
| 110-93-0 | 5-Hepten-2-one, 6-methyl- | Methyl Heptenone | 1.28000000 |
| 81925-81-7 | 2-Hepten-4-one, 5-methyl- | Filbertone 1% in TEC | 1.25000000 |
| 3681-71-8 | 3-Hexen-1-ol, 1-acetate, (3Z)- | cis-3-Hexenyl acetate | 1.22000000 |
| 97-64-3 | Propanoic acid, 2-hydroxy-, ethyl ester | Ethyl Lactate | 1.16000000 |
| 586-62-9 | Cyclohexene, 1-methyl-4-(1-methylethylidene)- | Terpineolene | 1.13000000 |
| 51115-64-1 | Butanoic acid, 2-methylbutyl ester | Amyl butyrate | 1.09000000 |
| 106-27-4 | Butanoic acid, 3-methylbutyl ester | Amyl Butyrate | 1.09000000 |
| 99-85-4 | 1,4-Cyclohexadiene, 1-methyl-4-(1-methylethyl)- | Gamma Terpinene | 1.08000000 |
| 18640-74-9 | Thiazole, 2-(2-methylpropyl)- | 2-Isobutylthiazole | 1.07000000 |
| 928-96-1 | 3-Hexen-1-ol, (3Z)- | cis-3-Hexenol | 1.04000000 |
| 100-52-7 | Benzaldehyde | Benzaldehyde | 0.97400000 |
| 141-97-9 | Butanoic acid, 3-oxo-, ethyl ester | Ethyl Acetoacetate | 0.89000000 |
| 928-95-0 | 2-Hexen-1-ol, (2E)- | Trans-2-Hexenol | 0.87300000 |
| 928-94-9 | 2-Hexen-1-ol, (2Z)- | Beta Gamma Hexenol | 0.87300000 |
| 24691-15-4 | Cyclohexane, 3-ethoxy-1,1,5-trimethyl-, cis-(9CI) | Herbavert | 0.85200000 |
| 19872-52-7 | 2-Pentanone, 4-mercapto-4-methyl- | 4-Methyl-4-Mercaptopentan-2-one 1 ppm TEC | 0.84300000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 3016-19-1 | 2,4,6-Octatriene, 2,6-dimethyl-, (4E,6E)- | Allo-Ocimene | 0.81600000 |
| 69103-20-4 | Oxirane, 2,2-dimethyl-3-(3-methyl-2,4-pentadien-1-yl)- | Myroxide | 0.80600000 |
| 189440-77-5 | 4,7-Octadienoic acid, methyl ester, (4E)- | Anapear | 0.77700000 |
| 67633-96-9 | Carbonic acid, (3Z)-3-hexen-1-yl methyl ester | Liffarome ™ | 0.72100000 |
| 123-68-2 | Hexanoic acid, 2-propen-1-yl ester | Allyl Caproate | 0.67800000 |
| 106-72-9 | 5-Heptenal, 2,6-dimethyl- | Melonal | 0.62200000 |
| 106-30-9 | Heptanoic acid, ethyl ester | Ethyl Oenanthate | 0.60200000 |
| 68039-49-6 | 3-Cyclohexene-1-carboxaldehyde, 2,4-dimethyl- | Ligustral or Triplal | 0.57800000 |
| 101-48-4 | Benzene, (2,2-dimethoxyethyl)- | Phenyl Acetaldehyde Dimethyl Acetal | 0.55600000 |
| 16409-43-1 | 2H-Pyran, tetrahydro-4-methyl-2-(2-methyl-1-propen-1-yl)- | Rose Oxide | 0.55100000 |
| 925-78-0 | 3-Nonanone | Ethyl Hexyl Ketone | 0.55100000 |
| 100-47-0 | Benzonitrile | Benzyl Nitrile | 0.52400000 |
| 589-98-0 | 3-Octanol | Octanol-3 | 0.51200000 |
| 58430-94-7 | 1-Hexanol, 3,5,5-trimethyl-, 1-acetate | Iso Nonyl Acetate | 0.47000000 |
| 10250-45-0 | 4-Heptanol, 2,6-dimethyl-, 4-acetate | Alicate | 0.45400000 |
| 105-79-3 | Hexanoic acid, 2-methylpropyl ester | Iso Butyl Caproate | 0.41300000 |
| 2349-07-7 | Propanoic acid, 2-methyl-, hexyl ester | Hexyl isobutyrate | 0.41300000 |
| 23250-42-2 | Cyclohexanecarboxylic acid, 1,4-dimethyl-, methyl ester, trans- | Cyprissate | 0.40500000 |
| 122-78-1 | Benzeneacetaldehyde | Phenyl acetaldehyde | 0.36800000 |
| 5405-41-4 | Butanoic acid, 3-hydroxy-, ethyl ester | Ethyl-3-Hydroxy Butyrate | 0.36200000 |
| 105-53-3 | Propanedioic acid, 1,3-diethyl ester | Diethyl Malonate | 0.34400000 |
| 93-58-3 | Benzoic acid, methyl ester | Methyl Benzoate | 0.34000000 |
| 16356-11-9 | 1,3,5-Undecatriene | Undecatriene | 0.33600000 |
| 65405-70-1 | 4-Decenal, (4E)- | Decenal (Trans-4) | 0.33100000 |
| 54546-26-8 | 1,3-Dioxane, 2-butyl-4,4,6-trimethyl- | Herboxane | 0.33000000 |
| 13254-34-7 | 2-Heptanol, 2,6-dimethyl- | Dimethyl-2 6-Heptan-2-ol | 0.33000000 |
| 98-86-2 | Ethanone, 1-phenyl- | Acetophenone | 0.29900000 |
| 93-53-8 | Benzeneacetaldehyde, α-methyl- | Hydratropic aldehyde | 0.29400000 |
| 80118-06-5 | Propanoic acid, 2-methyl-, 1,3-dimethyl-3-buten-1-yl ester | Iso Pentyrate | 0.28500000 |
| 557-48-2 | 2,6-Nonadienal, (2E,6Z)- | E Z-2,6-Nonadien-1-al | 0.28000000 |
| 24683-00-9 | Pyrazine, 2-methoxy-3-(2-methylpropyl)- | 2-Methoxy-3-Isobutyl Pyrazine | 0.27300000 |
| 104-57-4 | Formic acid, phenylmethyl ester | Benzyl Formate | 0.27300000 |
| 104-45-0 | Benzene, 1-methoxy-4-propyl- | Dihydroanethole | 0.26600000 |
| 491-07-6 | Cyclohexanone, 5-methyl-2-(1-methylethyl)-, (2R,5R)-rel- | Iso Menthone | 0.25600000 |
| 89-80-5 | Cyclohexanone, 5-methyl-2-(1-methylethyl)-, (2R,5S)-rel- | Menthone Racemic | 0.25600000 |
| 2463-53-8 | 2-Nonenal | 2 Nonen-1-al | 0.25600000 |
| 55739-89-4 | Cyclohexanone, 2-ethyl-4,4-dimethyl- | Thuyacetone | 0.25000000 |
| 150-78-7 | Benzene, 1,4-dimethoxy- | Hydroquinone Dimethyl Ether | 0.25000000 |
| 64988-06-3 | Benzene, 1-(ethoxymethyl)-2-methoxy- | Rosacene | 0.24600000 |
| 76-22-2 | Bicyclo[2.2.1]heptan-2-one, 1,7,7-trimethyl- | Camphor gum | 0.22500000 |
| 67674-46-8 | 2-Hexene, 6,6-dimethoxy-2,5,5-trimethyl- | Methyl pamplemousse | 0.21400000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 112-31-2 | Decanal | Decyl Aldehyde | 0.20700000 |
| 16251-77-7 | Benzenepropanal, β-methyl- | Trifernal | 0.20600000 |
| 93-92-5 | Benzenemethanol, α-methyl-, 1-acetate | Methylphenylcarbinol acetate | 0.20300000 |
| 143-13-5 | Acetic acid, nonyl ester | Nonyl Acetate | 0.19700000 |
| 122-00-9 | Ethanone, 1-(4-methylphenyl)- | Para Methyl Acetophenone | 0.18700000 |
| 24237-00-1 | 2H-Pyran, 6-butyl-3,6 dihydro-2,4-dimethyl- | Gyrane | 0.18600000 |
| 41519-23-7 | Propanoic acid, 2-methyl-, (3Z)-3-hexen-1-yl ester | Hexenyl isobutyrate | 0.18200000 |
| 93-89-0 | Benzoic acid, ethyl ester | Ethyl Benzoate | 0.18000000 |
| 20780-48-7 | 3-Octanol, 3,7-dimethyl-, 3-acetate | Tetrahydro Linalyl Acetate | 0.18000000 |
| 40853-55-2 | 1-Hexanol, 5-methyl-2-(1-methylethyl)-, 1-acetate | Tetrahydro Lavandulyl Acetate | 0.17300000 |
| 933-48-2 | Cyclohexanol, 3,3,5-trimethyl-, (1R,5R)-rel- | Trimethylcyclohexanol | 0.17300000 |
| 35158-25-9 | 2-Hexenal, 5-methyl-2-(1-methylethyl)- | Lactone of Cis Jasmone | 0.17200000 |
| 18479-58-8 | 7-Octen-2-ol, 2,6-dimethyl- | Dihydromyrcenol | 0.16600000 |
| 140-11-4 | Acetic acid, phenylmethyl ester | Benzyl acetate | 0.16400000 |
| 14765-30-1 | Cyclohexanone, 2-(1-methylpropyl)- | 2-sec-Butyl Cyclo Hexanone | 0.16300000 |
| 20125-84-2 | 3-Octen-1-ol, (3Z)- | Octenol | 0.16000000 |
| 142-19-8 | Heptanoic acid, 2-propen-1-yl ester | Allyl Heptoate | 0.16000000 |
| 100-51-6 | Benzenemethanol | Benzyl Alcohol | 0.15800000 |
| 10032-15-2 | Butanoic acid, 2-methyl-, hexyl ester | Hexyl-2-Methyl Butyrate | 0.15800000 |
| 695-06-7 | 2(3H)-Furanone, 5-ethyldihydro- | Gamma Hexalactone | 0.15200000 |
| 21722-83-8 | Cyclohexaneethanol, 1-acetate | Cyclohexyl Ethyl Acetate | 0.15200000 |
| 111-79-5 | 2-Nonenoic acid, methyl ester | Methyl-2-Nonenoate | 0.14600000 |
| 16491-36-4 | Butanoic acid, (3Z)-3-hexen-1-yl ester | Cis 3 Hexenyl Butyrate | 0.13500000 |
| 111-12-6 | 2-Octynoic acid, methyl ester | Methyl Heptine Carbonate | 0.12500000 |
| 59323-76-1 | 1,3-Oxathiane, 2-methyl-4-propyl-, (2R,4S)-rel- | Oxane | 0.12300000 |
| 62439-41-2 | Heptanal, 6-methoxy-2,6-dimethyl- | Methoxy Melonal | 0.11900000 |
| 13851-11-1 | Bicyclo[2.2.1]heptan-2-ol, 1,3,3-trimethyl-, 2-acetate | Fenchyl Acetate | 0.11700000 |
| 115-95-7 | 1,6-Octadien-3-ol, 3,7-dimethyl-, 3-acetate | Linalyl acetate | 0.11600000 |
| 18479-57-7 | 2-Octanol, 2,6-dimethyl- | Tetra-Hydro Myrcenol | 0.11500000 |
| 111-87-5 | 1-Octanol | Octyl Alcohol | 0.11400000 |
| 71159-90-5 | 3-Cyclohexene-1-methanethiol, α,α,4-trimethyl- | Grapefruit mercaptan | 0.10500000 |
| 80-25-1 | Cyclohexanemethanol, α,α,4-trimethyl-, 1-acetate | Menthanyl Acetate | 0.10300000 |
| 88-41-5 | Cyclohexanol, 2-(1,1-dimethylethyl)-, 1-acetate | Verdox ™ | 0.10300000 |
| 32210-23-4 | Cyclohexanol, 4-(1,1-dimethylethyl)-, 1-acetate | Vertenex | 0.10300000 |
| 24168-70-5 | Pyrazine, 2-methoxy-3-(1-methylpropyl)- | Methoxyisobutylpyrazine | 0.09950000 |
| 89-79-2 | Cyclohexanol, 5-methyl-2-(1-methylethenyl)-, (1R,2S,5R)- | Iso-Pulegol | 0.09930000 |
| 112-12-9 | 2-Undecanone | Methyl Nonyl Ketone | 0.09780000 |
| 103-05-9 | Benzenepropanol, α,α-dimethyl- | Phenyl Ethyl Dimethyl Carbinol | 0.09770000 |
| 125-12-2 | Bicyclo[2.2.1]heptan-2-ol, 1,7,7-trimethyl-, 2-acetate, (1R,2R,4R)-rel- | Iso Bornyl Acetate | 0.09590000 |
| 78-70-6 | 1,6-Octadien-3-ol, 3,7-dimethyl- | Linalool | 0.09050000 |
| 101-97-3 | Benzeneacetic acid, ethyl ester | Ethyl Phenyl Acetate | 0.08970000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 100-86-7 | Benzeneethanol, α,α-dimethyl- | Dimethyl Benzyl Carbinol | 0.08880000 |
| 188570-78-7 | Cyclopropanecarboxylic acid, (3Z)-3-hexen-1-yl ester | Montaverdi | 0.08640000 |
| 67634-25-7 | 3-Cyclohexene-1-methanol, 3,5-dimethyl-, 1-acetate | Floralate | 0.08500000 |
| 112-44-7 | Undecanal | Undecyl Aldehyde | 0.08320000 |
| 32669-00-4 | Ethanone, 1-(3-cycloocten-1-yl)- | Tanaisone ® | 0.08150000 |
| 98-53-3 | Cyclohexanone, 4-(1,1-dimethylethyl)- | Patchi | 0.07780000 |
| 35854-86-5 | 6-Nonen-1-ol, (6Z)- | cis-6-None-1-ol | 0.07770000 |
| 5331-14-6 | Benzene, (2-butoxyethyl)- | Butyl phenethyl ether | 0.07760000 |
| 80-57-9 | Bicyclo[3.1.1]hept-3-en-2-one, 4,6,6-trimethyl- | Verbenone | 0.07730000 |
| 22471-55-2 | Cyclohexanecarboxylic acid, 2,2,6-trimethyl-, ethyl ester, (1R,6S)-rel- | Thesaron | 0.07670000 |
| 60-12-8 | Benzeneethanol | Phenethyl alcohol | 0.07410000 |
| 106-26-3 | 2,6-Octadienal, 3,7-dimethyl-, (2Z)- | Neral | 0.07120000 |
| 5392-40-5 | 2,6-Octadienal, 3,7-dimethyl- | Citral | 0.07120000 |
| 89-48-5 | Cyclohexanol, 5-methyl-2-(1-methylethyl)-, 1-acetate, (1R,2S,5R)-rel- | Menthyl Acetate | 0.07070000 |
| 119-36-8 | Benzoic acid, 2-hydroxy-, methyl ester | Methyl salicylate | 0.07000000 |
| 4180-23-8 | Benzene, 1-methoxy-4-(1E)-1-propen-1-yl- | Anethol | 0.06870000 |
| 7549-37-3 | 2,6-Octadiene, 1,1-dimethoxy-3,7-dimethyl- | Citral Dimethyl Acetal | 0.06780000 |
| 25225-08-5 | Cyclohexanemethanol, α,3,3-trimethyl-, 1-formate | Aphermate | 0.06780000 |
| 3913-81-3 | 2-Decenal, (2E)- | 2-Decene-1-al | 0.06740000 |
| 15373-31-6 | 3-Cyclopentene-1-acetonitrile, 2,2,3-trimethyl- | Cantryl ® | 0.06700000 |
| 6485-40-1 | 2-Cyclohexen-1-one, 2-methyl-5-(1-methylethenyl)-, (5R)- | Laevo carvone | 0.06560000 |
| 16587-71-6 | Cyclohexanone, 4-(1,1-dimethylpropyl)- | Orivone | 0.06490000 |
| 62406-73-9 | 6,10-Dioxaspiro[4.5]decane, 8,8-dimethyl-7-(1-methylethyl)- | Opalal CI | 0.06290000 |
| 3720-16-9 | 2-Cyclohexen-1-one, 3-methyl-5-propyl- | Livescone | 0.06270000 |
| 13816-33-6 | Benzonitrile, 4-(1-methylethyl)- | Cumin Nitrile | 0.06230000 |
| 67019-89-0 | 2,6-Nonadienenitrile | Violet Nitrile | 0.06200000 |
| 53398-85-9 | Butanoic acid, 2-methyl-, (3Z)-3-hexen-1-yl ester | cis-3-Hexenyl Alpha Methyl Butyrate | 0.06130000 |
| 16510-27-3 | Benzene, 1-(cyclopropylmethyl)-4-methoxy- | Toscanol | 0.05870000 |
| 111-80-8 | 2-Nonynoic acid, methyl ester | Methyl Octine Carbonate | 0.05680000 |
| 103-45-7 | Acetic acid, 2-phenylethyl ester | Phenyl Ethyl Acetate | 0.05640000 |
| 13491-79-7 | Cyclohexanol, 2-(1,1-dimethylethyl)- | Verdol | 0.05430000 |
| 7786-44-9 | 2,6-Nonadien-1-ol | 2,6-Nonadien-1-ol | 0.05370000 |
| 103-28-6 | Propanoic acid, 2-methyl-, phenylmethyl ester | Benzyl Iso Butyrate | 0.05130000 |
| 28462-85-3 | Bicyclo[2.2.1]heptan-2-ol, 1,2,3,3-tetramethyl-, (1R,2R,4S)-rel- | Humus Ether | 0.04870000 |
| 122-03-2 | Benzaldehyde, 4-(1-methylethyl)- | Cuminic Aldehyde | 0.04820000 |
| 358331-95-0 | 2,5-Octadien-4-one, 5,6,7-trimethyl-, (2E)- | Pomarose | 0.04810000 |
| 562-74-3 | 3-Cyclohexen-1-ol, 4-methyl-1-(1-methylethyl)- | Terpinenol-4 | 0.04780000 |
| 68527-77-5 | 3-Cyclohexene-1-methanol, 2,4,6-trimethyl- | Isocyclogeraniol | 0.04640000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 35852-46-1 | Pentanoic acid, (3Z)-3-hexen-1-yl ester | Cis-3-Hexenyl Valerate | 0.04580000 |
| 2756-56-1 | Bicyclo[2.2.1]heptan-2-ol, 1,7,7-trimethyl-, 2-propanoate, (1R,2R,4R)-rel- | Iso Bornyl Propionate | 0.04540000 |
| 14374-92-6 | Benzene, 1-methyl-4-(1-methylethyl)-2-(1-propen-1-yl)- | Verdoracine | 0.04460000 |
| 6784-13-0 | 3-Cyclohexene-1-propanal, β,4-dimethyl- | Limonenal | 0.04380000 |
| 41884-28-0 | 1-Hexanol, 5-methyl-2-(1-methylethyl)-, (2R)- | Tetrahydro Lavandulol | 0.04230000 |
| 22457-23-4 | 3-Heptanone, 5-methyl-, oxime | Stemone ® | 0.04140000 |
| 104-50-7 | 2(3H)-Furanone, 5-butyldihydro- | Gamma Octalactone | 0.04080000 |
| 143-08-8 | 1-Nonanol | Nonyl Alcohol | 0.04070000 |
| 67634-00-8 | Acetic acid, 2-(3-methylbutoxy)-, 2-propen-1-yl ester | Allyl Amyl Glycolate | 0.04000000 |
| 464-45-9 | Bicyclo[2.2.1]heptan-2-ol, 1,7,7-trimethyl-, (1S,2R,4S)- | 1-Borneol | 0.03980000 |
| 124-76-5 | Bicyclo[2.2.1]heptan-2-ol, 1,7,7-trimethyl-, (1R,2R,4R)-rel- | 1.7.7-Trimethyl-Bicyclo-1.2.2-Heptanol-2 | 0.03980000 |
| 67874-72-0 | Cyclohexanol, 2-(1,1-dimethylpropyl)-, 1-acetate | Coniferan | 0.03980000 |
| 80-26-2 | 3-Cyclohexene-1-methanol, α,α,4-trimethyl-, 1-acetate | Terpinyl Acetate | 0.03920000 |
| 498-81-7 | Cyclohexanemethanol, α,α,4-trimethyl- | Dihydro Terpineol | 0.03920000 |
| 112-45-8 | 10-Undecenal | Undecylenic aldehyde | 0.03900000 |
| 35044-57-6 | 2,4-Cyclohexadiene-1-carboxylic acid, 2,6,6-trimethyl-, ethyl ester | Ethyl Safranate | 0.03880000 |
| 106-21-8 | 1-Octanol, 3,7-dimethyl- | Dimethyl Octanol | 0.03860000 |
| 82461-14-1 | Furan, tetrahydro-2,4-dimethyl-4-phenyl- | Rhubafuran ® | 0.03780000 |
| 56011-02-0 | Benzene, [2-(3-methylbutoxy)ethyl]- | Phenyl Ethyl Isoamyl Ether | 0.03690000 |
| 103-37-7 | Butanoic acid, phenylmethyl ester | Benzyl Butyrate | 0.03660000 |
| 118-61-6 | Benzoic acid, 2-hydroxy-, ethyl ester | Ethyl salicylate | 0.03480000 |
| 98-52-2 | Cyclohexanol, 4-(1,1-dimethylethyl)- | Patchon | 0.03480000 |
| 115-99-1 | 1,6-Octadien-3-ol, 3,7-dimethyl-, 3-formate | Linalyl Formate | 0.03440000 |
| 112-54-9 | Dodecanal | Lauric aldehyde | 0.03440000 |
| 53046-97-2 | 3,6-Nonadien-1-ol, (3Z,6Z)- | 3,6 Nonadien-1-ol | 0.03360000 |
| 76649-25-7 | 3,6-Nonadien-1-ol | 3,6-Nonadien-1-ol | 0.03360000 |
| 1975-78-6 | Decanenitrile | Decanonitrile | 0.03250000 |
| 2216-51-5 | Cyclohexanol, 5-methyl-2-(1-methylethyl)-, (1R,2S,5R)- | L-Menthol | 0.03230000 |
| 103-93-5 | Propanoic acid, 2-methyl-, 4-methylphenyl ester | Para Cresyl iso-Butyrate | 0.03120000 |
| 24717-86-0 | Propanoic acid, 2-methyl-, (1R,2S,4R)-1,7,7-trimethylbicyclo[2.2.1]hept-2-yl ester, rel- | Abierate | 0.03110000 |
| 67845-46-9 | Acetaldehyde, 2-(4-methylphenoxy)- | Aldehyde XI | 0.03090000 |
| 67883-79-8 | 2-Butenoic acid, 2-methyl-, (3Z)-3-hexen-1-yl ester, (2E)- | Cis-3-Hexenyl Tiglate | 0.03060000 |
| 33885-51-7 | Bicyclo[3.1.1]hept-2-ene-2-propanal, 6,6-dimethyl- | Pino Acetaldehyde | 0.03040000 |
| 70214-77-6 | 2-Nonanol, 6,8-dimethyl- | Nonadyl | 0.03010000 |
| 215231-33-7 | Cyclohexanol, 1-methyl-3-(2-methylpropyl)- | Rossitol | 0.02990000 |
| 120-72-9 | 1H-Indole | Indole | 0.02980000 |
| 2463-77-6 | 2-Undecenal | 2-Undecene-1-al | 0.02970000 |
| 675-09-2 | 2H-Pyran-2-one, 4,6-dimethyl- | Levistamel | 0.02940000 |
| 98-55-5 | 3-Cyclohexene-1-methanol, α,α,4-trimethyl- | alpha-Terpineol | 0.02830000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 81786-73-4 | 3-Hepten-2-one, 3,4,5,6,6-pentamethyl-, (3Z)- | Koavone | 0.02750000 |
| 39212-23-2 | 2(3H)-Furanone, 5-butyldihydro-4-methyl- | Methyl Octalactone | 0.02700000 |
| 53767-93-4 | 7-Octen-2-ol, 2,6-dimethyl-, 2-acetate | Dihydro Terpinyl Acetate | 0.02690000 |
| 104-55-2 | 2-Propenal, 3-phenyl- | Cinnamic Aldehyde | 0.02650000 |
| 144-39-8 | 1,6-Octadien-3-ol, 3,7-dimethyl-, 3-propanoate | Linalyl Propionate | 0.02630000 |
| 61931-80-4 | 1,6-Nonadien-3-ol, 3,7-dimethyl-, 3-acetate | 3,7-Dimethyl-1,6-nonadien-3-yl acetate | 0.02630000 |
| 65443-14-3 | Cyclopentanone, 2,2,5-trimethyl-5-pentyl- | veloutone | 0.02610000 |
| 141-12-8 | 2,6-Octadien-1-ol, 3,7-dimethyl-, 1-acetate, (2Z)- | Neryl Acetate | 0.02560000 |
| 105-87-3 | 2,6-Octadien-1-ol, 3,7-dimethyl-, 1-acetate, (2E)- | Geranyl acetate | 0.02560000 |
| 68141-17-3 | Undecane, 1,1-dimethoxy-2-methyl- | Methyl Nonyl Acetaldehyde Dimethyl Acetal | 0.02550000 |
| 2206-94-2 | Benzenemethanol, α-methylene-, 1-acetate | Indocolore | 0.02550000 |
| 123-11-5 | Benzaldehyde, 4-methoxy- | Anisic aldehyde | 0.02490000 |
| 57576-09-7 | Cyclohexanol, 5-methyl-2-(1-methylethenyl)-, 1-acetate, (1R,2S,5R)- | Iso Pulegol Acetate | 0.02480000 |
| 51566-62-2 | 6-Octenenitrile, 3,7-dimethyl- | Citronellyl Nitrile | 0.02470000 |
| 30385-25-2 | 6-Octen-2-ol, 2,6-dimethyl- | Dihydromyrcenol | 0.02440000 |
| 101-84-8 | Benzene, 1,1'-oxybis- | Diphenyl Oxide | 0.02230000 |
| 136-60-7 | Benzoic acid, butyl ester | Butyl benzoate | 0.02170000 |
| 93939-86-7 | 5,8-Methano-2H-1-benzopyran, 6-ethylideneoctahydro- | Rhuboflor | 0.02120000 |
| 83926-73-2 | Cyclohexanepropanol, α,α-dimethyl- | Coranol | 0.02100000 |
| 125109-85-5 | Benzenepropanal, β-methyl-3-(1-methylethyl)- | Florhydral | 0.02070000 |
| 104-21-2 | Benzenemethanol, 4-methoxy-, 1-acetate | Anisyl Acetate | 0.02050000 |
| 2563-07-7 | Phenol, 2-ethoxy-4-methyl- | Ultravanil | 0.02030000 |
| 7493-57-4 | Benzene, [2-(1-propoxyethoxy)ethyl]- | Acetaldehyde | 0.01990000 |
| 141-25-3 | 7-Octen-1-ol, 3,7-dimethyl- | Rhodinol | 0.01970000 |
| 216970-21-7 | Bicyclo[4.3.1]decane, 3-methoxy-7,7-dimethyl-10-methylene- | 3-Methoxy-7,7-dimethyl-10-methylenebicyclo[4.3.1]decane | 0.01960000 |
| 319002-92-1 | Propanoic acid, 2-(1,1-dimethylpropoxy)-, propyl ester, (2S)- | Sclareolate ® | 0.01960000 |
| 85-91-6 | Benzoic acid, 2-(methylamino)-, methyl ester | Dimethyl anthranilate | 0.01930000 |
| 7540-51-4 | 6-Octen-1-ol, 3,7-dimethyl-, (3S)- | L-Citronellol | 0.01830000 |
| 543-39-5 | 7-Octen-2-ol, 2-methyl-6-methylene- | Myrcenol | 0.01820000 |
| 18479-54-4 | 4,6-Octadien-3-ol, 3,7-dimethyl- | Muguol | 0.01800000 |
| 1209-61-6 | 5-Oxatricyclo[8.2.0.04,6]dodecane, 4,9,12,12-tetramethyl- | Tobacarol | 0.01730000 |
| 57934-97-1 | 2-Cyclohexene-1-carboxylic acid, 2-ethyl-6,6-dimethyl-, ethyl ester | Givescone | 0.01710000 |
| 79-77-6 | 3-Buten-2-one, 4-(2,6,6-trimethyl-1-cyclohexen-1-yl)-, (3E)- | beta-Ionone | 0.01690000 |
| 64001-15-6 | 4,7-Methano-1H-inden-5-ol, octahydro-, 5-acetate | Dihydro Cyclacet | 0.01630000 |
| 134-20-3 | Benzoic acid, 2-amino-, methyl ester | Methyl anthranilate | 0.01580000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 154171-77-4 | Spiro[1,3-dioxolane-2, 8'(5'H)-[2H-2,4a] methanonaphthalene], hexahydro-1',1',5',5'-tetramethyl-, (2'S,4'aS,8'aS)-(9CI) | Ysamber K ® | 0.01470000 |
| 154171-76-3 | Spiro[1,3-dioxolane-2,8'(5'H)-[2H-2,4a]methanonaphthalene], hexahydro-1',1',5',5'-tetramethyl- | Ysamber | 0.01470000 |
| 127-41-3 | 3-Buten-2-one, 4-(2,6,6-trimethyl-2-cyclohexen-1-yl)-, (3E)- | alpha-Ionone | 0.01440000 |
| 151-05-3 | Benzeneethanol, α,α-dimethyl-, 1-acetate | Dimethyl Benzyl Carbinyl Acetate | 0.01390000 |
| 2500-83-6 | 4,7-Methano-1H-inden-5-ol, 3a,4,5,6,7,7a-hexahydro-, 5-acetate | Flor Acetate | 0.01370000 |
| 150-84-5 | 6-Octen-1-ol, 3,7-dimethyl-, 1-acetate | Citronellyl acetate | 0.01370000 |
| 30310-41-9 | 2H-Pyran, tetrahydro-2-methyl-4-methylene-6-phenyl- | Pelargene | 0.01350000 |
| 68845-00-1 | Bicyclo[3.3.1]nonane, 2-ethoxy-2,6,6-trimethyl-9-methylene- | Boisiris | 0.01350000 |
| 106-24-1 | 2,6-Octadien-1-ol, 3,7-dimethyl-, (2E)- | Geraniol | 0.01330000 |
| 75975-83-6 | Bicyclo[7.2.0]undec-4-ene, 4,11,11-trimethyl-8-methylene-, (1R,4E,9S)- | Vetyvenal | 0.01280000 |
| 19870-74-7 | 1H-3a,7-Methanoazulene, octahydro-6-methoxy-3,6,8,8-tetramethyl-, (3R,3aS,6S,7R,8aS)- | Cedryl methyl ether | 0.01280000 |
| 87-44-5 | Bicyclo[7.2.0]undec-4-ene, 4,11,11-trimethyl-8-methylene-, (1R,4E,9S)- | Caryophyllene Extra | 0.01280000 |
| 54440-17-4 | 1H-Inden-1-one, 2,3-dilydro-2,3,3-trimethyl- | Safraleine | 0.01260000 |
| 110-98-5 | 2-Propanol, 1,1'-oxybis- | Ambrocenide | 0.01250000 |
| 41890-92-0 | 2-Octanol, 7-methoxy-3,7-dimethyl- | Osyrol ® | 0.01250000 |
| 71077-31-1 | 4,9-Decadienal, 4,8-dimethyl- | Floral Super | 0.01230000 |
| 65-85-0 | Benzoic Acid | Benzoic Acid | 0.01220000 |
| 61444-38-0 | 3-Hexenoic acid, (3Z)-3-hexen-1-yl ester, (3Z)- | cis-3-hexenyl-cis-3-hexenoate | 0.01220000 |
| 116044-44-1 | Bicyclo[2.2.1]hept-5-ene-2-carboxylic acid, 3-(1-methylethyl)-, ethyl ester, (1R,2S,3S,4S)-rel- | Herbanate | 0.01210000 |
| 104-54-1 | 2-Propen-1-ol, 3-phenyl- | Cinnamic alcohol | 0.01170000 |
| 78-35-3 | Propanoic acid, 2-methyl-, 1-ethenyl-1,5-dimethyl-4-hexen-1-yl ester | Linalyl isobutyrate | 0.01170000 |
| 23495-12-7 | Ethanol, 2-phenoxy-, 1-propanoate | Phenoxy Ethyl Propionate | 0.01130000 |
| 103-26-4 | 2-Propenoic acid, 3-phenyl-, methyl ester | Methyl Cinnamate | 0.01120000 |
| 67634-14-4 | Benzenepropanal, 2-ethyl-α,α-dimethyl- | Florazon (ortho-isomer) | 0.01110000 |
| 5454-19-3 | Propanoic acid, decyl ester | N-Decyl Propionate | 0.01100000 |
| 93-16-3 | Benzene, 1,2-dimethoxy-4-(1-propen-1-yl)- | Methyl Iso Eugenol | 0.01100000 |
| 81782-77-6 | 3-Decen-5-ol, 4-methyl- | 4-Methyl-3-decen-5-ol | 0.01070000 |
| 97-53-0 | Phenol, 2-methoxy-4-(2-propen-1-yl)- | Eugenol | 0.01040000 |
| 120-57-0 | 1,3-Benzodioxole-5-carboxaldehyde | Heliotropin | 0.01040000 |
| 4826-62-4 | 2-Dodecenal | 2 Dodecene-1-al | 0.01020000 |
| 20407-84-5 | 2-Dodecenal, (2E)- | Aldehyde Mandarin | 0.01020000 |
| 5462-06-6 | Benzenepropanal, 4-methoxy-α-methyl- | Canthoxal | 0.01020000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 94-60-0 | 1,4-Cyclohexanedicarboxylic acid, 1,4-dimethyl ester | Dimethyl 1,4-cyclohexanedicarboxylate | 0.01020000 |
| 57378-68-4 | 2-Buten-1-one, 1-(2,6,6-trimethyl-3-cyclohexen-1-yl)- | delta-damascone | 0.01020000 |
| 17283-81-7 | 2-Butanone, 4-(2,6,6-trimethyl-1-cyclohexen-1-yl)- | Dihydro Beta Ionone | 0.01020000 |
| 1885-38-7 | 2-Propenenitrile, 3-phenyl-, (2E)- | Cinnamalva | 0.01010000 |
| 103-48-0 | Propanoic acid, 2-methyl-, 2-phenylethyl ester | Phenyl Ethyl Iso Butyrate | 0.00994000 |
| 488-10-8 | 2-Cyclopenten-1-one, 3-methyl-2-(2Z)-2-penten-1-yl- | Cis Jasmone | 0.00982000 |
| 7492-67-3 | Acetaldehyde, 2-[(3,7-dimethyl-6-octen-1-yl)oxy]- | Citronellyloxyacetaldehyde | 0.00967000 |
| 68683-20-5 | 1-Cyclohexene-1-ethanol, 4-(1-methylethyl)-, 1-formate | Iso Bergamate | 0.00965000 |
| 3025-30-7 | 2,4-Decadienoic acid, ethyl ester, (2E,4Z)- | Ethyl 2,4-Decadienoate | 0.00954000 |
| 103-54-8 | 2-Propen-1-ol, 3-phenyl-, 1-acetate | Cinnamyl Acetate | 0.00940000 |
| 6790-58-5 | Naphtho[2,1-b]furan, dodecahydro-3a,6,6,9a-tetramethyl-, (3aR,5aS,9aS,9bR)- | Synambran | 0.00934000 |
| 18127-01-0 | Benzenepropanal, 4-(1,1-dimethylethyl)- | Bourgeonal | 0.00934000 |
| 3738-00-9 | Naphtho[2,1-b]furan, dodecahydro-3a,6,6,9a-tetramethyl- | Ambroxan | 0.00934000 |
| 51519-65-4 | 1,4-Methanonaphthalen-5(1H)-one, 4,4a,6,7,8,8a-hexahydro- | Tamisone | 0.00932000 |
| 148-05-1 | Dodecanoic acid, 12-hydroxy-, λ,-lactone (6CI, 7CI); 1,12- | Dodecalactone | 0.00931000 |
| 2705-87-5 | Cyclohexanepropanoic acid, 2-propen-1-yl ester | Allyl Cyclohexane Propionate | 0.00925000 |
| 7011-83-8 | 2(3H)-Furanone, 5-hexyldihydro-5-methyl- | Lactojasmone ® | 0.00885000 |
| 61792-11-8 | 2,6-Nonadienenitrile, 3,7-dimethyl- | Lemonile ® | 0.00884000 |
| 692-86-4 | 10-Undecenoic acid, ethyl ester | Ethyl Undecylenate | 0.00882000 |
| 103-95-7 | Benzenepropanal, α-methyl-4-(1-methylethyl)- | Cymal | 0.00881000 |
| 94201-19-1 | 1-Oxaspiro[4.5]decan-2-one, 8-methyl- | Methyl Laitone 10% TEC | 0.00872000 |
| 104-61-0 | 2(3H)-Furanone, dihydro-5-pentyl- | γ-Nonalactone | 0.00858000 |
| 706-14-9 | 2(3H)-Furanone, 5-hexyldihydro- | γ-Decalactone | 0.00852000 |
| 24720-09-0 | 2-Buten-1-one, 1-(2,6,6-trimethyl-2-cyclohexen-1-yl)-, (2E)- | α-Damascone | 0.00830000 |
| 39872-57-6 | 2-Buten-1-one, 1-(2,4,4-trimethyl-2-cyclohexen-1-yl)-, (2E)- | Isodamascone | 0.00830000 |
| 705-86-2 | 2H-Pyran-2-one, tetrahydro-6-pentyl- | Decalactone | 0.00825000 |
| 67634-15-5 | Benzenepropanal, 4-ethyl-α,α-dimethyl- | Floralozone | 0.00808000 |
| 40527-42-2 | 1,3-Benzodioxole, 5-(diethoxymethyl)- | Heliotropin Diethyl Acetal | 0.00796000 |
| 56973-85-4 | 4-Penten-1-one, 1-(5,5-dimethyl-1-cyclohexen-1-yl)- | Neobutenone α | 0.00763000 |
| 128-51-8 | Bicyclo[3.1.1]hept-2-ene-2-ethanol, 6,6-dimethyl-, 2-acetate | Nopyl Acetate | 0.00751000 |
| 103-36-6 | 2-Propenoic acid, 3-phenyl-, ethyl ester | Ethyl Cinnamate | 0.00729000 |
| 5182-36-5 | 1,3-Dioxane, 2,4,6-trimethyl-4-phenyl- | Floropal ® | 0.00709000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 42604-12-6 | Cyclododecane, (methoxymethoxy)- | Boisambrene | 0.00686000 |
| 33885-52-8 | Bicyclo[3.1.1]hept-2-ene-2-propanal, α,α,6,6-tetramethyl- | Pinyl Iso Butyrate Alpha | 0.00685000 |
| 3288-99-1 | Benzeneacetonitrile, 4-(1,1-dimethylethyl)- | Marenil CI | 0.00665000 |
| 35044-68-9 | 2-Buten-1-one, 1-(2,6,6-trimethyl-1-cyclohexen-1-yl)- | beta-Damascone | 0.00655000 |
| 41724-19-0 | 1,4-Methanonaphthalen-6(2H)-one, octahydro-7-methyl- | Plicatone | 0.00652000 |
| 75147-23-8 | Bicyclo[3.2.1]octan-8-one, 1, 5-dimethyl-, oxime | Buccoxime ® | 0.00647000 |
| 495-62-5 | Cyclohexene, 4-(1,5-dimethyl-4-hexen-1-ylidene)-1-methyl- | Bisabolene | 0.00630000 |
| 2785-87-7 | Phenol, 2-methoxy-4-propyl- | Dihydro Eugenol | 0.00624000 |
| 87-19-4 | Benzoic acid, 2-hydroxy-, 2-methylpropyl ester | Iso Butyl Salicylate | 0.00613000 |
| 4430-31-3 | 2H-1-Benzopyran-2-one, octahydro- | Octahydro Coumarin | 0.00586000 |
| 38462-22-5 | Cyclohexanone, 2-(1-mercapto-1-methylethyl)-5-methyl- | Ringonol 50 TEC | 0.00585000 |
| 77-83-8 | 2-Oxiranecarboxylic acid, 3-methyl-3-phenyl-, ethyl ester | Ethylmethylphenylglycidate | 0.00571000 |
| 37677-14-8 | 3-Cyclohexene-1-carboxaldehyde, 4-(4-methyl-3-penten-1-yl)- | Iso Hexenyl Cyclohexenyl Carboxaldehyde | 0.00565000 |
| 103-60-6 | Propanoic acid, 2-methyl-, 2-phenoxyethyl ester | Phenoxy Ethyl iso-Butyrate | 0.00562000 |
| 18096-62-3 | Indeno[1,2-d]-1,3-dioxin, 4, 4a,5,9b-tetrahydro- | Indoflor ® | 0.00557000 |
| 63500-71-0 | 2H-Pyran-4-ol, tetrahydro-4-methyl-2-(2-methylpropyl)- | Florosa Q | 0.00557000 |
| 65405-84-7 | Cyclohexanebutanal, α,2,6,6-tetramethyl- | Cetonal ® | 0.00533000 |
| 10339-55-6 | 1,6-Nonadien-3-ol, 3,7-dimethyl- | Ethyl linalool | 0.00520000 |
| 23267-57-4 | 3-Buten-2-one, 4-(2,2,6-trimethyl-7-oxabicyclo[4.1.0]hept-1-yl)- | Ionone Epoxide Beta | 0.00520000 |
| 97-54-1 | Phenol, 2-methoxy-4-(1-propen-1-yl)- | Isoeugenol | 0.00519000 |
| 67663-01-8 | 2(3H)-Furanone, 5-hexyldihydro-4-methyl- | Peacholide | 0.00512000 |
| 33885-52-8 | Bicyclo[3.1.1]hept-2-ene-2-propanal, α,α,6,6-tetramethyl- | Pinyl Iso Butyrate Alpha | 0.00512000 |
| 23696-85-7 | 2-Buten-1-one, 1-(2,6,6-trimethyl-1,3-cyclohexadien-1-yl)- | Damascenone | 0.00503000 |
| 80-71-7 | 2-Cyclopenten-1-one, 2-hydroxy-3-methyl- | Maple Lactone | 0.00484000 |
| 67662-96-8 | Propanoic acid, 2,2-dimethyl-, 2-phenylethyl ester | Pivarose Q | 0.00484000 |
| 2437-25-4 | Dodecanenitrile | Clonal | 0.00480000 |
| 141-14-0 | 6-Octen-1-ol, 3,7-dimethyl-, 1-propanoate | Citronellyl Propionate | 0.00469000 |
| 55066-49-4 | Benzenepentanal, β-methyl- | Mefranal | 0.00455000 |
| 7493-74-5 | Acetic acid, 2-phenoxy-, 2-propen-1-yl ester | Allyl Phenoxy Acetate | 0.00454000 |
| 80-54-6 | Benzenepropanal, 4-(1,1-dimethylethyl)-α-methyl- | Lilial ® | 0.00444000 |
| 86803-90-9 | 4,7-Methano-1H-indene-2-carboxaldehyde, octahydro-5-methoxy- | Scentenal ® | 0.00439000 |
| 18871-14-2 | Pentitol, 1,5-anhydro-2,4-dideoxy-2-pentyl-, 3-acetate | Jasmal | 0.00434000 |
| 58567-11-6 | Cyclododecane, (ethoxymethoxy)- | Boisambren Forte | 0.00433000 |

TABLE 2-continued

Highly Volatile Perfume Raw Materials for Use in the Fragrance Compositions

| CAS Number | Chemical Name | Common Name** | Vapour Pressure/ Torr*§ |
|---|---|---|---|
| 94400-98-3 | Naphth[2,3-b]oxirene, 1a,2,3,4,5,6,7,7a-octahydro-1a,3,3,4,6,6-hexamethyl-, (1aR,4S,7aS)-rel- | Molaxone | 0.00425000 |
| 79-69-6 | 3-Buten-2-one, 4-(2,5,6,6-tetramethyl-2-cyclohexen-1-yl)- | alpha-Irone | 0.00419000 |
| 65442-31-1 | Quinoline, 6-(1-methylpropyl)- | Iso Butyl Quinoline | 0.00408000 |
| 87731-18-8 | Carbonic acid, 4-cycloocten-1-yl methyl ester | Violiff | 0.00401000 |
| 173445-65-3 | 1H-Indene-5-propanal, 2,3-dihydro-3,3-dimethyl- | Hivernal (A-isomer) | 0.00392000 |
| 23911-56-0 | Ethanone, 1-(3-methyl-2-benzofuranyl)- | Nerolione | 0.00383000 |
| 52474-60-9 | 3-Cyclohexene-1-carboxaldehyde, 1-methyl-3-(4-methyl-3-penten-1-yl)- | Precyclemone B | 0.00381000 |
| 139539-66-5 | 6-Oxabicyclo[3.2.1]octane, 5-methyl-1-(2,2,3-trimethyl-3-cyclopenten-1-yl)- | Cassifix | 0.00381000 |
| 32764-98-0 | 2H-Pyran-2-one, tetrahydro-6-(3-penten-1-yl)- | Jasmolactone | 0.00355000 |
| 78417-28-4 | 2,4,7-Decatrienoic acid, ethyl ester | Ethyl 2,4,7-decatrienoate | 0.00353000 |
| 140-26-1 | Butanoic acid, 3-methyl-, 2-phenylethyl ester | Beta Phenyl Ethyl Isovalerate | 0.00347000 |
| 41816-03-9 | Spiro[1,4-methanonaphthalene-2(1H), 2'-oxirane], 3,4,4a,5,8,8a-hexahydro-3',7-dimethyl- | Rhubofix ® | 0.00332000 |
| 7070-15-7 | Ethanol, 2-[[(1R,2R,4R)-1,7,7-trimethylbicyclo[2.2.1]hept-2-yl]oxy]-, rel- | Arbanol | 0.00326000 |
| 93-29-8 | Phenol, 2-methoxy-4-(1-propen-1-yl)-, 1-acetate | Iso Eugenol Acetate | 0.00324000 |
| 476332-65-7 | 2H-Indeno[4,5-b]furan, decahydro-2,2,6,6,7,8,8-heptamethyl- | Amber Xtreme Compound 1 | 0.00323000 |
| 68901-15-5 | Acetic acid, 2-(cyclohexyloxy)-, 2-propen-1-yl ester | Cyclogalbanate | 0.00323000 |
| 107-75-5 | Octanal, 7-hydroxy-3,7-dimethyl- | Hydroxycitronellal | 0.00318000 |
| 217816-75-6 | Naphtho[2,1-b]furan, 9b-ethyldodecahydro-3a,7,7-trimethyl- | Grisalva | 0.00305000 |

*Vapour Pressures were acquired from Scifinder, which utilises the ACD Software V.14.02, as described in the Test Methods Section.
**Origin: Same as for Table 1.
§Torr is converted into kPa units by multiplying the Torr value by 0.133.

Test Methods

The following assays set forth must be used in order that the invention described and claimed herein may be more fully understood.

Test Method 1: Calculated/Predicted Vapour Pressure of the Perfume Raw Materials In order to determine the vapour pressure for the pure perfume raw materials, go to the website https://scifinder.cas.org/scifindedview/scifindedscifinderExplore.jsf and follow these steps to acquire the predicted vapour pressure.
1. Input the CAS registry number for the particular fragrance material.
2. Select the vapour pressure from the search results.
3. Record the vapour pressure (given in Torr at 25° C.).
SciFinder uses Advanced Chemistry Development (ACD/Labs) Software Version to calculate a predicted vapour pressure for the particular perfume raw material. If the CAS number for the particular PRM is unknown or does not exist, you can utilise the ACD/Labs reference program to directly determine the vapour pressure. Vapour pressure is expressed in Torr, wherein 1 Torr is equal to 0.133 kilopascal (kPa).

Test Method 2: Isoteniscope Vapour Pressure

Prior to beginning the isoteniscope measurements, all ionic liquids are purified by vacuum evaporation to remove the last traces of volatile impurities and water. The PRMs are dried over molecular sieves. All mixtures are prepared gravimetrically. Samples with PRMs and ionic liquids are checked visually for miscibility prior to use. Any samples found to contain more than a single phase are not measured in this method, which typically can occur at higher levels of PRMs (e.g., 0.6 and 0.8 mole fraction).

The Isoteniscope Vapour Pressure Test Method used to experimentally determine the vapour pressure of the pure perfume raw materials and the perfume raw materials in combination with the ionic liquids is a modified version of ASTM D2879-10 wherein the following alterations are made:

Section 6: Apparatus
- 6.2: in place of a constant-temperature air bath, a constant-temperature silicone oil bath is used.
- 6.3: a hot plate with temperature sensor (IKA RCT basic) and mercury thermometer is used.
- 6.4: a vacuum pump Edwards model RV8 is used.
- 6.5: a Schlenk manifold is used.
- 6.6: an Edwards APG100 active pirani vacuum gauge is used.
- 6.7: an active digital controller Edwards (output of pressure gauge) is used.
- 6.10: air is used in place of nitrogen throughout.
- 6.12: the alcohol lamp is substituted for warming by holding via in the palm of the hands.

Section 8: Procedure

Add to the isoteniscope a quantity of sample to fill the reservoir and have a similar level in the U-bend. Attach the isoteniscope to the Schlenk manifold and evacuate the bulb system and isoteniscope to 0.1 Torr (0.013 kPa). The pressure is maintained to degas the system. Expose the material to a continuous vacuum for several minutes with gentle warming (e.g., rubbing by hand) and tilting of the isoteniscope to spread out the material.

Place the filled isoteniscope vertically into the oil bath and allow to equilibrate. The method used herein uses a lower pressure (0.1 Torr; 0.013 kPa) rather than the 1 Torr (0.13 kPa) in ASTM D2879-10) and longer exposure time (5 minutes rather than 1 min in ASTM D2879-10) to degas the sample. The U-tube levels are adjusted by controlling the strength of the vacuum rather than by adding nitrogen as in ASTM D2879-10. Repeat measurements at intervals of 5K rather than 25K.

Vapour pressures for the pure PRMs and for the mixtures of ionic liquid and PRM are reported as described in section 9.2 of the ASTM D2879-10 method. The measured vapour pressures are used to calculate the activity coefficients as specified herein.

Test Method 3: Gas-Phase Infrared Spectroscopy Method

This method determines the relative gas-phase concentration (re) of a given volatile material in a composition. In particular, the method correlates the relative gas-phase concentrations of a PRM and the IR absorbances of its vapour phase in a gas-phase IR cell. Infrared spectroscopy is a well known analytical technique with details provided in references such as Williams, D. H., Fleming, I., & Pretsch, E. (1989). Spectroscopic Methods. Organic Chemistry, (1989); Skoog, D. A., & West, D. M. (1980). *Principles of instrumental analysis* (Vol. 158). Philadelphia: Saunders College; and Alpert, N. L., Keiser, W. E., & Szymanski, H. A. (2012). *IR: theory acrd practice of infrared spectroscopy*. Springer Science & Business Media.

The method requires the equipments as listed in Table 3.

TABLE 3

| Equipment | Supplier |
|---|---|
| IR gas cell: 8 metres path-length Specac Cyclone C5 gas cell | Specac |
| Heating mantle: Heating jacket and 4000 series temperature controller | Specac |
| Spectrometer: Spectrum 100 FT-IR | Perkin Elmer |

The method includes the following steps:

Step 1—Registration of the Background

This step is to be completed before each new sample measurement to remove all volatile impurities by evacuation.

a) The IR gas cell is heated with a heating mantle, under vacuum (VP: 675 Torr/90 kPa), to 150° C. and held for 25 mins at that temperature.

b) The IR gas cell is cleaned by being flushed with $N_2$ gas for another 20 mins while keeping the temperature of the system at 150° C. with the heating mantle.

c) After the cleaning step, the gas phase is checked by running an IR scan of the background in the evacuated IR gas cell in order to determine if there is any residual PRM at the characteristic wavenumber of interest. See FIG. 4 for a typical trace. If a signal is detected, i.e. if the baseline is not flat, the cleaning procedure is repeated until no signal is detected.

Any other volatile component which might affect the spectra has been registered in the background so it can be taken into account in the quantification of the PRM signal.

Step 2—Identification of the Characteristic Peak for a Given Perfume Raw Material The identification of the fingerprint of the PRM is done by running a mid-IR scan of the vapour phase of the pure PRM in the temperature range of 30-100° C. under vacuum (VP: 675 Torn/90 kPa). The mid-IR range is between about 4,000 and 400 $cm^{-1}$. See FIG. 1 for an example IR spectrum for a PRM (e.g., dimethyl benzyl carbinyl butyrate (DMBCB)). With continued reference to FIG. 1, the wavenumber is given on the x-axis and the percent of transmittance (% T) on the y-axis. Zero % transmittance corresponds to 100% absorption of light at that wavenumber.

Another convenient way to report the absorbance intensity is in Absorbance Units (A.U.). Absorbance is the logarithm, to the base 10, of the reciprocal of the transmittance.

Carbon dioxide in the atmosphere external to the cell is seen in a broad structured band at about 2,400 $cm^{-1}$, and water exhibits a vibrational spectrum, with rotational fine structure, from 4,000-3,500 $cm^{-1}$. This gives the method two useful analytical regions of the spectrum at 2,000-1,500 $cm^{-1}$ and 3,000-2,500 $cm^{-1}$. For dimethyl benzyl carbinyl butyrate (DMBCB), the CO stretch can be seen clearly with an absorbance peak at 1,746 $cm^{-1}$ and a CH stretch with an absorbance peak at 2,890 $cm^{-1}$. In this instance the 1,746 $cm^{-1}$ peak is the cleanest peak to work with. Some characteristic wavenumbers for common bonds in PRMs are set out in Table 4.

TABLE 4

Wavenumbers for Common Bonds in PRMs

| Bonds | Absorption Region/$cm^{-1}$ |
|---|---|
| C—C, C—O, C—N | 1,300-800 |
| C=C, C=O, C=N, N=O | 1,900-1,500 |
| C≡C, C≡N | 2,300-2,000 |
| C—H, N—H, O—H | 3,800-2,700 |

Other examples of PRMs include, such as, Nectaryl with a characteristic ketone C=O stretch at 1,759 $cm^{-1}$ (see FIG. 2), and Bornafix with an OH stretch a 3,583 $cm^{-1}$ (see FIG. 3).

Step 3—Identification of the Absence of Characteristic Peak for Unperfumed Ionic Liquid The fingerprint of the neat ionic liquid is obtained by running an IR scan of its vapour phase at 45° C. At this temperature no peaks are detected. If a peak (other than originating with water or carbon dioxide) is detected, the ionic liquid has been contaminated and a new clean sample must be used.

Step 4—Characterisation of the Gas Phase of Mixtures of Ionic Liquids and PRMs
 a) The vial containing the test sample is introduced into the IR gas cell. 0.5 g of the test sample is placed on circular tray (diameter 13 mm) It is placed inside the IR gas cell so that it does not interfere with the IR beam pathway.
 b) The IR gas cell is closed and is set up under vacuum (VP: 675 Torr/90 kPa).
 c) The system is heated up to a temperature between 30-80° C., preferably 30° C., 45° C., 55° C., 65° C., and 75° C., and held at that temperature.
 d) After 40 mins a spectrum is recorded. A second spectrum is recorded after a further 10 mins. If there is no increase in the intensity of the IR peak (change is less than the standard deviation of the method) then it is deemed that equilibrium has been reached. If this condition is not met the spectrum is recorded every 10 mins until this condition is met. The final spectrum at steady-state is recorded for that sample.

Step 5—Calculation of Relative Gas Phase Concentration

The peak area ($A_i$) and height ($h_i$) are taken as the difference between the peak background baseline recorded with the evacuated cell (as in Step 1 of this procedure) and the peak recorded with the equilibrated sample of interest in the cell. It is the difference in the % transmittance for the evacuated cell and the sample of interest.

The peak area ($A_i$) and height ($h_i$) are recorded for the characteristic signal for:
 a) the pure PRM. This is proportional to the pure PRM gas-phase concentration, $c_i^0$ and the vapour pressure for the pure PRM, $P_i^0$; and
 b) each particular PRM-ionic liquid mixture. This is proportional to the gas-phase concentration and hence the vapour pressure of the PRM in the gas phase.

It is generally preferable to use the peak height rather than peak area but this may vary depending on the PRM and its characteristic spectrum. The relative gas phase concentration for any PRM-ionic liquid mixture is calculated as a ratio of its peak height to that of the pure PRM peak height. Therefore the activity co-efficient (γ) at a given PRM mole concentration can be calculated as follows, where h represents the peak height:

$$\gamma_{iX} = rc_{iX}/(X_i rc_i^0)$$

$$\gamma_{iX} = h_{iX}/(X_i * h_i^0)$$

Test Method 4: Closed Headspace Gas Chromatography

At the beginning of the measurements, all ionic liquids are purified by vacuum evaporation to remove the last traces of volatile impurities and water. The PRMs are dried over molecular sieves. All mixtures are prepared gravimetrically. Headspace gas chromatography measurements are carried out with a static apparatus with a headspace sampler from Agilent Technologies. The term "headspace" refers to the vapour space above the liquid sample placed in a vial. The 20 cm$^3$ sealed vials move from the sample tray into an oven, in which the vials are heated to a temperature of 32° C. After reaching equilibrium between the liquid and the vapour phase, the vapour phase of the respective vial is analysed by gas chromatography (Agilent Technologies) with a flame ionisation detector. Since ionic liquids have no measurable vapour pressure, they do not contribute to the gas phase, and hence to the total pressure.

Test Method 5: Olfactory Tests

In order to show the effect of the ionic liquids on the perception of fragrance profile in a fragrance composition of the present invention, test compositions are made, as described in the Example section, and given to panelists to sample.

At the testing facility, 50 µL samples of the fragrance compositions or the controls are applied to glass slides and placed on a hot plate at 32° C. to represent skin temperature for varying durations. The trained/expert panelists are asked to evaluate the perceived fragrance profile (intensity and/or character) from each pair of samples, i.e., that of the test composition of the present invention vs. the corresponding control, at time 0 and later time points (e.g., 1, 3, 6, 8 and up to 24 hours post application) as the fragrance profile evolves. Their assessments are recorded. Panelists are selected from individuals who are either trained to evaluate fragrances according to the scales below or who have considerable experience of fragrance evaluation in the industry (i.e., experts).

(a) Fragrance Intensity:

The panelists are asked to give a score on a scale of 0 to 10 for perceived fragrance intensity according to the odour intensity scale set out in Table 5 herein below.

TABLE 5

| Odour Intensity Scale | |
|---|---|
| Score | Fragrance Intensity |
| 0 | Not detectable |
| 2 | Weak |
| 4 | Moderate |
| 6 | Strong |
| 8 | Very Strong |
| 10 | Overpowering |

(b) Fragrance Character:

The panelists provide an expert description of the character of the sample.

EXAMPLES

The following examples are provided to further illustrate the present invention and are not to be construed as limitations of the present invention, as many variations of the present invention are possible without departing from its spirit or scope.

The structures of the ionic liquids of the present invention can be characterised by various techniques well-known to the skilled person, including for example: $^1$H NMR (nuclear magnetic resonance) spectroscopy, $^{13}$C NMR spectroscopy, halogen analysis and CHN elemental analysis.

Nuclear magnetic resonance ("NMR") spectroscopy is a spectroscopic technique well-known to the skilled person and used herein to characterise the ionic liquids prepared herein. Mass Spectrometry ("MS") is a spectrometric technique used herein to quantify the mass to charge ratio of particles or molecules. Two different methods of MS are used: electron spray MS ("ES-MS") and electron ionisation MS ("EI-MS"). ES-MS is used for non-volatile materials such as the ionic liquids. EI-MS is used for volatile materials such as the precursor materials.

Example 1—Syntheses of Ionic Liquids

The general method for synthesising ionic liquids of the present invention consists of: (i) synthesis of a chloride or sulfonate ester precursor; (ii) quaternisation of an amine using a chloroalkane or sulfonyl ester in order to obtain an ionic liquid with chloride or sulfonate anions; and (iii) metathesis (i.e., anion exchange) reaction in order to create the target ionic liquid. This is illustrated in Reaction Scheme 1.

Reaction Scheme 1

General Synthesis of Targeted Ionic Liquids (i) Precursor synthesis step:

R—OH + SOCl$_2$ ⟶ R—Cl
R—OH + R'SO$_2$Cl ⟶ R'SO$_3$R (ii) Quaternisation step:

R—Cl + Amine ⟶ [Cation]Cl
R'SO$_3$R + Amine ⟶ [Cation][R'SO$_3$]

(iii) Metathesis Step:

[Cation]Cl + M[Anion] ⟶ [Cation][Anion] + MCl where M = Na or K

Ionic liquids are formed by combining salts of a cation and an anion (e.g., the sodium or potassium salts of the anion and a chloride salt of the cation). Different ionic liquids can be synthesised such that the interactions between the ionic liquids and the solutes (i.e., PRMs) are optimised, preferably to provide for a positive deviation from Raoult's Law. Ionic liquids lend themselves to preparation via combinatorial or high throughput chemistry. The steps shown in the Reaction Scheme 1 are described below in more details.

Reaction Scheme 2

Step (i): Synthesis of Chloride or Sulfonate Ester Precursor (A)

R$^{4a}$—OH + SOCl$_2$ $\xrightarrow[\text{reflux}]{\text{CHCl}_3/\text{Py}}$ R$^{4a}$—Cl + SO$_2$ (B)

R$^{4a}$—OH + CH$_3$SO$_2$Cl $\xrightarrow[\text{0-20° C.}]{\text{CH}_2\text{Cl}_2/\text{Et}_3\text{N}}$ R$^{4a}$—OSO$_2$CH$_3$ (A) Chloride Precursor Synthesis:

Equimolar amounts of 2-(2-methoxyethoxy)ethanol (1A) or 2-(2-ethoxyethoxy)ethanol (1B) and pyridine are added to a three-neck round bottom flask under N$_2$. Trichloromethane is used as a solvent for the reaction. Thionyl chloride (1.2 mol eq) is added dropwise to the stirred mixture via a pressure equalising funnel. Once the addition is completed, the reaction mixture is then heated at 60° C. under reflux for 24 h. The reaction mixture is then washed with H$_2$O (4×), saturated aqueous NaHCO$_3$ (3×), dried over anhydrous MgSO$_4$ and purified by filtration. The solvent is removed under reduced pressure and the resulting crude product is then distilled yielding the pure product.

(B) Sulfonate Ester Precursor Synthesis:

Equimolar amounts of 2-(2-methoxyethoxy)ethanol (1A) and triethylamine in dichloromethane are added to a round-bottom flask in an ice bath under N$_2$. The mixture is stirred at 0° C. for 20 min before sulfonyl chloride is added dropwise, in slight excess, via a pressure equalising funnel. Once the addition is completed, the reaction mixture is warmed to room temperature overnight. The reaction mixture is then washed with H$_2$O (6×), saturated aqueous NaCl solution (3×), dried over anhydrous MgSO$_4$, purified by filtration, and concentrated to yield the sulfonate ester precursor. Sulfonate ester precursor is obtained as a colourless liquid by fractional distillation of the crude product.

TABLE 6

Structures of 1A and 1B

| | Chemical Name | Chemical Structure |
|---|---|---|
| 1A | 2-(2-methoxyethoxy)ethanol | 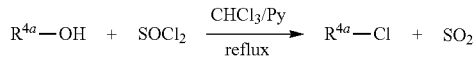 |
| 1B | 2-(2-ethoxyethoxy)ethanol | 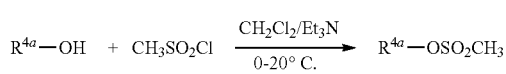 |

Reaction Scheme 3

Step (ii): Quaternisation of an Amine using Chloroalkane or Methylsulfonyl Ester Precursers

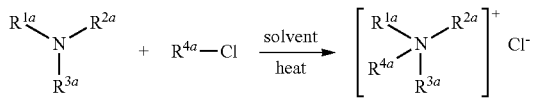

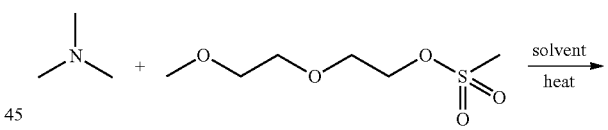

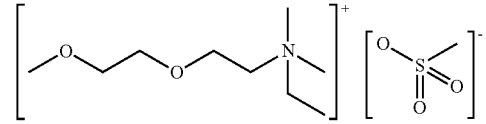

Equimolar amounts of chloride precursor or sulfonyl ester precursor and amine (dimethylethylamine or dimethyloctylamine) are added to a tetrahydrofuran in a sealable reactor. The sealed reaction mixture is stirred and heated at 60° C. until the reaction is completed. The progress of reaction is monitored by NMR spectroscopy. Solvent and unreacted amine are removed under reduced pressure. The product is washed with ethyl ethanoate (6×) and cyclohexane (2×). The residual solvent is removed via rotary evaporator and the product is dried under high vacuum at 40-80° C. for 1-3 days. Exemplary ionic liquids in Table 7 are synthesised according to this method.

TABLE 7

Exemplary Ionic Liquids with Chloride Anion or Methylsulfonate Anion from Quaternisation Reaction

| Example | Chemical Name | Chemical Structure |
| --- | --- | --- |
| Ionic Liquid 1 | (N-ethyl-2-(2-methoxyethoxy)-N,N-dimethylethanaminium) chloride | [structure] Cl⁻ |
| Ionic Liquid 2 | 2-(2-ethoxyethoxy)-N-ethyl-N,N-dimethylethanaminium chloride | [structure] Cl⁻ |
| Ionic Liquid 3 | (N-ethyl-2-(2-methoxyethoxy)-N,N-dimethylethanaminium) methylsulfonate | [structure] [methylsulfonate] |
| Ionic Liquid 4 | N-benzyl-N,N-dimethylnonan-1-aminium chloride | [structure] Cl⁻ |
| Ionic Liquid 5 | 2-(2-ethoxyethoxy)-N-ethyl-N,N-dimethylethanaminium methylsulfonate | [structure] [methylsulfonate] |
| Ionic Liquid 6 | N-benzyl-N,N-dimethylnonan-1-aminium methylsulfonate | [structure] [methylsulfonate] |

Reaction Scheme 4
Step (iii): Metathesis Synthesis Reaction of Acesulfame or Docusate Ionic Liquids

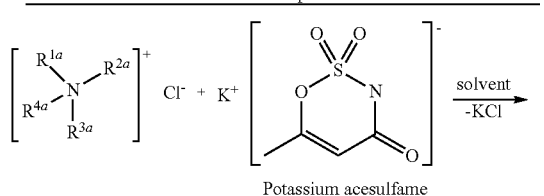

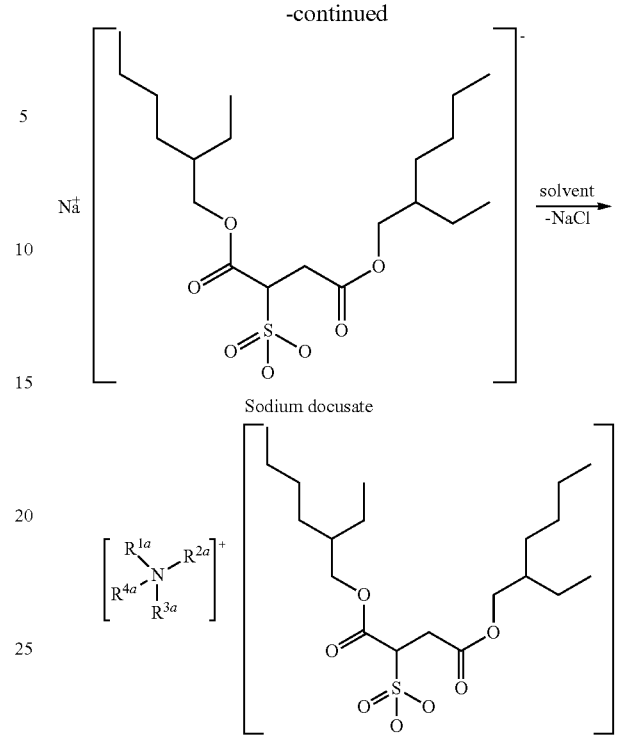

To a chloride ionic liquid in dichloromethane, potassium acesulfame or sodium docusate are added in equimolar quantities, followed by sonication and stirring for 6 h. The byproduct, potassium or sodium chloride, is removed by centrifugation at 4,400 rpm, followed by filtration. The solvent is removed via rotary evaporation. The resulting product is dried by heating at 40-80° C. for 1-3 days, under high vacuum.

TABLE 8

Exemplary Ionic Liquids with Acesulfame or Docusate Anion from Metathesis Reaction

| Example | Chemical Name | Chemical Structure |
|---|---|---|
| Ionic Liquid 7 | (N-ethyl-2-(2-methoxyethoxy)-N,N-dimethylethanaminium) 6-methyl-3,4-dihydro-1,2,3-oxathiazin-4-one 2,2-dioxide | 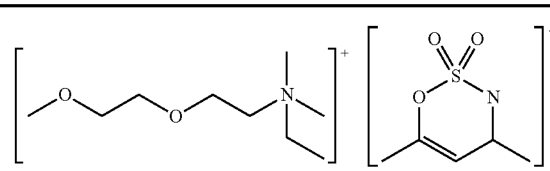 |
| Ionic Liquid 8 | 2-(2-ethoxyethoxy)-N-ethyl-N,N-dimethylethanaminium 6-methyl-3,4-dihydro-1,2,3-oxathiazin-4-one 2,2-dioxide | 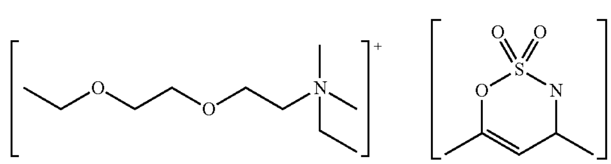 |
| Ionic Liquid 9 | N-benzyl-N,N-dimethylnonan-1-aminium 6-methyl-3,4-dihydro-1,2,3-oxathiazin-4-one 2,2-dioxide | 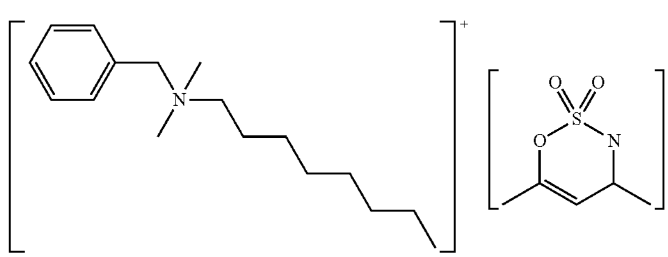 |

TABLE 8-continued

Exemplary Ionic Liquids with Acesulfame or Docusate Anion from Metathesis Reaction

| Example | Chemical Name | Chemical Structure |
|---|---|---|
| Ionic Liquid 10 | (N-ethyl-2-(2-methoxyethoxy)-N,N-dimethylethanaminium) 1,4-bis(2-ethylhexoxy)-1,4-dioxobutane-2-sulfonate | 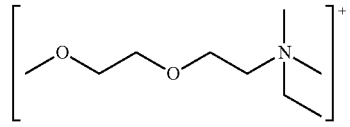 |
| Ionic Liquid 11 | 2-(2-ethoxyethoxy)-N-ethyl-N,N-dimethylethanaminium 1,4-bis(2-ethylhexoxy)-1,4-dioxobutane-2-sulfonate | 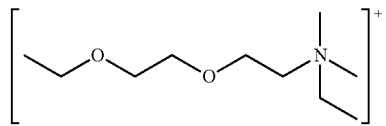 |
| Ionic Liquid 12 | N-benzyl-N,N-dimethylnonan-1-aminium 1,4-bis(2-ethylhexoxy)-1,4-dioxobutane-2-sulfonate | 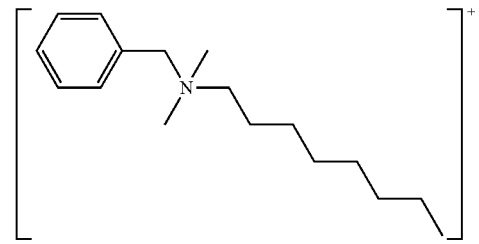 |

TABLE 8-continued

Exemplary Ionic Liquids with Acesulfame or Docusate Anion from Metathesis Reaction

| Example | Chemical Name | Chemical Structure |
|---------|---------------|--------------------|
|         |               | 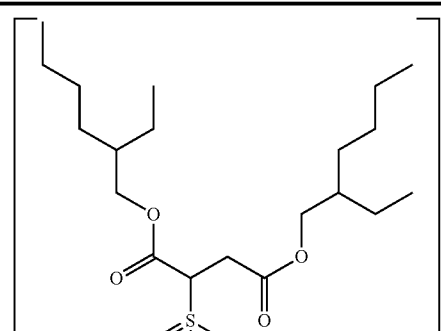 |

The characterisation data for the exemplary ionic liquids are provided in Tables 9 and 10.

TABLE 9

ES-MS and Elemental Analysis Data

| Ionic Liquid | Elem. Anal. (%) | C | H | N | S | K | Cl | ES-MS ($M^+$) | ES-MS ($M^-$) |
|---|---|---|---|---|---|---|---|---|---|
| Ionic Liquid 1 | Calcd | 51.05 | 10.47 | 6.62 | — | — | — | 176.1651 | — |
|  | Measd. | 48.24 | 10.6 | 5.95 | — | — | — | 176.1624 | — |
| Ionic Liquid 2 | Calcd. | 53.20 | 10.72 | 6.20 | — | — | — | 190.1807 | — |
|  | Measd. | 52.40 | 10.82 | 6.25 | — | — | — | 190.1782 | — |
| Ionic Liquid 3 | Calcd. | 52.75 | 10.33 | 4.10 | — | — | — | 246.2433 | 94.9803 |
|  | Measd. | 51.86 | 10.36 | 4.24 | — | — | — | 246.2417 | 94.9803 |
| Ionic Liquid 4 | Calcd. | 71.93 | 10.65 | 4.93 | — | — | — | 248.2378 | — |
|  | Measd. | 70.70 | 10.99 | 4.77 | — | — | — | 248.2375 | — |
| Ionic Liquid 5 | Calcd. | 46.29 | 9.54 | 4.91 | 11.24 | — | 0 | 190.1807 | 94.9803 |
|  | Measd. | 44.61 | 9.47 | 7.75 | 11.04 | — | 1.46 | 190.1784 | 94.9796 |
| Ionic Liquid 7 | Calcd. | 58.26 | 9.95 | 2.34 | 5.36 | 0 | 0 | 176.1651 | 161.9861 |
|  | Measd. | 57.01 | 10.3 | 2.27 | 4.70 | 0.01 | 0.13 | 176.1555 | 161.9668 |
| Ionic Liquid 8 | Calcd. | 47.71 | 8.01 | 7.95 | 9.10 | 0 | 0 | 190.1807 | 161.9861 |
|  | Measd. | 47.34 | 8.08 | 7.98 | 8.43 | 0 | 0.45 | 190.1755 | 161.9861 |
| Ionic Liquid 9 | Calcd. | 61.43 | 8.35 | 6.82 | 7.81 | 0 | 0 | 248.2378 | 161.9861 |
|  | Measd. | 61.47 | 8.67 | 6.91 | 7.67 | 0 | 0.41 | 248.2382 | 161.9829 |
| Ionic Liquid 10 | Calcd. | 58.26 | 9.95 | 2.34 | 5.36 | 0 | 0 | 176.1651 | 421.2260 |
|  | Measd. | 57.61 | 9.88 | 2.41 | — | 0.07 | 0.5 | 176.1628 | 421.2107 |
| Ionic Liquid 11 | Calcd. | 47.71 | 8.01 | 7.95 | 9.10 | 0 | 0 | 190.1807 | 421.2260 |
|  | Measd. | 47.34 | 8.08 | 7.98 | 8.45 | 0.03 | 1.1 | 190.1836 | 421.2171 |
| Ionic Liquid 12 | Calcd. | 66.35 | 10.08 | 2.09 | 4.79 | 0 | 0 | 248.2378 | 422.2260 |
|  | Measd. | 66.55 | 10.15 | 2.19 | 4.94 | 0.2 | 0.5 | 248.2366 | 422.2258 |

TABLE 10

NMR Data

| Ionic Liquid | NMR Data |
|---|---|
| Ionic Liquid 1 | $^1$H NMR ($\delta_H$/ppm, 400 MHz, CDCl$_3$): 3.98 (m, 2H); 3.94 (m, 2H); 3.80-3.79 (quartet, 2H, J = 4 Hz); 3.67 (m, 2H); 3.52 (m, 2H); 3.42 (s, 6H); 3.36 (s, 3H); 1.42 (t, 3H). |
| Ionic Liquid 2 | $^1$H NMR ($\delta_H$/ppm, 400 MHz, D$_2$O): 3.88 (m, 2H); 3.62 (m, 4H); 3.54-3.48 (m, 4H); 3.41-3.39 (quart, 2H, J = 8 Hz); 3.04 (s, 6H); 1.29 (t, 3H); 1.12 (t, 3H). |
| Ionic Liquid 3 | $^1$H NMR ($\delta_H$/ppm, 400 MHz, CDCl$_3$): 3.96 (s, 2H), 3.79 (m, 2H), 3.69-3.62 (m, 4H), 3.53-3.49 (m, 2H), 3.34 (s, 3H), 3.28 (s, 6H), 2.73 (s, 3H), 2.00 (s, 2H), 1.40 (t, 3H). Tg = −83° C. |
| Ionic Liquid 4 | $^1$H NMR ($\delta_H$/ppm, 400 MHz, CDCl$_3$) δ 7.70-7.64 (m, 2H), 7.50-7.40 (m, 3H), 5.09 (s, 2H), 3.56-3.48 (m, 2H), 3.32 (s, 6H), 2.02 (s, 1H), 1.80 (s, 2H), 1.29 (m, J = 20.5, 13.0 Hz, 10H), 0.88 (t, J = 6.8 Hz, 3H). m.p = 62° C. |
| Ionic Liquid 5 | $^1$H NMR ($\delta_H$/ppm, 400 MHz, CDCl$_3$) δ 3.96 (s, 2H), 3.81-3.74 (m, 2H), 3.67 (m, 4H), 3.57-3.44 (m, 4H), 3.29 (s, 6H), 2.72 (s, 3H), 1.41 (t, J = 7.2 Hz, 3H), 1.18 (t, J = 7.0 Hz, 3H). |
| Ionic Liquid 7 | $^1$H NMR ($\delta_H$/ppm, 400 MHz, CDCl$_3$): 5.42 (s, 1H); 3.94(m, 2H); 3.71(m, 2H); 3.64-3.62(m, 4H); 3.51(m, 2H); 3.34(s, 3H); 3.23(s, 6H); 2.00(s, 3H); 1.39(t, 3H). Tg = −66.6° C. |

TABLE 10-continued

NMR Data

| Ionic Liquid | NMR Data |
|---|---|
| Ionic Liquid 8 | $^1$H NMR ($\delta_H$/ppm, 400 MHz, D$_2$O) δ 5.60 (s, 1H), 3.88 (s, 2H), 3.62 (s, 4H), 3.58-3.44 (m, 4H), 3.39 (q, J = 7.3 Hz, 2H), 3.04 (s, 6H), 2.05 (s, 3H), 1.29 (t, 3H), 1.12 (t, 3H). |
| Ionic Liquid 9 | $^1$H NMR ($\delta_H$/ppm, 400 MHz, CDCl$_3$) δ 7.70-7.64 (m, 2H), 7.50-7.40 (m, 3H), 5.09 (s, 2H), 3.56-3.48 (m, 2H), 3.32 (s, 6H), 2.02 (s, 1H), 1.80 (s, 2H), 1.29 (m, 10H), 0.88 (t, J = 6.8 Hz, 3H). m.p. = 55° C. |
| Ionic Liquid 10 | $^1$H NMR ($\delta_H$/ppm, 400 MHz, CDCl$_3$) δ 4.12 (m, 1H), 4.10-3.91 (m, 6H), 3.75 (s, 2H), 3.65 (m, 4H), 3.54 (s, 2H), 3.38 (s, 3H), 3.25 (s, 7H), 3.12 (m, 1H), 1.74 (s, 2H), 1.65 (s, 1H), 1.54 (s, 1H), 1.50-1.22 (m, 20H), 0.89 (m, 12H). Tg = −81° C. |
| Ionic Liquid 11 | $^1$H NMR ($\delta_H$/ppm, 400 MHz, CDCl$_3$): $^1$H NMR (400 MHz, CDCl$_3$) δ 4.15-3.86 (m, 6H), 3.81-3.71 (m, 2H), 3.71-3.59 (m, 4H), 3.59-3.43 (m, 4H), 3.31-3.16 (m, 7H), 3.09 (m, 1H), 2.07 (s, 1H), 1.57 (m, 2H), 1.46-1.19 (m, 17H), 1.18 (m, 2H), 0.96-0.80 (m, 10H). |
| Ionic Liquid 12 | $^1$H NMR ($\delta_H$/ppm, 400 MHz, CDCl$_3$) δ 7.58 (s, 2H), 7.44 (s, 3H), 4.72 (s, 2H), 4.16 (m, 1H), 3.97 (m, 4H), 3.31 (m, 3H), 3.15 (m, 7H), 1.60 (s, 1H), 1.51 (s, 1H), 1.45-1.17 (m, 26H), 0.93-0.79 (m, 15H). |

Example 2—Isoteniscope Vapour Pressure Measurement

The vapour pressure for the PRM in combination with the ionic liquids is measured using the isoteniscope method as described herein above, and the activity coefficient is determined. The results are provided in Tables 11-13.

Example 2a

Ionic Liquid: Ionic Liquid 10
DMBCB$^a$ P$_0$: pure PRM at 80° C. 6.4 mbar$^b$
Ionic Liquid P$_0$: at 80° C. 2.2 mbar$^b$ due to presence of water

TABLE 11

Activity Coefficient Measurement for Single Ionic Liquid Composition

| PRM mole fraction in Ionic Liquid | Vapour Pressue measured by Isoteniscope at 80° C. (mbar)$^b$ | Vapour Pressure adjusted for water (mbar)$^c$ | Ideal Vapour Pressure at 80° C. according to Raoult's Law (mbar) | Activity coefficient = Adjusted Vapour Pressure/Ideal Vapour Pressure |
|---|---|---|---|---|
| 0.2 | 5.0 | 3.24 | 6.4 * 0.2 = 1.28 | 2.5 |
| 0.4 | 5.4 | 4.08 | 6.4 * 0.4 = 2.56 | 1.6 |
| 0.6 | 6.6 | 5.72 | 6.4 * 0.6 = 3.84 | 1.5 |
| 0.8 | 8.8 | 8.36 | 6.4 * 0.8 = 5.12 | 1.6 |

$^a$ Dimethyl benzyl carbinyl butyrate (Vapour Pressure = 0.00168 Torr (0.000223 kPa) at 25° C.) (International Flavours and Fragrances, New Jersey, USA).
$^b$ Average of 2 experiments.
$^c$ Water vapour pressure subtracted from total pressure after ratio of Ionic Liquid applied = [measured vapour pressure at X$_i$] − [Ionic Liquid P$^0$] * (1 − X$_i$).

The activity co-efficient of DMBCB at 0.2, 0.4 0.6 and 0.8 mole fractions of DMBCB is greater than 1.

Example 2b

Ionic Liquid: Ionic Liquid 12
DMBCB$^a$ P$_0$: pure PRM at 80° C. 7.5 mbar
Ionic Liquid P$_0$: at 80° C. 4.4 mbar due to presence of water

TABLE 12

Activity Coefficient Measurement for Single Ionic Liquid Composition

| PRM mole fraction in Ionic Liquid | Vapour Pressure measured using Isoteniscope method at 80° C. (mbar) | Vapour Pressure adjusted for water (mbar)$^c$ | Ideal Vapour Pressure at 80° C. according to Raoult's Law (mbar) | Activity coefficient = Adjusted Vapour Pressure/Ideal Vapour Pressure |
|---|---|---|---|---|
| 0.6 | 7.1 | 5.34 | 7.5 * 0.6 = 4.5 | 1.2 |
| 0.8 | 13.0 | 12.12 | 7.5 * 0.8 = 6.0 | 2.0 |

$^a$ Dimethyl benzyl carbinyl butyrate (VP = 0.00168 Torr (0.000223 kPa) at 25° C.) (International Flavours and Fragrances, New Jersey, USA).
$^c$ Water vapour pressure subtracted from total pressure after ratio of Ionic Liquid applied = [measured vapour pressure at X$_i$] − [Ionic Liquid P$^0$] * (1 − X$_i$).

The activity co-efficient of DMBCB at 0.6 and 0.8 mole fractions of DMBCB is greater than 1.

Example 2c

Mixed Ionic Liquid Comprising Ionic Liquid 7 & Ionic Liquid 10 in a 45:55 mole ratio
DMBCB[a] $P_0$: pure PRM at 80° C. 7.4 mbar[b]
Ionic Liquid $P_0$: at 80° C. 2.9 mbar[b] due to presence of water

TABLE 13

Activity Coefficient Measurement for Mixed Ionic Liquid Composition

| PRM mole fraction in Ionic Liquid | Vapour Pressue measured using Isoteniscope methodat 80° C. (mbar)[b] | Vapour Pressure adjusted for water (mbar)[c] | Ideal Vapour Pressure at 80° C. according to Raoult's Law (mbar) | Activity coefficient = Adjusted Vapour Pressure/Ideal Vapour Pressure |
|---|---|---|---|---|
| 0.4 | 6.6 | 4.86 | 7.4 * 0.4 = 2.96 | 1.6 |
| 0.6 | 8.9 | 7.74 | 7.4 * 0.6 = 4.44 | 1.7 |
| 0.8 | 15.0 | 14.42 | 7.4 * 0.8 = 5.92 | 2.4 |

[a] Dimethyl benzyl carbinyl butyrate (VP = 0.00168 Torr (0.000223 kPa) at 25° C.) (International Flavours and Fragrances, New Jersey, USA).
[b] Average of 2 experiments.
[c] Water vapour pressure subtracted from total pressure after ratio of Ionic Liquid applied = [measured vapour pressure at $X_i$] − [Ionic Liquid $P^0$] * (1 − $X_i$).

The activity co-efficient of DMBCB at 0.4 0.6 and 0.8 mole fractions of DMBCB is greater than 1.

Example 3—Relative Gas-Phase Concentration Measurement

The Relative Gas-Phase Concentration for the PRM in combination with the ionic liquids is measured using the Infra-Red Spectroscopy method as described herein above, and the activity coefficient is determined

Example 3a

The Gas-Phase IR peak height of DMBCB in Ionic Liquid 10 at 1,746 cm$^{-1}$ at 45° C. (8 meters) is shown in FIG. 5.

The activity coefficients for DMBCB in Ionic Liquid 10 are provided in Table 14.

TABLE 14

Activity Coefficient Measurement for Single Ionic Liquid Composition

| PRM[a] Mole Fraction in Ionic Liquid | Peak Height at 1,746 cm$^{-1}$ at 45° C. using Gas-phase IR method (% transmittance) | Activity coefficient at 45° C. = Peak Height/(mole fraction * Peak Height for pure PRM[c]) |
|---|---|---|
| 0.2 | 27.17[b] | 27.17/(0.2*39.78) = 3.42 |
| 0.4 | 31.43 | 31.43/(0.4*39.78) = 1.98 |
| 0.6 | 36.52 | 36.52/(0.6*39.78) = 1.53 |

[a] Dimethyl benzyl carbinyl butyrate (VP = 0.00168 Torr (0.000223 kPa) at 25° C.) (International Flavours and Fragrances, New Jersey, USA).
[b] Average of 2 measurements.
[c] Peak Height for pure PRM = 39.78% transmittance (average of 2 measurements).

The activity co-efficient of DMBCB at 0.2, 0.4 and 0.6 mole fractions of DMBCB is greater than 1.

Example 3b

The IR peak height of DMBCB in Ionic Liquid 12 at 1,746 cm$^{-1}$ at 45° C. (8 meters) is shown in FIG. 6.

The activity coefficients for DMBCB in Ionic Liquid 12 are provided in Table 15.

TABLE 15

Activity Coefficient Measurement for Single Ionic Liquid Composition

| PRM[a] Mole Fraction in Ionic Liquid | Peak Height at 1,746 cm$^{-1}$ at 45° C. using Gas-phase IR method (% transmittance) | Activity coefficient at 45° C. = Peak Height/(mole fraction * Peak Height for pure PRM[b]) |
|---|---|---|
| 0.2 | 21.95 | 21.95/(0.2*39.78) = 2.76 |
| 0.4 | 39.46 | 39.46/(0.4*39.78) = 2.48 |
| 0.6 | 35.54 | 35.54/(0.6*39.78) = 1.49 |
| 0.8 | 33.52 | 33.52/(0.8*39.78) = 1.05 |

[a] Dimethyl benzyl carbinyl butyrate (VP = 0.00168 Torr (0.000223 kPa) at 25° C.) (International Flavours and Fragrances, New Jersey, USA).
[b] Peak Height for pure PRM = 39.78 (% transmittance) (average of 2 measurements).

The activity co-efficient of DMBCB at 0.2, 0.4, 0.6 and 0.8 mole fractions of DMBCB is greater than 1.

Example 3c

The IR peak height of DMBCB in Ionic Liquid 7 & Ionic Liquid 10 in a 45:55 mole ratio at 1,746 cm$^{-1}$ at 45° C. (8 meters) is shown in FIG. 7.

The activity coefficients for DMBCB in the mixed ionic liquid comprising Ionic Liquid 7 & Ionic Liquid 10 in a 45:55 mole ratio are provided in Table 16.

TABLE 16

Activity Coefficient Measurement for Single Ionic Liquid Composition

| PRM[a] Mole Fraction in Ionic Liquid | Peak Height at 1,746 cm$^{-1}$ at 45° C. using Gas-phase IR method (% transmittance) | Activity coefficient at 45° C. = Peak Height/(mole fraction * Peak Height for pure PRM[b]) |
|---|---|---|
| 0.2 | 26.78 | 26.78/(0.2*39.78) = 3.37 |
| 0.4 | 35.26 | 35.26/(0.4*39.78) = 2.22 |

TABLE 16-continued

Activity Coefficient Measurement for
Single Ionic Liquid Composition

| PRM [a] Mole Fraction in Ionic Liquid | Peak Height at 1,746 cm$^{-1}$ at 45° C. using Gas-phase IR method (% transmittance) | Activity coefficient at 45° C. = Peak Height/(mole fraction * Peak Height for pure PRM [b]) |
|---|---|---|
| 0.6 | 36.52 | 36.52/(0.6*39.78) = 1.53 |
| 0.8 | 40.41 | 40.41/(0.8*39.78) = 1.27 |

[a] Dimethyl benzyl carbinyl butyrate (VP = 0.00168 Torr (0.000223 kPa) at 25° C.) (International Flavours and Fragrances, New Jersey, USA).
[b] Peak Height for pure PRM = 39.78 (% transmittance) (average of 2 measurements).

The activity co-efficient of DMBCB at 0.2, 0.4, 0.6 and 0.8 mole fractions of DMBCB is greater than 1.

Example 3d

The IR peak height of DMBCB in Ionic Liquid 7 at 1,746 cm$^{-1}$ at 45° C. (8 meters) is shown in FIG. 8.

The activity coefficients for DMBCB in Ionic Liquid 7 are provided in Table 17.

TABLE 17

Activity Coefficient Measurement for
Single Ionic Liquid Composition

| PRM [a] Mole Fraction in Ionic Liquid | Peak Height at 1,746 cm$^{-1}$ at 45° C. using Gas-phase IR method (% transmittance) | Activity coefficient at 45° C. = Peak Height/(mole fraction * Peak Height for pure PRM [b]) |
|---|---|---|
| 0.05 | 49.07 | 49.07/(0.05*39.78) = 24.67 |
| 0.2 | 44.16 | 44.16/(0.2*39.78) = 5.55 |
| 0.4 | 42.54 | 42.54/(0.4*39.78) = 2.67 |

[a] Dimethyl benzyl carbinyl butyrate (VP = 0.00168 Torr (0.000223 kPa) at 25° C.) (International Flavours and Fragrances, New Jersey, USA).
[b] Peak Height for pure PRM = 39.78 (% transmittance) (average of 2 measurements).

The activity co-efficient of DMBCB at 0.05, 0.2 and 0.4 mole fractions of DMBCB is greater than 1.

Example 4—Repulsion of PRMs in Closed System

Ionic liquid formulations in Table 8 are tested in accordance with the protocol described in the Method Section, and the repulsion of the PRMs in a closed system is evaluated. The results are provided in Table 18.

TABLE 18

Repulsion of Single PRMs in Closed System

| Formulation | PRM | Solvent | Ionic liquid | Headspace integral (area * time) |
|---|---|---|---|---|
| Formulation A | DMBCB [a] (5 wt %) | DPG [b] (95 wt %) | — | 66 |
| Formulation B | DMBCB [a] (5 wt %) | TEC [c] (95 wt %) | — | 78 |
| Formulation C | DMBCB [a] (5 wt %) | — | 52.5 wt % IL Example 7 & 42.5 wt % IL Example 10 | 93 |

[a] Dimethyl benzyl carbinyl butyrate (VP = 0.00168 Torr (0.00022 kPa) at 25° C.) (International Flavours and Fragrances, New Jersey, USA).
[b] Diproylylene glycol (from Sigma Aldrich).
[c] Triethyl citrate from (Sigma Aldrich).

Formulations A-C contain 5 wt % of a less volatile PRM. In Formulation A & B, the PRM is solubilised in a traditional perfumery solvent, DPG or TEC, and a certain equilibrium headspace concentration is achieved, as above. The same amount of the PRM is instead present in a fragrance composition comprising ionic liquids in Formulation C. The equilibrium headspace concentration achieved is increased in Formulation C versus A or B demonstrating the repulsion effect of the ionic liquid.

Example 5—Olfactory Test

Ionic liquid formulations in Table 8 are tested in accordance with the protocol described in the Method Section, and the olfactive profile, strength and character, of the PRMs in an open system is evaluated. The results are provided in Table 19.

TABLE 19

Olfactive profile of single PRMs in Open System [c]

| | | Time After Application | | | | |
|---|---|---|---|---|---|---|
| | | 10 min | 1 h | 3 h | 5 h | 24 h |
| Formulation A | 5 wt % DMBCB [a] in 95 wt % DPG [b] | 4.0 Harsh green | 4.0 Harsh green | 3.0 Harsh green | 3.0 Harsh green | 2.0 Sweeter green |
| Formulation C | 5 wt % DMBCB [a] in 52.5 wt % IL Example 7 & 42.5 wt % IL Example 10 | 5.0 Very fruity, prune | 5.0 Very fruity, prune | 5.0 Very fruity, prune | 4.0 Very fruity, prune | 1.5 Very weak, fruity |

[a] Dimethyl benzyl carbinyl butyrate (VP = 0.00168 Torr (0.00022 kPa) at 25° C.) (International Flavours and Fragrances, New Jersey, USA).
[b] Diproylene glycol from Sigma Aldrich.
[c] Expert evaluation by 2 trained noses: perfumer & evaluator.

All formulations contain 5 wt % of a less volatile PRM. This material imparts a green fruity character. In Formulation A, the PRM is solubilised in a traditional perfumery solvent, DPG, and a moderate fragrance strength is perceived from the start that only falls by 1 units after 3 hours and is still perceived for 24 hours. The character also remains a fairly constant green note. The same amount of the PRM is instead present in a fragrance composition comprising ionic liquids. In Formulation C, the initial strength is greater by 1 unit compared to Formulation A and this difference is maintained for up to 5 hours demonstrating the repulsion effect of the ionic liquid. 24 hours after application the odour from the ionic liquid containing composition is weaker demonstrating the repulsion effect of the ionic liquid where the perfume material is soon to be exhausted.

Example 6—Fragrance Compositions

The following are non-limiting examples of fragrance compositions containing ionic liquids of the present invention. They are prepared by admixture of the components described in Table 20, in the proportions indicated.

TABLE 20

| | Fragrance Compositions | | | | |
|---|---|---|---|---|---|
| | Fragrance Compositions (wt % [a]) | | | | |
| Ingredients | I | II | III | IV | V |
| DMBCB [b] | 33.5 | 6.7 | 2.5 | 0.5 | 5 |
| Magnolan [c] | 33.5 | 60.3 | 2.5 | 0.5 | 90 |
| Ionic liquid [d] | 33.0 | 33.0 | 95 | 99 | 5 |

[a] wt % relative to the total weight of the composition.
[b] Dimethyl benzyl carbinyl butyrate (VP = 0.00168 Torr (0.00022 kPa) at 25° C.) (International Flavours and Fragrances, New Jersey, USA).
[c] Magnolan (VP = 0.00251 Torr (0.00033 kPa) at 25° C.) (Symrise, Germany).
[d] Can be any ionic liquids Examples 1-12 or mixtures thereof.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fragrance composition comprising:
   (a) from 0.001% to 99.9% by weight of the total fragrance composition of dimethyl benzyl carbonyl butyrate as a perfume raw material and
   (b) from 0.01% to 99% by weight of the total fragrance composition of at least two ionic liquids selected from:
   i. at least one of (N-ethyl-2-(2-methoxyethoxy)-N,N-dimethylethanaminium) 6-methyl-3,4-dihydro-1,2,3-oxathiazin-4-one 2.2-dioxide; 2-(2-ethoxyethoxy)-N-ethyl-N,N-dimethylethanamimum 6-methyl-3,4-dihydro-1,2,3-oxathiazin-4-one 2,2-dioxide; and mixtures thereof, and
   ii) (N-ethyl-2-(2-methoxyethoxy)N,N-dimethylethanaminium)1.4-bis(2-ethylhexoxy)-1.4-dioxobutane-2-sulfonate,
   wherein the combination of ionic liquids is a liquid at temperatures lower than 100° C.

2. The fragrance composition according to claim 1 further comprising:
   (c) from about 10 wt % to about 80 wt % by weight of the total fragrance composition of a volatile solvent; and
   (d) from about 0.1 wt % to about 50 wt % by weight of the total fragrance composition of a low volatility co-solvent or a mixture of low volatility co-solvents.

3. A product comprising a fragrance composition according to claim 1, wherein the product is selected from the group consisting of a perfume, an eau de toilette, an eau de parfum, a cologne, and an after shave.

* * * * *